(12) United States Patent
Fernandes et al.

(10) Patent No.: US 7,658,727 B1
(45) Date of Patent: Feb. 9, 2010

(54) IMPLANTABLE MEDICAL DEVICE WITH ENHANCED BIOCOMPATIBILITY AND BIOSTABILITY

(75) Inventors: Brian C. A. Fernandes, Roseville, MN (US); Maura G. Donovan, St. Paul, MN (US); Randall V. Sparer, Andover, MN (US); Jesus W. Casas-Bejar, Brooklyn Park, MN (US); Mark W. Torrianni, San Juan Capistrano, CA (US)

(73) Assignee: Medtronic, Inc, Minneapolis, MN (US)

( * ) Notice: Subject to any disclaimer, the term of this patent is extended or adjusted under 35 U.S.C. 154(b) by 0 days.

(21) Appl. No.: 09/301,842

(22) Filed: Apr. 29, 1999

Related U.S. Application Data

(63) Continuation-in-part of application No. 09/063,227, filed on Apr. 20, 1998, now abandoned.

(60) Provisional application No. 60/117,837, filed on Jan. 29, 1999.

(51) Int. Cl.
*A61M 5/32* (2006.01)
(52) U.S. Cl. .................................................. 604/265
(58) Field of Classification Search ......... 604/263–265, 604/266; 424/424–426
See application file for complete search history.

(56) References Cited

U.S. PATENT DOCUMENTS

| | | | |
|---|---|---|---|
| 4,348,329 A * | 9/1982 | Chapman | 554/80 |
| 4,506,680 A | 3/1985 | Stokes | |
| 4,577,642 A | 3/1986 | Stokes | |
| 4,585,652 A | 4/1986 | Miller et al. | |
| 4,784,161 A | 11/1988 | Skalsky et al. | |
| 4,873,308 A | 10/1989 | Coury et al. | |
| 4,922,926 A | 5/1990 | Hirschberg et al. | |
| 4,972,848 A | 11/1990 | Di Domenico et al. | |
| 5,002,067 A | 3/1991 | Berthelsen et al. | |
| 5,009,229 A | 4/1991 | Grandjean et al. | |
| 5,092,332 A | 3/1992 | Lee et al. | |
| 5,103,837 A | 4/1992 | Weidlich et al. | |
| 5,229,172 A | 7/1993 | Cahalan et al. | |
| 5,258,023 A | 11/1993 | Reger | |
| 5,265,608 A | 11/1993 | Lee et al. | |
| 5,282,844 A | 2/1994 | Stokes et al. | |
| 5,324,324 A | 6/1994 | Vachon et al. | |
| 5,344,438 A | 9/1994 | Testerman et al. | |
| 5,408,744 A | 4/1995 | Gates | |
| 5,431,681 A | 7/1995 | Helland | |
| 5,447,533 A | 9/1995 | Vachon et al. | |
| 5,447,724 A * | 9/1995 | Helmus et al. | 424/426 |
| 5,449,384 A | 9/1995 | Johnson | |
| 5,510,077 A | 4/1996 | Dinh et al. | |
| 5,554,182 A | 9/1996 | Dinh et al. | |
| 5,591,227 A | 1/1997 | Dinh et al. | |
| 5,599,352 A | 2/1997 | Dinh et al. | |
| 5,607,417 A * | 3/1997 | Batich et al. | 604/890.1 |
| 5,609,629 A * | 3/1997 | Fearnot et al. | 623/1 |
| 5,624,411 A | 4/1997 | Tuch | |
| 5,645,587 A * | 7/1997 | Chanda et al. | 623/11 |
| 5,679,400 A | 10/1997 | Tuch | |
| 5,716,397 A * | 2/1998 | Myers | 623/2 |
| 5,727,555 A | 3/1998 | Chait | |
| 5,788,979 A | 8/1998 | Alt et al. | |
| 5,869,170 A * | 2/1999 | Cima et al. | 428/304.4 |
| 5,895,419 A * | 4/1999 | Tweden et al. | 623/2 |

FOREIGN PATENT DOCUMENTS

| | | |
|---|---|---|
| EP | 0832655 A2 | 4/1998 |
| EP | 0953320 A2 | 11/1999 |
| GB | 1067118 | 5/1997 |
| WO | WO 82/02829 | 9/1982 |
| WO | WO 91/17744 A | 11/1991 |
| WO | WO 95/28899 | 11/1995 |
| WO | WO 96/30060 | 3/1996 |
| WO | WO 97/15245 | 5/1997 |
| WO | WO 98/36784 | 9/1998 |

OTHER PUBLICATIONS

European Search Report, Jun. 25, 2008.
Ackerman, et al., "Purification of Human Monocytes on Microexudate-Coated Surfaces", Journal Immunol., 120:1372-1374, 1978.
Alderson, et al., "A Simple Method of Lymphocyte Purification from Human Peripheral Blood", Journal Immunol. Methods, 11:297-301, 1976.
Anderson, "Mechanisms of Inflammation and Infection with Implanted Devices", Cardiovascular Pathol., 2:335-415, 1993.
Anderson, "Inflammatory Response in Implants", TASAIO, XXXIV, 101, 1988.
Boyum, et al., "Density-Dependent Separation of White Blood Cells", Blood Separation and Plasma Fractionation, 217-239, (eds) James Harris, Wiley-Liss, Inc., 1991.
Brais, et al., "Acceleration of Tissue Ingrowth on Materials Implanted in the Heart", The Annals of Thoracic Surgery, 21:221-229 1976.
Cardona, et al., "TNF and IL-1 Generation by Human Monocytes in Response to Biomaterials", Journal Biom. Mat. Res., 26:851-859, 1992.
Casas-Bejar, et al., "In vitro Macrophage-Mediated Oxidation and Stress Cracking in a Polyetherurethane", Transactions of the Fifth World Biomaterials Congress, Toronto, Canada, p. 609, 1996.
Cenni, et al., "Platelet and Coagulation Factor Variations Induced in vitro by Polyethylene Terephithalate (Dacron) Coated with Pyrolytic Carbon", Biomaterials, 16:973-976, 1995.

(Continued)

*Primary Examiner*—Ann Y Lam
(74) *Attorney, Agent, or Firm*—James H. Ackley; Kenneth J. Collier

(57) ABSTRACT

An implantable medical device comprising a drug-loaded polymer overlaid with a fabric that promotes tissue ingrowth is useful in a wide variety of tissue engineering applications. The invention includes, for example, prosthetic heart valves, annuloplasty rings, and grafts, having enhanced biocompatibility and biostability. Methods of making and using the implantable medical devices of the invention are also included.

45 Claims, 19 Drawing Sheets

OTHER PUBLICATIONS

French, et al., "Rifampicin Antibiotic Impregnation of the St. Jude Medical Mechanical Valve Sewing Ring: A Weapon Against Endocarditis", The Journal of Thoracic and Cardiovascular Surgery, 112:248-252, 1996.

Fujimoto, et al., "Ozone-Induced Graft Polymerization onto Polymer Surface", Journal Polym. Chem., 31:1035-1043, 1993.

Kadoba, et al., Experimental Comparison of Albumin-Sealed and Gelatin-Sealed Knitted Dacron Conduits, The Journal of Thoracic and Cardiovascular Surgery, 103:1059-1067, 1992.

Kao, et al., "Role of Interleukin-4 in Foreign-Body Giant Cell Formation on a Poly(etherurethane area) In vivo", Journal Biomed. Mat. Res., 29:1267-1275, 1995.

Karck, et al., "Pretreatment of Prosthetic Valve Sewing-ring with the Antibiotic/fibrin Sealant Compound as Prophylactic Tool Against Prosthetic Valve Endocarditis", Eur. J. Cardio-thorac Surg., 4:142-146, 1990.

Leake, et al., "Comparative Study of the Thromboresistance of Dacron Combined with Various Polyurethanes", Biomaterials, 10:441-444, 1989.

Marchant, et al., "In vivo Biocompatibilty Studies. I. The Cage Implant System and a Biodegradable Hydrogel", Journal Biomed. Mat. Res., 17:301-325, 1983.

Miller, et al., "Generation of ILI-like Activity in Response to Biomedical Polymer Implants: A Comparision of in vitro and in vivo Methods", Journal of Biomed. Mat. Res., 23:1007-1026, 1989.

Miller, et al., "Human Monocyte/Macrophage Activation and Interleukin-1 Generation by Biomedical Polymers", Journal Biom. Mat. Res., 22:713-731, 1988.

Mond, et al., "The Steroid-Eluting Electrode: A 10-Year Experience", PACE, 19:1016-1020, 1996.

Onuki, et al., "Accelerated Endothelialization Model for the Study of Dacron Graft Healing", Annals of Vascular Surgery, 11:141-148, 1997.

Orszulak, et al., "The Risk of Stroke in the early Postoperative Period Following Mitral Valve Replacement", European Journal of Cardiothoracic Surgery, 9:615-620, 1995.

Perier, et al., "Comparison of Thromboembolic and Anticoagulant-Related Complications After Aortic Valve Replacement Using Starr Edwards, Bjork-Shiley and Porcine Valve Prostheses", Bodnar E. Yacoub M. (eds). Biologic and Bioprosthetic Valves: York Medical Books, 511-520, 1986.

Rubin, et al., "Preincubation of Dacron Grafts with Recombinant Tissue Factor Pathway Inhibitor Decreases their Thrombogenicity In Vivo", Journal of Vascular Surg., 24:865-870, 1996.

Schubert, et al., "Oxidative Biodegradation Mechanisms of Biaxially Strained Poly(etherurethane area) Elastomers", Journal Biomed. Mat. Res., 29:337-347, 1995.

Schwartz, et al., "Local Anticoagulation of Prosthetic Heart Valves", Circulation, 43 (Suppl III) pp. 85-89, 1973.

Shanbhag, et al., "Macrophase/Particle Interactions: Effects of Size, Composition and Surface Area", Journal Biomed. Mat. Res., 28:81-90, 1994.

Shankar, et al, "Chapter 5: Inflammation and Biomaterials", Implantation Biology, Host Response and Biomedical Devices, (eds) Ralph S. Greco, CRC Press, Inc., Boca Raton, FL pp. 67-84, 1994.

Stokes, et al., "Polyurethane Elastomer Biostabillity", Journal of Biomaterials Applications, 9:321-354, 1995.

Takahashi, "Absorption of Basic Fibroblast Growth factor onto Dacron Vascular Prosthesis and its Biological Efficacy", Artif Organs, 21:1041-1046, 1997.

Tweden, et al., "Accelerated Healing of Cardiovascular Textiles Promoted by an RGD Peptide", Journal Heart Valve Dis, 4 (Suppl I), pp. S90-97, 1995.

Van Der Lei, et al., "Improved Healing of Small-Caliber Polyetrafluorethylene Prostheses by Induction of a Clot Layer: A Review of Experimental Studies in Rats", International Angiology, 10:202-208, 1991.

Wilkerson, et al., Biiomaterials Used in Peripheral Vascular Surgery (eds) Ralph S. Creco, CRC Press, Inc.,, Implantation Biology: The host Responses and Biomedical Devices, pp. 179-190, 1994.

Zhao, et al., "Cellular Interactions and Biomaterials: In vivo Cracking of Pre-stressed Pellethane 2363 80A", Journal Biom. Mat. Res., 24:621-637, 1990.

Zhao, et al., "Glass Wool-H202/CoCI2 Test System for In Vitro Evaluation of Biodegradative Stress Cracking in Polyurethane Elastomers", Journal Biomed. Mat. Res., 29:467-475, 1995.

Brais et al., "Acceleration of Tissue Ingrowth on Materials Implanted in the Heart", The Annals of Thoracic Surgery, 21, 221-229 (1976).

Cenni et al., "Platelet and coagulation factor variations induced in vitro by polyethylene terephthalate (Dacron® ) coated with pyrolytic carbon", Biomaterials, 16, 973-976 (1995).

French et al., "Rifampicin Antibiotic Impregnation of the St. Jude Medical Mechanical Valve Sewing Ring: A Weapon Against Endocarditis", The Journal of Thoracic and Cardiovascular Surgery, 112, 248-252 (1996).

Kadoba et al., "Experimental comparison of albumin-sealed and gelatin-sealed knitted Dacron conduits", The Journal of Thoracic and Cardiovascular Surgery, 103, 1059-1067 (1992).

Karck et al., "Pretreatment of prosthetic valve sewing-ring with the antibiotic/fibrin sealant compounds as prophylactic tool against prosthetic valve endocarditis", Eur. J. Cardio-thorac Surg., 4, 142-146 (1990).

Leake et al., "Comparative Study of the thromboresistance of Dacron® combined with various polyurethanes", Biomaterials, 10, 441-444 (1989).

Miller et al., "Generation of IL1-like activity in response to biomedical polymer implants: A comparison of in vitro and in vivo methods", J. of Biomed. Mat. Res., 23, 1007-1026 (1989).

Onuki et al., "Accelerated Endothelialization Model for the Study of Dacron Graft Healing", Annals of Vascular Surgery, 11, 141-148 (1997).

Orszulak et al., "The risk of stroke in the early postoperative period following mitral valve replacement", European Journal of Cardiothoracic Surgery, 9, 615-620 (1995).

Perier et al, "Comparison of thromboembolic and anticoagulant-related complications after aortic valve replacement using Starr Edwards, Bjork-Shiley and porcine valve prostheses", Bodnar E, Yacoub M (eds). Biologic and Bioprosthetic Valves: York Medical Books, 511-520 (1986).

Rubin et al., "Preincubation of Dacron grafts with recombinant tissue factor pathway inhibitor decreases their thrombogenicity in vivo", J. Vasc. Surg., 24, 865-870 (1996).

Schwartz et al., "Local anticoagulation of prosthetic heart valves", Circulation, 43 (Suppl. III), 85-89 (1973).

Shankar et al., "Chapter 5: Inflammation and Biomaterials", Implantation Biology, Host Response and Biomedical Devices, (eds) Ralph S. Greco, CRC Press, Inc., Boca Raton, FL 67-80 (1994).

Takahashi, "Adsorption of Basic Fibroblast Growth Factor onto Dacron Vascular Prosthesis and Its Biological Efficacy" Artif Organs, 21, 1041-1046 (1997).

Tweden et al., "Accelerated Healing of Cardiovascular Textiles Promoted by an RGD Peptide", J. Heart Valve Dis, 4 (Suppl. I), S90-97 (1995).

Van Der Lei et al., "Improved healing of small-caliber polytetrafluoroethylene prostheses by induction of a clot layer: a review of experimental studies in rats", International Angiology 10, 202-208 (1991).

Wilkerson et al., "Biomaterials Used in Peripheral Vascular Surgery" (eds) Ralph S. Greco, CRC Press Inc., Implantation Biology: The Host Responses and Biomedical Devices, 179-190 (1994).

* cited by examiner

IMPLANTABLE MEDICAL DEVICE WITH ENHANCED BIOCOMPATIBILITY AND BIOSTABILITY

REFERENCE TO RELATED APPLICATIONS

This patent application claims the benefit of U.S. Provisional Patent Application Ser. No. 60/117,837 filed 29 Jan. 1999, and is a continuation-in-part of U.S. Ser. No. 09/063,227 filed Apr. 20, 1998 now abandoned.

FIELD OF THE INVENTION

This invention relates generally to medical implantable medical devices, specifically prosthetic heart valves, annuloplasty rings, and grafts, with enhanced biocompatibility and biostability.

BACKGROUND OF THE INVENTION

Heart valve disease falls into two major categories: acquired or congenital. In either case, the valve and/or the subvalvular apparatus is damaged. Damage of these structures can lead to valves becoming either incompetent or stenotic.

Incompetent valves suffer from degenerative changes leading to enlargement of the valve annulus. Enlargement of the annulus forces leaflets apart. As the leaflets get father apart, the leaflets do not meet properly, causing improper leaflet coaptation. This inability to close properly results in improper blood flow through the heat and eventually requires surgical correction either by valve repair or replacement.

Valve repair, also known as valvular annuloplasty, involves repairing the valve annulus by reinforcing the structure with a ring-shaped device or band fashioned from cloth materials. By properly sizing and installing the device, known as an annuloplasty ring, the surgeon can restore the valve annulus to its original, undilated circumference. This annular restoration will bring the leaflets back into correct alignment and restore valve competence.

Stenotic valves are valves in which the leaflets have lost their ability to move freely. Besides allowing for regurgitant flow across the valve, stenotic valves have a decrease in the valve orifice area. The decrease in orifice area creates large transvalvular pressure gradients. This condition forces the heart to work harder. The result is enlargement of the ventricles. Surgical procedures to correct such conditions require valve replacement.

Currently there are two types of prosthetic valves that can be used to replace failing valves: 1) mechanical and 2) bioprosthetic.

Mechanical valves are valves made on non-biological materials, consisting of a valve housing, a flow occluder, and a sewing ring. Bioprosthetic valves are composed of housing (known as a stent), a flow occluder (usually pericardium or aortic root tissue from animal sources that has been chemically preserved) and sewing ring. Like annuloplasty rings, mechanical and bioprosthetic valve sewing rings are composed of polyester cloth material constructed in either a knitted or woven configuration. The configuration of the cloth allows for cellular infiltration into the interstices of the fabric enabling the prosthesis to "heal in". The "healing in" process creates a biological surface that is nonthrombogenic and acts as a barrier to transvalvular leaks.

Historically, polyester was chosen as the cloth material because of the healing response it elicited. Polyester was also chosen for its chemical inertness and resistance to enzymatic degradation. However, implantation of these nonresorbable materials permanently alters the microenvironment of the tissue where it is implanted. At the time of implantation the tissue of the valve annulus undergoes trauma from leaflet removal, dissecting away damaged and/or mineralized tissue, handling, sizing and suturing operations. The trauma results in the generation of a wound, with healing of the wound involving an inflammatory response. The nature and extent of the inflammatory response is dependent on the size of the wound bed as well as the nature of the material implanted into the wound. The result can be incomplete or improper healing.

In its simplest terms, the inflammatory response is divided into two phases, an acute phase and a chronic phase. Full details of the events of each phase are well documented by Shankar et al. (Chapter 5, "Inflammation and Biomaterials" in *Implantation Biology, Host Response and Biomedical Devices*, Ralph S. Greco, Ed., CRC Press, Inc., Boca Raton, Fla., 1994, 68-80). If the acute inflammatory response is not totally resolved it can progress to the chronic phase. The sequalae of events in the chronic inflammatory response can result in serious complications to valve function. Along with the deposition of inflammatory cells and the accumulation of cellular and proteinaceous blood elements, there is the formation of a fibrous sheath (of host origin) known as pannus. This fibrous tissue develops as an extension of the tissue healing the sewing ring. In the case of bioprosthetic tissue valves, if the inflammatory response is not resolved, the resulting pannus continues to grow, with the advancing fibrous tissue extending out onto the leaflets causing stenosis and/or incompetence. In addition to causing stenosis by inhibiting leaflet function, tissue overgrowth has been shown to cause leaflet retraction in pericardial valves, resulting in clinically significant regurgitation. Blood stasis or pooling is an other result of compromised leaflets. The progression of valve dysfunction in bioprosthesis is patient-dependent, and relates to how aggressive the patient's inflammatory response is to the implant. The progression of healing for mechanical valve recipients is similar to that observed with bioprosthetic but can have even more serious consequences. Tissue growth onto the valve can obstruct the occluder causing catastrophic failure of the valve. Thus, replacement valves, whether bioprosthetic or mechanical, often have shortcomings which may necessitate their removal. Because of the exuberant pannus growth into and onto the sewing ring of these valves, however, removal of the valves requires extensive dissection, making subsequent operations even more difficult.

Medical devices containing polymers are known to include therapeutic agents for delivery to surrounding tissue. For example, stents have been designed with polymeric coatings or films that incorporate a wide variety of therapeutic agents, such as anti-inflammatory agents, anti-thrombogenic agents, and anti-proliferative agents, for a wide variety of purposes. Antimicrobial compounds have been incorporated into polymeric portions of medical devices for sustained release to the surrounding tissue to enhance infection-resistance. Medical electrical leads have incorporated steroids into or at the lead tip electrode, to reduce source impedance and lower peak and chronic pacing thresholds. However, to date anti-inflammatory agents have not been recognized as useful for improving the biocompatibility and/or biostability of biomaterials used in implantable medical devices, particularly those that may need to be removed.

The polyester fabric typically used for manufacturing sewing rings of cardiac prosthetic valves, as well as annuloplasty rings and stent coverings, is thrombogenic and inflammatory in nature. It is known to activate complement and coagulation cascades, and has demonstrated a higher propensity for platelet deposition and thrombus formation prior to healing and tissue incorporation. It has been postulated that the thromboreactivity of the sewing ring material is the main culprit in the high incidences of thromboemboli related phenomena observed in the early postoperative period (T. Orszulak et al., 8th Annu. Meeting Eur. Assoc. Cardiacthoracic Surg. 1994: 98; P. Perier et al., in E Bodner et al., Eds., Biologic and Bioprosthetic Valves, York Medical Books, 1986: 511-520).

There have been numerous attempts to treat polyester for the purpose of improving its function in vivo. Most have focused on reducing thromboreactivity of polyester in the hopes that the healing response would be accelerated, thereby preventing further contact with blood elements. Examples include: albumin impregnation, carbon coating, preclotting of the polyester fabric, cell seeding, synthetic peptide attachment, basic fibroblast growth factor (bFGF) attachment, fibrin coating containing bFGF and heparin, and polyurethane coating.

Ideally, medical implants should heal in well, without excessive tissue overgrowth, and allow for the establishment of a smooth neointimal transition between host and prosthesis. Reduction of the inflammatory response to porous materials such as polyester fabrics would be an important step toward complete healing of the surgical implant without the long term consequences of stenosis, regurgitation or catastrophic failure.

Many of the following lists of patents and nonpatent documents disclose information related to medical devices containing anti-inflammatory agents, particularly steroids. Others in the following lists relate inflammatory responses to polyester fabrics such as Dacron™; still others relate generally to biomaterials and human response mechanisms.

TABLE 1a

Patents

| U.S. Pat. No. | Inventor(s) | Issue Date |
| --- | --- | --- |
| 4,506,680 | Stokes | 26 Mar. 1985 |
| 4,577,642 | Stokes | 25 Mar. 1986 |
| 4,585,652 | Miller et al. | 29 Apr. 1986 |
| 4,784,161 | Skalsky et al. | 15 Nov. 1988 |
| 4,873,308 | Coury et al. | 10 Oct. 1989 |
| 4,972,848 | Di Domenico et al. | 27 Nov. 1990 |
| 4,922,926 | Hirschberg et al. | 8 May 1990 |
| 5,002,067 | Berthelsen et al. | 26 Mar. 1991 |
| 5,009,229 | Grandjean et al. | 23 Apr. 1991 |
| 5,092,332 | Lee et al. | 3 Mar. 1992 |
| 5,103,837 | Weidlich et al. | 14 Apr. 1992 |
| 5,229,172 | Cahalan et al. | 20 Jul. 1993 |
| 5,265,608 | Lee et al. | 30 Nov. 1993 |
| 5,282,844 | Stokes et al. | 1 Feb. 1994 |
| 5,324,324 | Vachon et al. | 28 Jun. 1994 |
| 5,344,438 | Testerman et al. | 6 Sep. 1994 |
| 5,408,744 | Gates | 25 Apr. 1995 |
| 5,431,681 | Helland | 11 Jul. 1995 |
| 5,447,533 | Vachon et al. | 5 Sep. 1995 |
| 5,510,077 | Dinh et al. | 23 Apr. 1996 |
| 5,554,182 | Dinh et al. | 10 Sep. 1996 |
| 5,591,227 | Dinh et al. | 7 Jan. 1997 |
| 5,599,352 | Dinh et al. | 4 Feb. 1997 |
| 5,609,629 | Fearnot et al. | 11 Mar. 1997 |
| 5,679,400 | Tuch | 21 Oct. 1997 |
| 5,624,411 | Tuch | 29 Apr. 1997 |
| 5,727,555 | Chait | 17 Mar. 1998 |

TABLE 1b

Nonpatent Documents

Ackerman et al., "Purification of Human Monocytes on Microexudate-Coated Surfaces," J. Immunol., 120, 1372-1374 (1978).
Alderson et al., "A Simple Method of Lymphocyte Purification from Human Peripheral Blood," J. Immunol. Methods, 11, 297-301 (1976).
Anderson, "Mechanisms of Inflammation and Infection with Implanted Devices," Cardiovasc. Pathol., 2, 335-415 (1993).
Anderson, "Inflammatory Response in Implants," TASAIO, XXXIV, 101 (1988).
Boyum et al., "Density-Dependent Separation of White Blood Cells," Blood Separation and Plasma Fractionation, 217-239, (eds) James Harris, Wiley-Liss, Inc. (1991).
Bonfield et al., "Cytokine and Growth Factor Production by Monocytes/Macrophages on Protein Preadsorbed Polymers," J. Biom. Mat. Res., 26, 837-850 (1992.)
Brais et al., "Acceleration of Tissue Ingrowth on Materials Implanted in the Heart", The Annals of Thoracic Surgery, 21, 221-229 (1976).
Cardona et al., "TNF and IL-1 Generation by Human Monocytes in Response to Biomaterials," J. Biom. Mat. Res., 26, 851-859 (1992).
Casas-Bejar et al., "In vitro Macrophage-Mediated Oxidation and Stress Cracking in a Polyetherurethane," Transactions of the Fifth World Biomaterials Congress, Toronto, Canada, pg. 609 (1996).
Cenni et al., "Platelet and coagulation factor variations induced in vitro by polyethylene terephthalate (Dacron ®) coated with pyrolytic carbon", Biomaterials, 16, 973-976 (1995).
French et al., "Rifampicin Antibiotic Impregnation of the St. Jude Medical Mechanical Valve Sewing Ring: A Weapon Against Endocarditis", The Journal of Thoracic and Cardiovascular Surgery, 112, 248-252 (1996).
Fujimoto et al., "Ozone-Induced Graft Polymerization onto Polymer Surface," J. Polym. Chem., 31, 1035-1043 (1993).
Kadoba et al., "Experimental comparison of albumin-sealed and gelatin-sealed knitted Dacron conduits", The Journal of Thoracic and Cardiovascular Surgery, 103, 1059-1067 (1992).
Kao et al., "Role of Interleukin-4 in Foreign-Body Giant Cell Formation on a Poly(etherurethane urea) in vivo," J. Biomed. Mat. Res., 29, 1267-1275 (1995).
Karck et al., "Pretreatment of prosthetic valve sewing-ring with the antibiotic/fibrin sealant compound as prophylactic tool against prosthetic valve endocarditis", Eur. J. Cardio-thorac Surg., 4, 142-146 (1990).
Leake et al., "Comparative Study of the thromboresistance of Dacron ® combined with various polyurethanes", Biomaterials, 10, 441-444 (1989).
Marchant et al., "In vivo Biocompatibility Studies. I. The Cage Implant System and a Biodegradable Hydrogel," J. Biomed. Mat. Res., 17, 301-325 (1983).
Miller et al., "Generation of IL1-like activity in response to biomedical polymer implants: A comparison of in vitro and in vivo methods", J. of Biomed. Mat. Res., 23, 1007-1026 (1989).
Miller et al., "Human Monocyte/Macrophage Activation and Interleukin-1 Generation by Biomedical Polymers," J. Biom. Mat. Res., 22, 713-731 (1988).
Mond et al., "The Steroid-Eluting Electrode: A 10-Year Experience," PACE, 19, 1016-1020 (1996).
Onuki et al., "Accelerated Endothelialization Model for the Study of Dacron Graft Healing", Annals of Vascular Surgery, 11, 141-148 (1997).
Orszulak et al., "The risk of stroke in the early postoperative period following mitral valve replacement", European Journal of Cardiothorasic Surgery, 9, 615-620 (1995).
Perier et al, "Comparison of thromboembolic an anticoagulant-related complications after aortic valve replacement using Starr Edwards, Bjork-Shiley and porcine valve prostheses", Bodnar E. Yacoub M (eds). Biologic and Bioprosthetic Valves: York Medical Books, 511-520 (1986).
Rubin et al., "Preincubation of Dacron grafts with recombinant tissue factor pathway inhibitor decreases their thrombogenicity in vivo", J. Vasc. Surg., 24, 865-870 (1996).
Schubert et al., "Oxidative Biodegradation Mechanisms of Biaxially Strained Poly(etherurethane urea) Elastomers," J. Biomed. Mat. Res., 29, 337-347 (1995).
Schwartz et al., "Local anticoagulation of prosthetic heart valves", Circulation, 43 (Suppl. III), 85-89 (1973).
Shanbhag et al., "Macrophage/Particle Interactions: Effects of Size, Composition and Surface Area," J. Biomed. Mater. Res., 28, 81-90 (1994).
Shankar et al., "Chapter 5: Inflammation and Biomaterials", Implantation Biology. Host Response and Biomedical Devices, (eds) Ralph S. Greco, CRC Press, Inc., Boca Raton, FL 67-80 (1994).
Stokes et al., "Polyurethane Elastomer Biostability," J. of Biomaterials Applications, 9, 321-354 (1995).
Takahashi, "Adsorption of Basic Fibroblast Growth Factor onto Dacron TABLE 1b-continued Nonpatent Documents Vascular Prosthesis and Its Biological Efficacy", Artif Organs, 21, 1041-1046 (1997).
Tweden et al., "Accelerated Healing of Cardiovascular Textiles Promoted by an RGD Peptide", J. Heart Valve Dis, 4 (Suppl. I), S90-97 (1995).
Van Der Lei et al., "Improved healing of small-caliber polytetrafluoroethylene prostheses by induction of a clot layer: a review of experimental studies in rats", International Angiology 10, 202-208 (1991).
Wilkerson et al., "Biomaterials Used in Peripheral Vascular Surgery" (eds) Ralph S. Greco, CRC Press Inc., Implantation Biology: The Host Responses and Biomedical Devices, 179-190 (1994).
Zhao et al., "Cellular Interactions and Biomaterials: In vivo Cracking of Pre-stressed Pellethane 2363-80A," J. Biom. Mat. Res., 24, 621-637 (1990).
Zhao et al., "Glass Wool-$H_2O_2$/$CoCl_2$ Test System for In Vitro Evaluation of Biodegradative Stress Cracking in Polyurethane Elastomers," J. Biomed. Mat. Res., 29, 467-475 (1995).

All patent and nonpatent documents listed in Table 1 are hereby incorporated by reference herein in their respective entireties. Citation and incorporation by reference of these documents is not, however, to be construed as an admission that any or all of the documents are prior art as to the present invention. As those of ordinary skill in the art will appreciate upon reading the Summary of the Invention, Detailed Description of the Invention, and Claims set forth below, many of the devices and methods disclosed in these documents may be modified advantageously by using the teachings of the present invention.

SUMMARY OF THE INVENTION

The present invention is directed at enhancing the biocompatibility and/or biostability of implantable medical devices. To do this, the present invention does not involve modifying the chemistries of the constituent materials of the devices, rather it involves using anti-inflammatory agents as biological response modulators to control the host's response to the constituent materials.

The term "biostable" is used herein with reference to a material's chemical and physical stability during implantation in living tissue. More specifically, it refers to resistance to the degradative phenomena to which the material is exposed during the acute and chronic host response (e.g., inflammation). In the context of the present invention, improving the biostability of a material does not involve changing the chemistry of the material; rather, it focuses on down-regulating the cellular response to the material. Thus, as used herein, biostability refers to the effects of cells and tissues on materials.

The term "biocompatible" is used herein with reference to the degree of host response elicited by a material upon implantation. Typically, this is evaluated by assessing the inflammatory phenomenon, particularly in surrounding tissues. Less inflammation or biological disturbance suggests better biocompatibility and vice versa. Thus, as used herein, biocompatibility refers to the effects of materials on cells and tissues.

Various embodiments of the present invention are intended to fulfill one or more of the following objects: to enhance material biocompatibility; to enhance material biostability; to reduce acute inflammation; to reduce chronic inflammation; and to reduce fibrous tissue formation (e.g., reduced tissue encapsulation or pannus). Specifically, the present invention seeks to minimize the host inflammatory response to implanted medical device, such as a prosthetic heart valve, annuloplasty ring, stent or pacemaker, that utilizes an inflammatory material, such as Dacron™ (polyethyleneterephthalate) fabric or PTFE (polytetrafluoroethylene) as a covering or overlay to form a surface in contact with the host tissue and/or bodily fluids.

The present invention has a number of advantages over prior art implantable devices including controlled healing, minimal pannus growth, sustained leaflet function, decreased risk of infection, decreased risk of thrombus formation and embolization, and increased valve durability. Reduction of the acute inflammatory response to implantable devices has a beneficial effect on the chronic inflammatory response. If the post-surgical inflammatory response is able to resolve itself at the acute phase, true healing of the surgical implant can occur without the long term consequences of stenosis, regurgitation or catastrophic failure. Control of the healing response prevents or reduces the deleterious effects of pannus formation on valve function and durability.

Implantable medical devices of the invention include, but are not limited to, prosthetic heart valves (both mechanical valves and tissue valves), annuloplasty rings for valvular repair, vascular grafts, sewing rings, stents, medical leads and catheters, pacemakers, and refillable drug pumps for long-term sustained drug delivery, such as the SynchroMed® implantable infusion system (Medtronic, Inc., Minneapolis, Minn.). An implantable device of the invention has a body tissue or fluid-contacting surface (an "overlayer") comprising a fabric that can take the form of a sheath, a pouch, an encasement, a layer, a film, a coating, or the like, such that the fabric is in contact with body tissue or fluids such as blood. A fabric is by definition porous, and can be woven or knitted. Preferably a polymer fabric is used as the overlayer, which is woven or knitted from polymer fibers. Nonpolymeric fabrics, however, such as collagen fabrics comprising woven fibrils of collagen, are also contemplated. A fabric possesses a rough or textured surface, which is advantageous because a textured surface facilitates the healing response. A biostable polymer fabric is particularly preferred for use in the present invention. Most preferably, the overlayer comprises a biostable polyester fabric.

The implantable device further includes, under the fabric overlayer, a body portion that serves as a physical support. The body portion imparts mechanical strength to the device and provides a structure or framework to give the device shape and form. The body portion is not limited to any particular constituent material, and it can be porous or nonporous, biodegradable or biostable, flexible or inflexible, as indicated by the intended use. It can, for example, comprise one or more of a polymer, a metal, a metal alloy, a body tissue (e.g., pericardium, fascia lata, duramater, intestinal mucosa), a collagen sponge or gel, or a synthetic peptide mixtures or gels. The body portion of the device can take the form of an underlayer, structure, or insert, for example. It should be understood that the fabric overlayer and the body portion of the device can, but need not, be in direct physical contact with each other; in other words there can, but need not be, a space between all or a portion of the fabric overlayer and all or a portion of the body portion of the device. Physical contact between the overlayer and the body portion, if it occurs, can be incidental, or it can be intentional, as where the fabric overlayer is adhered to the body portion. Moreover, although the fabric overlayer typically completely surrounds, encloses, or encases the body portion of the implantable device, is to be understood that the invention nonetheless includes implantable devices wherein only a portion of the body portion of the device is overlaid by the fabric overlayer. For example, a fabric sheet could be adhered to a selected surface of the body portion of the device.

The constituent material of the body portion of the implantable device is in intimate contact with a therapeutic agent, such as a steroidal or nonsteroidal anti-inflammatory agent, that controls, reduces or attenuates the body's inflammatory response to the implanted medical device, and which is capable of eluting through the fabric overlayer. The anti-inflammatory agent is preferably, a glucocorticosteroid, such as dexamethasone, a derivative thereof, or a salt thereof. The therapeutic agent can be coated onto, or impregnated or imbibed into, or covalently bonded to, the body portion of the device, for example. Alternatively, the therapeutic agent can be placed in a liquid core of the body portion, such that it can diffuse through a porous metal or polymer body portion or be delivered via channels formed in an otherwise nonporous body portion. Preferably, the body portion of the device contains an biostable polymer in intimate contact with an anti-inflammatory agent. In addition or alternatively, the body portion of the device can include one or more other therapeutic agents, including anti-infection agents such as antimicrobial drugs and bacteriostatic agents such as silver. For example, prosthetic valve endocarditis, which remains a dangerous complication following heart replacement, can be prospectively treated by incorporating an antibiotic into the insert of the sewing ring of the prosthetic heart valve.

Accordingly, one or more objects of the present invention are achieved by implantable medical device of the invention having one or more of the following features: (a) a fabric overlayer through which a therapeutic agent can elute; (b) a fabric overlayer which serves as a means for securing the device to the patient's body, and functions as a surface that promotes tissue ingrowth; (c) a body portion in intimate contact with an releasable therapeutic agent; (d) one or more therapeutic agents coated onto or compounded into the body portion of the device beneath the fabric overlayer, such that the therapeutic agent(s) are capable of eluting through the fabric overlayer; (e) a body portion containing an encapsulated drug reservoir containing one or more therapeutic agents capable of eluting from the body portion through the fabric overlayer; and (f) an anti-inflammatory agent, such as dexamethasone, capable of eluting through the fabric overlayer so as to mediate an overexuberant healing response to the implanted device.

An important aspect of the present invention is that the body's inflammatory response to the fabric overlayer or encasement of the implantable device is controlled not by modifying the fabric overlayer itself, but by modifying the body portion of the device which is surrounded, covered or encased by the fabric overlayer. Thus, desirable properties of the fabric overlayer (for example, its porosity, flexibility, texture, suturability, tensile strength, durability, sterilizability and biocompatibility) are not compromised.

Significantly, implantable medical devices of the invention can be used to modulate tissue encapsulation, pannus formation, and polymer degradation when implanted into a patient. Thus, the present invention also provides methods of modulating tissue encapsulation, pannus formation, or degradation of a medical electrical lead or indwelling catheter by implanting the prosthetic heart valves (both mechanical valves and tissue valves), annuloplasty rings for valvular repair, vascular grafts, sewing rings, stents, medical leads and catheters, and pacemakers described above.

The present invention also provides a variety of methods for making the implantable medical devices described above. For example the invention provides a method of making a medical sewing ring for use in a prosthetic heart valve or annuloplasty ring, which rings comprise a body portion (i.e., an annular insert) enclosed by a fabric covering. A therapeutic agent is incorporated into the annular insert such that it can subsequently elute from the insert and through the fabric overlayer. Preferably, the sewing ring insert comprises a nonporous polymeric material; more preferably, the insert is made from liquid silicone rubber and, optionally, is made radiopaque by the incorporation of barium sulfate. The sewing ring insert is preferably flexible, and the radiopacity of the insert allows the presence of the device to be monitored after completion of the implant surgery. The insert is completely enclosed by fabric sheath, for example a cloth-like material such as Dacron™ polyester. The sheath is made by folding a cloth sheet around the insert, then sewing the folded ends together. The combination of the insert and sheath result in a ring which is completely flexible yet essentially nonextensible.

DETAILED DESCRIPTION OF THE INVENTION

Figure 1A:
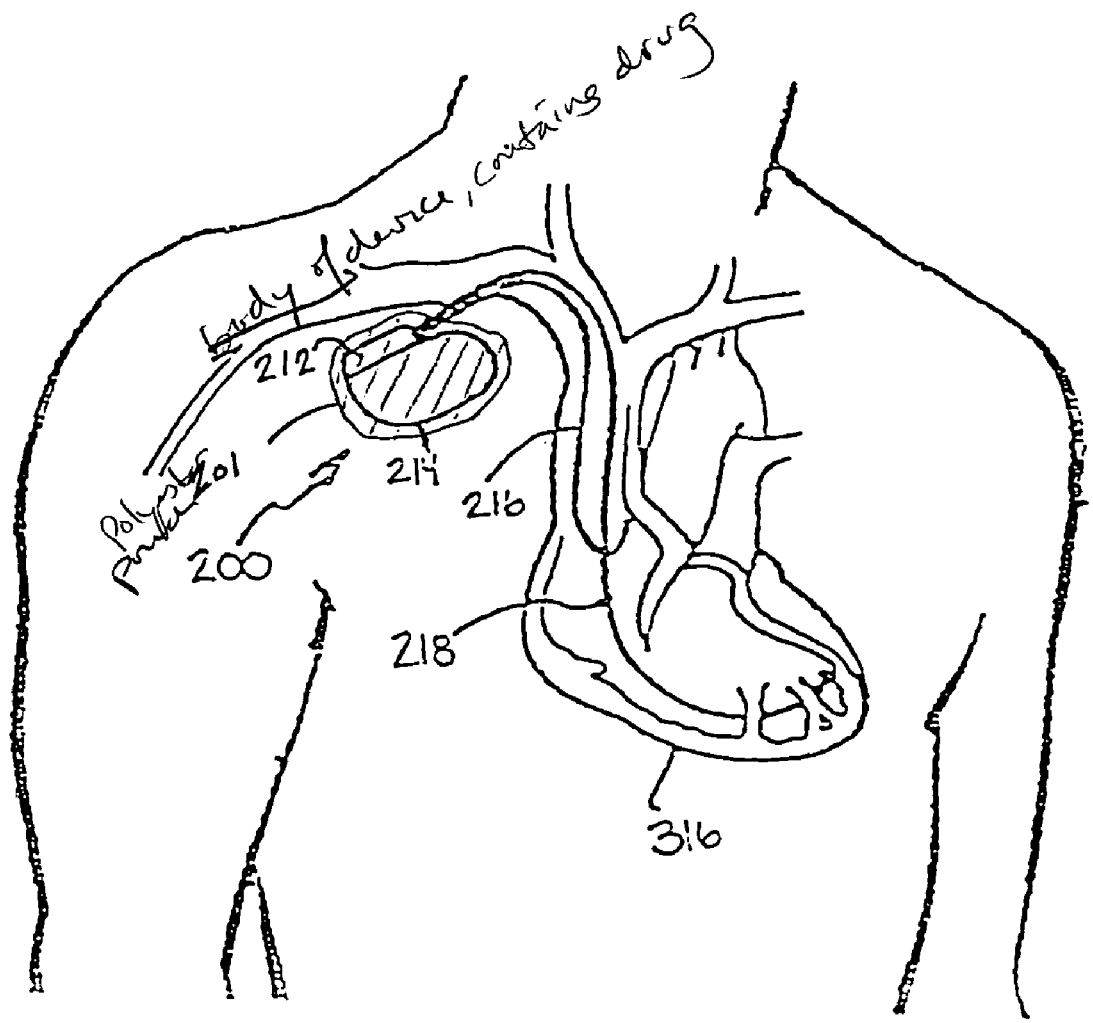
FIG. 1 is a simplified schematic view of illustrative implanted medical devices embodying the present invention: (a) a pacemaker in a polyester pouch and (b) mechanical and bioprosthetic heart valves with a polyester fabric sewing rings; SVC, superior vena cava; RA, right atrium; TV, tricuspid valve; IVC, inferior vena cava; RV, right ventricle; LV, left ventricle; PV, pulmonary vein; LA, left atrium, PA, pulmonary artery; Ao, aorta.

The present invention is directed at enhancing the biocompatibility and/or biostability of polymeric materials by modulating cellular behavior involved in biological defensive mechanisms, such as phagocytosis and enzymatic and oxidative mechanisms, and upregulation of cytokine signalling that amplifies the inflammatory response. This does not involve modifying the chemistries of the polymers per se, rather it involves using biological response modulators to "protect" the polymers. Significantly, it has been discovered that elution of such biological response modulators at the interface between the polymer and the surrounding tissue (solid or liquid tissues, e.g., blood), modulates the behavior of cells at that interface. As a result, the polymer is exposed to fewer cell-produced damaging agents, such as reactive oxygen species. In essence, the defensive mechanisms of cells in response to foreign materials is down-regulated by the present invention.

To this end, the present invention provides an implantable medical device having a body portion comprising a constituent material in intimate contact with a therapeutic agent, such as an anti-inflammatory agent, the body portion overlayed by a porous fabric. The anti-inflammatory agent elutes from the body portion of the device, through the fabric, and is effective in modulating the behavior of cells in contact with the implanted device. Significantly, the anti-inflammatory agent moderates certain cellular activities at the site of the implant that causes inflammation, for example. Such cellular activity includes upregulation of specific signaling pathways that amplify the inflammatory response, leading to exuberant tissue growth, increase in metalloprotease activity, and oxidative burst. Exuberant tissue growth refers to fibrous tissue formation as a result of cellular proliferation and deposition of extracellular components, including collagen, elastin, and fibronectin. The result is encapsulation of the implant and/or the formation of pannus, which can be detrimental because exuberant tissue growth can decrease orifice area of the prosthetic valve and encroach onto valve leaflets, inhibiting freedom of movement leading to valve stenosis. Oxidative burst refers to the ability of phagocytes to consume oxygen and produce reactive oxygen species such as hydroxyl radicals, superoxide, hydrogen peroxide, and other reactive oxides and peroxides. It tends to cause degradation of the polymer of which the implant is made. Some polymers are more resistant to oxidative degradation than others; they include fluoroelastomers such as poly(tetrafluoroethylene) (PTFE), poly(tetrafluoroethylene-hexafluoropropylene) (FEP), poly(tetrafluoroethylene-perfluoro-(propylvinylether)) (PFA), poly (ethyl-tetrafluorethylene) (ETFE); and other polymers such as polyvinylchloride (PVC), polyimides, polysulfones, polyolefins such as polypropylene, polyethylene and ethylene-propylene copolymers, and silicones. Hydrolysis of polymeric materials is also a concern.

The anti-inflammatory agent is preferably localized at the surface of the body portion of the device, from which it then passes through the fabric overlayer. Alternatively, it can be eluted from a remote site within the medical device, as long as upon elution passes through the fabric overlayer. Initial release of the anti-inflammatory agent at the site of implantation is believed to reduce cell-associated propagation of the inflammatory signal. Sustained release is believed to maintain a low level of activation and differentiation of cells that come in contact with the tissue-contacting surface.

The body portion of the medical device of the invention preferably comprises about 0.01 weight percent (wt-%) to about 10.0 wt-% therapeutic agent, more preferably about 0.1 wt-% to about 5 wt-% therapeutic agent. Of course, the amount of therapeutic agent loaded into the device depends on the efficacy of the agent, the purpose for which it is being administered, the age and condition of the patient, and the intended duration of treatment. It is well within the skill of one skilled in the relevant art to determine effective therapeutic dosages.

Optionally, the body portion of the medial device comprises an inert agent that facilitates noninvasive detection of the implanted device. For example, barium sulfate and platinum oxide can be used to allow detection of the device by x-ray or fluoroscopy. Alternatively, the surface of the body portion of the device can be made echogenic (see, e.g., Bosley, U.S. Pat. No. 5,289,831; Bosley et al., U.S. Pat. No. 5,201,314; Bosley et al., U.S. Pat. No. 5,081,997; and Rammler, U.S. Pat. No. 5,327,891) to enhance ultrasound imaging. For example, an echogenic material such as zinc oxide, iron oxide, or titanium oxide can be incorporated into the body portion of the device to make it ultrasound visible.

A sufficient amount of a biostable polymer must be included to impart to the body portion of the device the desired characteristics, such as tensile strength and durometer flexibility. For example, where silicone is used, the body portion of the device preferably comprises about 43 wt-% to about 57 wt-% silicone. In a particularly preferred embodiment, the body portion of the medical device comprises about 50 wt-% to about 55 wt-% medical grade silicone, about 50 wt-% to about 45 wt-% barium sulfate, and about 0.1 wt-% to about 1.5 wt-% therapeutic agent, preferably dexamethasone.

The invention is described herein with particular reference to prosthetic heart valves, annuloplasty rings, and grafts, more particularly with respect to medical devices that include sewing rings having silicone or polyurethane inserts and polyester fabric encasements. Nonetheless, it is to be understood that the invention is generally applicable to any implantable medical device, additionally including, for example, stents, medical leads, catheters, and pacemakers, that can include a fabric overlayer of any type, including for example a sheath, an encasement, a layer, or a coating, such that the fabric overlayer is in contact with body tissue or fluids such as blood.

For example, FIG. 1(a) is a simplified schematic view of an implanted medical device 200 embodying the present invention. Pacing and sensing lead 218 is attached to an hermetically sealed enclosure 214 and implanted near human heart 316. Implantable medical device 200 is encased in a polyester pouch 201; and the body (212, 214) of implantable medical device 200 contains an elutable anti-inflammatory drug such as dexamethasone. In the case where implanted medical device 200 is a pacemaker it includes at least one or both of pacing and sensing leads 216 and 218. Pacing and sensing leads 216 and 218 sense electrical signals attendant to the depolarization and repolarization of the heart 316, and provide pacing pulses for causing depolarization of cardiac tissue in the vicinity of the distal ends thereof. Implantable medical device 200 may be an implantable cardiac pacemaker such as those disclosed in U.S. Pat. No. 5,158,078 to Bennett et al, U.S. Pat. No. 5,312,453 to Shelton et al, or U.S. Pat. No. 5,144,949 to Olson, all hereby incorporated herein by reference in their respective entireties.

Implantable medical device 200 may also be a PCD (Pacemaker-Cardioverter-Defibrillator) corresponding to any of the various commercially available implantable PCDs, with the substitution of pacing or sensing leads connector module 212 of the present invention for the connector block assembly otherwise present. The present invention may be practiced in conjunction with PCDs such as those disclosed in U.S. Pat. No. 5,545,186 to Olson et al., U.S. Pat. No. 5,354,316 to Keimel, U.S. Pat. No. 5,314,430 to Bardy, U.S. Pat. No. 5,131,388 to Pless or U.S. Pat. No. 4,821,723 to Baker et al., all hereby incorporated herein by reference in their respective entireties. Those devices may be employed directly in conjunction with the present invention, and most preferably are practiced such that the feedthroughs interconnecting the circuitry therein to their connector blocks is located to permit ready access between the feedthroughs and the electrical connectors disposed within the connector bores of connector or header module 212.

Alternatively, implantable medical device 200 may be an implantable nerve stimulator or muscle stimulator such as that disclosed in U.S. Pat. No. 5,199,428 to Obel et al., U.S. Pat. No. 5,207,218 to Carpentier et al. or U.S. Pat. No. 5,330,507 to Schwartz, or an implantable monitoring device such as that disclosed in U.S. Pat. No. 5,331,966 issued to Bennet et al., all of which are hereby incorporated by reference herein in their respective entireties. The present invention is believed to find wide application to any form of implantable electrical device for use in conjunction with electrical leads, and is believed to be particularly advantageous in those contexts where multiple medical electrical leads are employed and desired.

In general, hermetically sealed enclosure 214 includes an electrochemical cell such as a lithium battery, circuitry that controls device operations and records arrhythmic EGM episodes, and a telemetry transceiver antenna and circuit that receives downlink telemetry commands from and transmits stored data in a telemetry uplink to the external programmer. The circuitry and memory may be implemented in discrete logic or a micro-computer based system with A/D conversion of sampled EGM amplitude values. The particular electronic features and operations of the implantable medical device are not believed to be of overriding significance in respect of practicing the present invention. One exemplary operating system is described in commonly assigned, co-pending U.S. patent application Ser. No. 08/678,219, filed Jul. 11, 1996, for "Minimally Invasive Implantable Device for Monitoring Physiologic Events," the disclosure of which is hereby incorporated by reference herein in its entirety.

It is to be understood that the present invention is not limited in scope to either single-sensor or dual-sensor pacemakers, and that other sensors besides activity and pressure sensors could be used in practicing the present invention. Nor is the present invention limited in scope to single-chamber pacemakers. The present invention may also be practiced in connection with multiple-chamber (e.g., dual-chamber) pacemakers.

Figure 1B:
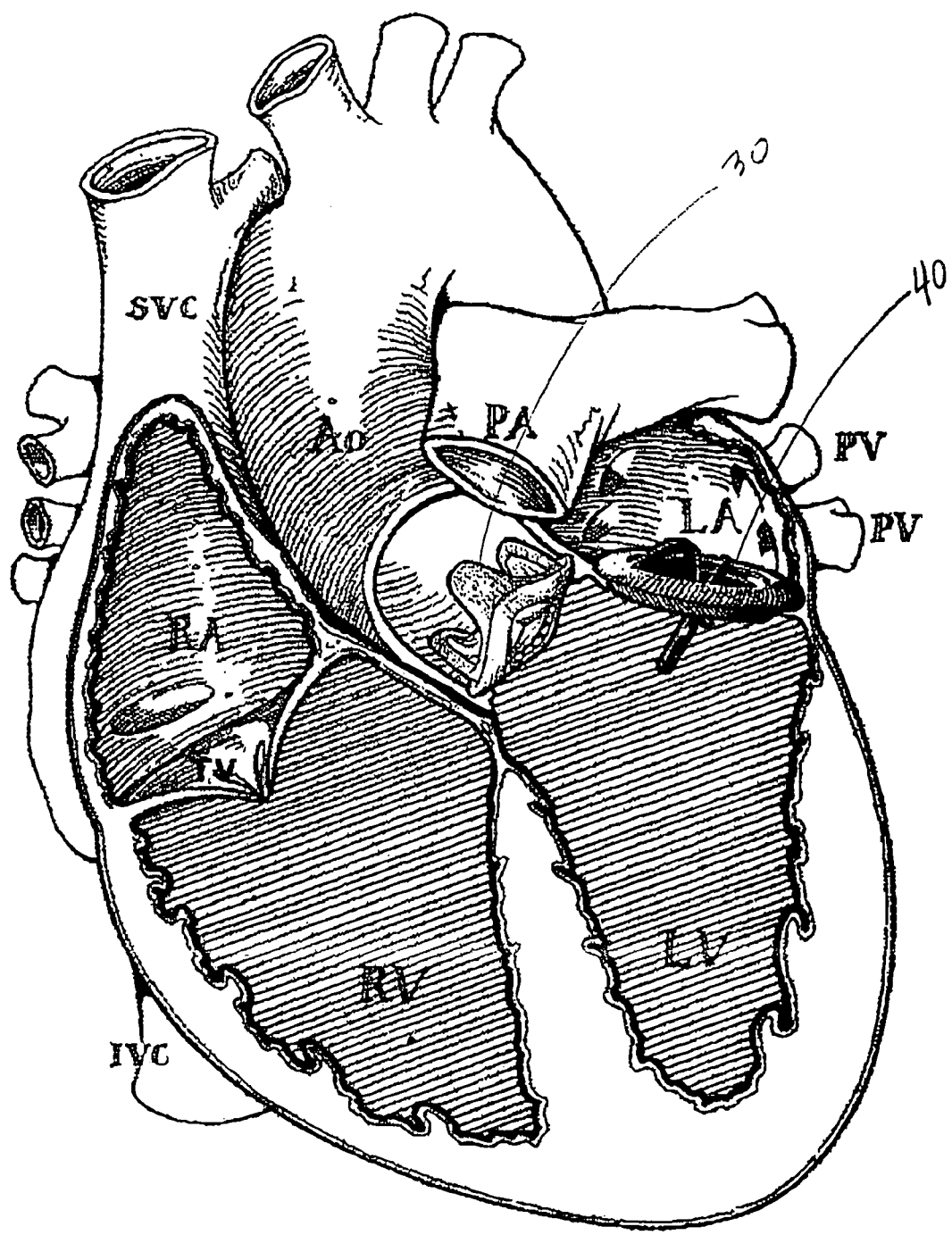

FIG. 1(b) is a simplified schematic view of implanted mechanical and bioprosthetic heart valves embodying the present invention. The bioprosthetic valve apparatus 30 is shown here as replacing the aortic valve, and the mechanical valve 40 is shown here as replacing the mitral valve.

Figure 2:
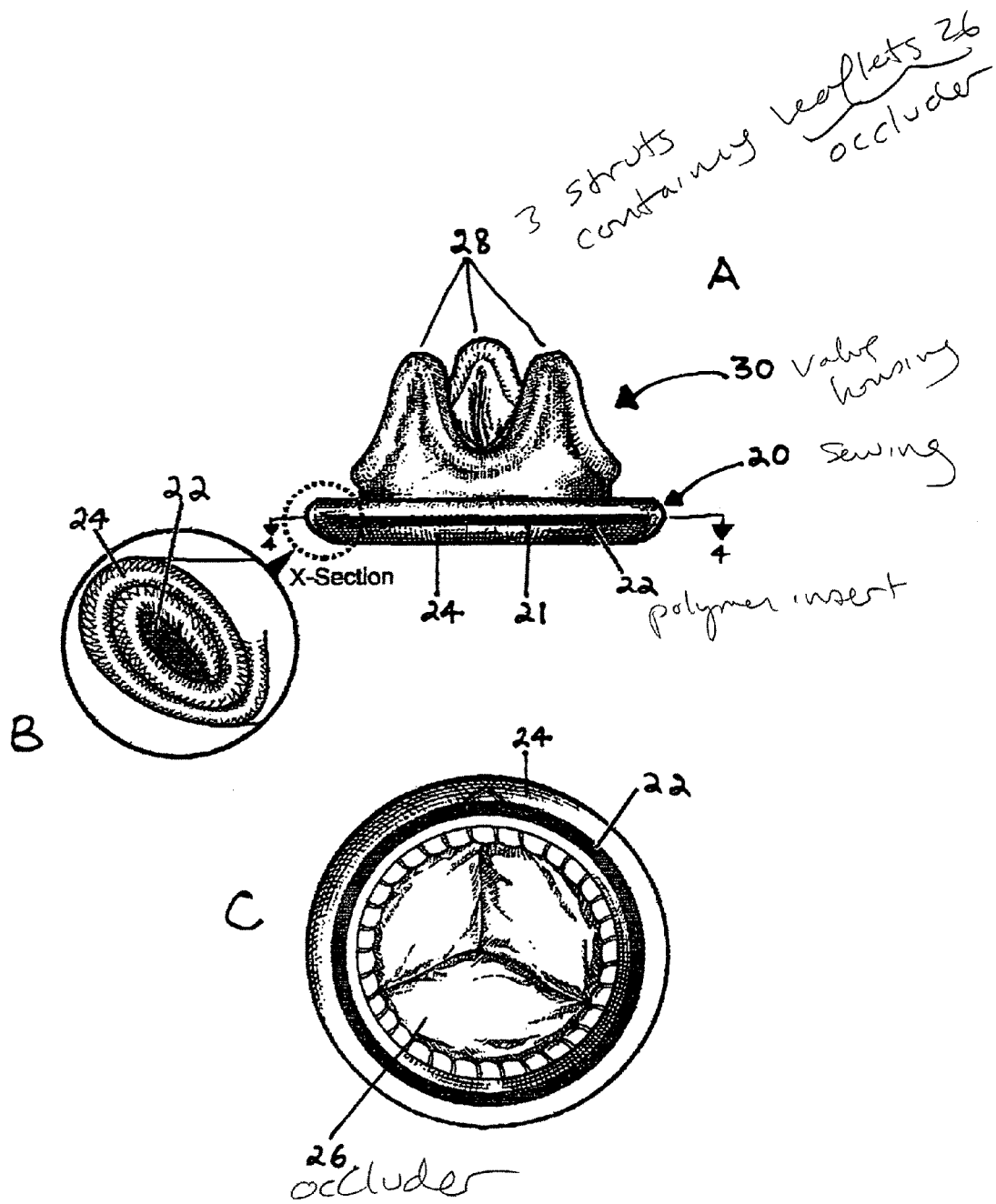
FIG. 2 shows a bioprosthetic heart valve: (a) plan view, (b) section along line 4-4 of (a); and (c) superior view of the valve.

FIG. 2 is a more detailed illustration of a bioprosthetic heart valve embodying the present invention. Bioprosthetic valve 30 contains three tissue leaflets 26, which together function as a flow occluder. The valve housing 32 is composed of a fabric-covered polymeric scaffolding having three struts 28 to which the leaflets 26 are attached. A sewing ring 20 is attached circumferentially, via suturing, to the base of the valve housing 32. Sewing ring 20 is fabricated from a cloth-like sheath or mesh 24 that forms a lumen 21 containing an annular polymeric support frame 22, referred to herein as a polymer insert. The sheath 24 is typically polyester cloth, such as Dacron™, and is made by folding a cloth sheet around polymer insert 22 and sewing the folded ends together. The combination of the polymer insert 22 and sheath 24 result in a sewing ring 20 which is completely flexible yet essentially nonextensible. Polymer insert 22 is typically made of radiopaque flexible silicone rubber, which allows the presence of the device to be monitored after completion of the implant surgery.

Figure 3:
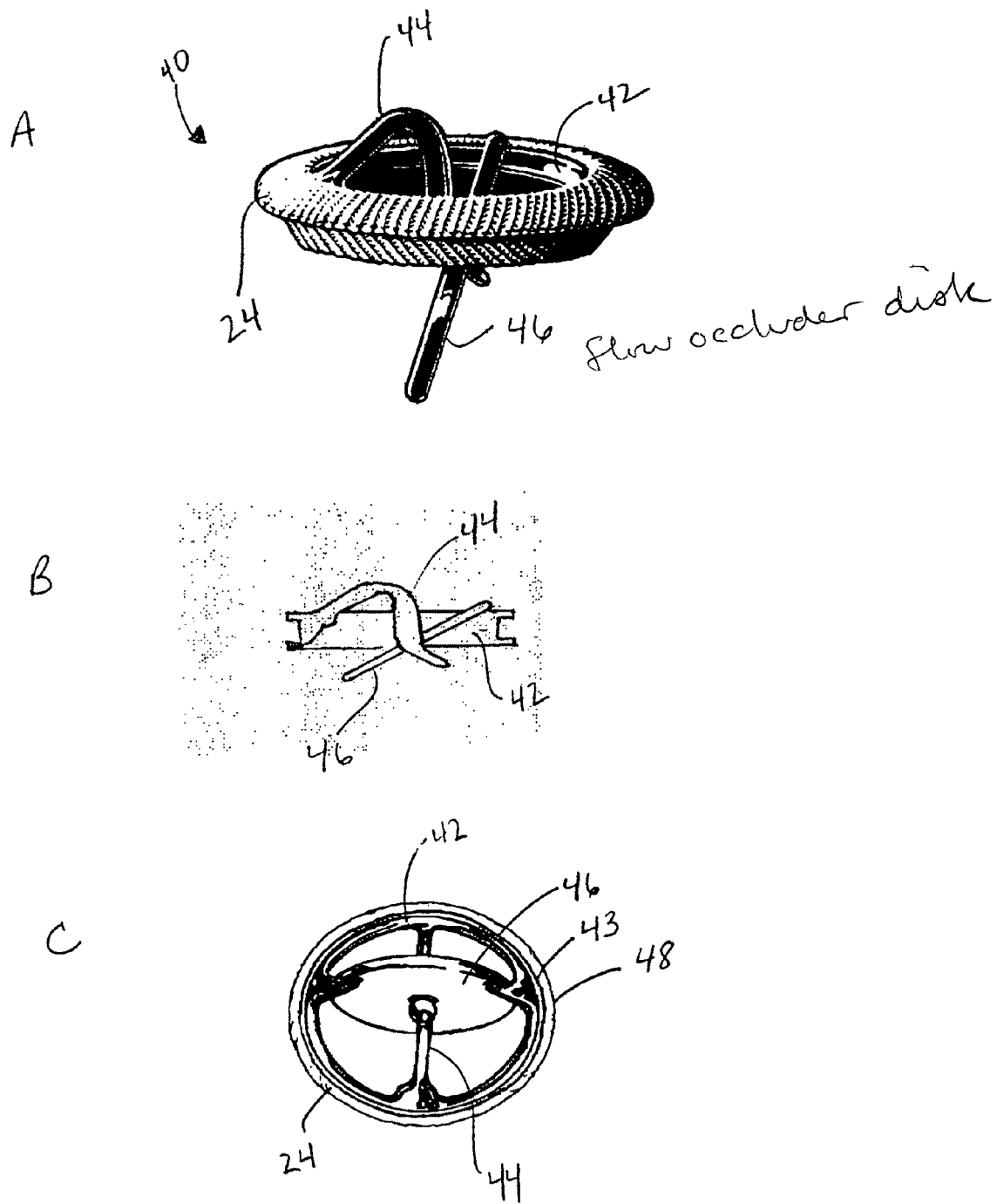
FIG. 3 is shows a mechanical heart valve: (a) valve; (b) valve without sewing ring; and (c) superior view of valve.

FIG. 3 is a more detailed illustration of a mechanical heart valve embodying the present invention. Mechanical valve 40 comprises a metallic ringed valve housing 42 containing a central metallic strut 44 along which the flow occluder disk 46 moves. Cloth-like sheath 24 encloses insert 43 (shown as a line in FIG. 3(c)) to form sewing ring 48 which is attached to the valve housing 42.

Figure 4:
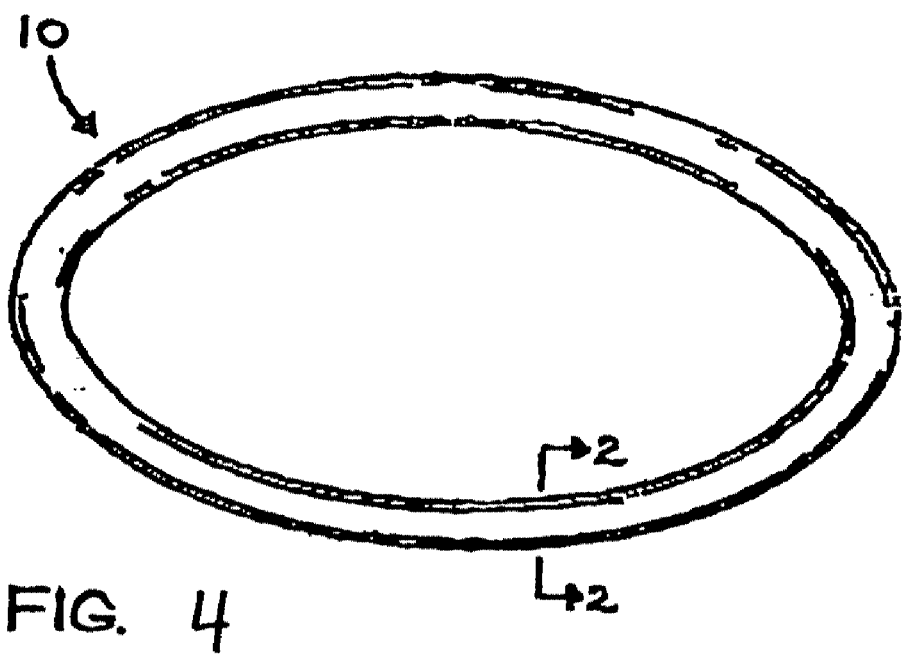
FIG. 4 is a plan view of an annuloplasty ring.
Figure 5:
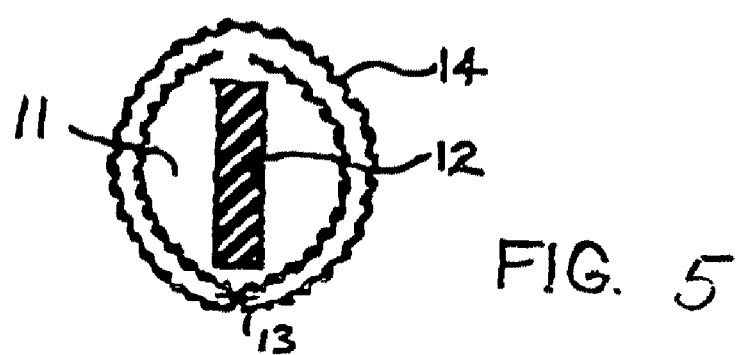
FIG. 5 is a section along line 2-2 of FIG. 4.

Sewing rings inserts for bioprosthetic or mechanical valves are typically fabricated from one or more of a polymer, preferably silicone; a metal, preferably titanium or tantalum; a metal alloy, preferably titanium alloys, cobalt chrome alloys, nickel chrome alloys, or stainless steels; or combinations thereof. They are used for shaping and/or structural support of the implanted device, surrounded by or encased in a cloth-type material that can be sutured. The insert can be pliable or rigid, can vary in physical dimensions depending on the device, and is commonly enclosed with polyester fabric FIGS. 4 and 5 illustrate a conventional annuloplasty ring (a Duran ring) embodying the present invention. Ring 10 has a lumen 11 containing a generally rectangular inner core 12 of radiopaque silicone rubber which is radially completely flexible. The core 12 is completely enclosed by a sheath 14 of polyester cloth, such as Dacron™. The sheath 14 is made by folding a cloth sheet around the core 12 and sewing the folded ends together at 13. The combination of the core 12 and sheath 14 result in a ring which is completely flexible yet essentially nonextensible. This property allows the annuloplasty ring or band, when implanted in the heart, to prevent the valve annulus from becoming distended, without significantly impeding the natural motion of the annulus. The ring 10 has three trigone markers 15 sewn thereon at 120° intervals to assist the surgeon in the placement of sutures.

Another example of the implantable medical device of the invention is an implantable drug infusion device, such as the SynchroMed® pump (Medtronic Inc., Minneapolis, Minn.), which is encased in a polyester pouch. The SynrchoMed® pump is designed for delivery of the drugs, such as baclofen or morphine, directly to the fluid of the spinal cord, by injecting them to the intrathecal space. The pump is typically surgically implanted just under the skin of the abdomen, and comprises a round metal disk about 2.5 cm thick and about 7.5 cm across. The drug is injected through a small-diameter catheter that is inserted into the spinal fluid surrounding the spinal cord. In accordance with the present invention, the pump is encased in a polyester pouch, and a therapeutic agent, preferably an anti-inflammatory agent, is coated or adhered to the surface of the metal disk, such that the therapeutic agent is capable of eluting through the pouch. An implantable drug infusion device according to the invention having a body portion comprising an elutable anti-inflammatory agent is expected to be much easier to explant, as the chronic inflammatory response responsible for fibrous tissue formation is abated.

Fabric Overlayer.

The porous "overlayer" of the implantable medical device is fabricated from a knitted or woven fabric which promotes tissue ingrowth. Preferably, the fabric is a knitted or woven fabric of polymeric fibers, although it can be fashioned from nonpolymer fibers as well. A cloth-like material is preferred for devices that are implanted using suturing techniques. Examples of polymeric fibers that can be knit or woven into a porous fabric included natural polymers such as collagen, silk, chitin, cellulose and synthetic polymers such as polyesters, polyamides, polyurethanes, polypropylenes, polyethyleneteraphthalates (PETs), poly(tetrafluoroethylene)s (PTFEs), polyethylenes, poly(vinyl alcohol)s, polyacrylonitriles, poly(glycolic acid)s, poly(lactic acid)s, polydimethylsiloxanes, aramids, and regenerated celluloses. Preferably, the porous polymeric material is a knitted or woven fabric of PET fibers. A fabric fashioned from expanded PTFE fibers, which are made using a heating and mechanical stretching process (D. Willkerson et al., "Biomaterials Used in Peripheral Vascular Surgery," R. Greco, Ed., *Implantation Biology: The Host Responses and Biomedical Devices,* 179-190, CRC Press Inc., (1994)) can also be used; a fabric made from expanded PTFE fibers has improved handling characteristics and exhibits less fraying at the suture lines than conventional PTFE fabrics.

The porous fabric overlayer is not limited to a particular structural form, and can, for example, be a sheath, an encasement, an enclosure, a sheet, a layer, a film or a coating. Preferably, the fabric overlayer has strong to fairly high tensile strength, is flexible, possesses a rough neointima inducing surface, is easily penetrable to sutures, and is tear resistant to needle penetration and sutures, and is biocompatible.

Body Portion.

As used herein, the term "body portion" of an implantable medical device refers to the portion of the implantable medical device that is covered, encased or overlaid by the fabric overlayer. In other words, the device optionally includes other structures or portions that are not covered by fabric.

The body portion of an implantable medical device of the invention can be fabricated from any desired constituent material or materials, without limitation. Preferably, the constituent material of the body portion of the device is biocompatible. The choice of constituent material will depend on the intended structure and function of the device. In embodiments of the device intended for long-term use, such as stents, heart valves, annuloplasty rings, and pacemakers, it is preferred that the body portion of the device be formed from a biostable material, such as a biostable metal or polymer. Preferably, the material forming the body portion of the device is not intended for tissue in-growth, in contrast to the fabric encasing it. The implantable device of the invention is typically intended to be in contact with bodily tissues or fluids for extended periods of time (e.g., days, months, years). Examples of biostable polymers suitable for use as materials to form the body portion of the device include polyurethanes, such as polyether urethane, silicones; polyamides, such as nylon-66; polyimides; polycarbonates; polyethers; polyesters, such as polyethylene terephthalate; polyvinyl aromatics, such as polystyrenes; polytetrafluoroethylenes and other classes of fluoropolymers such as poly(ethylene-chloro-trifluoroethylene), poly(ethylene-tetrafluoroethylene), poly(chloro-trifluoroethylene), fluorinated ethylene-propylene copolymers, perfluoroalkoxy copolymers and fluoroelastomers; polyolefins, such as polyethylenes, polypropylenes, polyisoprenes, and ethylene-alpha olefin copolymers; acrylic polymers and copolymers; vinyl halide polymers and copolymers, such as polyvinyl chloride; polyvinyl ethers, such as polyvinyl methyl ether; polyvinyl esters, such as polyvinyl acetate; polyvinyl ketones; polyvinylidine halides, such as polyvinylidene fluoride and polyvinylidene chloride; polyacrylonitrile; as well as copolymers of vinyl monomers with each other and olefins, such as ethylene-methyl methacrylate copolymers, acrylonitrile-styrene copolymers, acrylonitrile butadiene styrene (ABS) resins, polysulfones, polyetherimides, polyetheretherketones, polyarylketones, epoxy resins, liquid crystalline polymers, polyphenylene sulfides, polyphenylene oxides, polyamideimides, polyacetals, polyketones, polyarylates, ethylene-vinyl acetate copolymers, and blends of the afore-mentioned. Polyurethanes and silicones, or combinations thereof, are presently the preferred polymeric substrates in the context of this invention. Preferably, the body portion of an implantable device of the invention is fabricated from silicone, polyurethane, or a combination thereof.

It should nonetheless be understood that it is well within the scope of the invention to include devices having body portions fabricated from biodegradable or resorbable materials instead of or in addition to biostable materials, as required by a particular application, such as those for short-term treatment or therapy. Biodegradable polymers suited for use in the body portion of the device include poly(lactic acid)s, poly (glycolic acid)s, poly(lactic-co-glycolic acid)s, polyanhydrides, poly(orthoester)s, poly(hydroxybutyrate)s, poly(hydroxyvalerate)s, polydioxanones, polyphosphazone, polycaprolactones, polyaminoacids, and collagen. Where biodegradable polymer are used to contain the therapeutic agent, it is not necessary that the therapeutic agent elute from the polymer; the therapeutic agent can, instead, be released from the polymer as a consequence of biodegradation.

Drug-Loading of the Body Portion.

The constituent material of the body portion of an implantable medical device of the invention is in intimate contact with one or more therapeutic agents (also referred to herein as simply "drugs"), and the body portion is fabricated such that the therapeutic agent can elute away from its surface and ultimately through the porous fabric overlayer. The therapeutic agent can be incorporated into the body portion of the implantable medical device in a variety of ways. For example, the therapeutic agent can be covalently grafted to a surface of the body portion of the device, either alone or with a surface graft polymer. Alternatively, it can be coated onto the surface of the body portion of the device either alone or intermixed with an overcoating polymer. It can also be mixed with an adhesive, such as a silicone adhesive, and applied to the surface of the body portion of the device, after which the fabric overlayer can, if desired, be adhered to the body portion of the device. It can be physically blended with a polymer of the body portion of the device as in a solid-solid solution. It can be impregnated into the polymer by swelling the polymer in a solution of the appropriate solvent, or imbibed into a porous metal body portion. A polymer containing a therapeutic agent can be extruded, molded, or coated on another material (e.g., metal), grafted onto another material, embedded within or compounded into another material, adsorbed to another material, etc., to form the body portion of the device. Any means by which the therapeutic agent can be incorporated into the medical device such that it is in intimate contact with a constituent material of the body portion of the device are within the scope of the present invention.

In one embodiment, a polymer of the body portion of the device and a therapeutic agent are intimately mixed either by blending or using a solvent in which they are both soluble (e.g., xylene for silicone and dexamethasone phosphate). This mixture can then be formed into the desired shape and incorporated into the medical device or coated onto an underlying structure of the medical device.

Alternatively, a coating polymer, which may or may not be the same polymer that forms a primary polymer of a body portion of the device, and a therapeutic agent are intimately mixed, either by blending or using a solvent in which they are both soluble, and coated onto the body portion of the device. The coating polymers are preferably any of the biostable polymers listed above, as long as they are able to bond (either chemically or physically) to the polymer of the body portion of the device. Alternatively, however, they can be any of a wide variety of bioabsorbable polymers, as long as they are able to bond (either chemically or physically) to the polymer of the body portion of the device. Examples of suitable bioabsorbable polymers include poly(L-lactic acid), polycaprolactone, poly(lactide-co-glycolide), poly(hydroxybutyrate), poly(hydroxybutyrate-co-valerate), and others as disclosed in U.S. Pat. No. 5,679,400 (Tuch). Additionally, a coating on the surface of the body portion of the device can be used, for example, to control drug release rates from the body portion of the device.

Yet another embodiment includes swelling the polymer of a body portion of the device with an appropriate solvent and allowing the anti-inflammatory agent to impregnate the polymer. For example, for polyurethane, tetrahydrofuran, N-methyl-2-pyrrolidone, and/or chloroform can be used.

In another embodiment, a therapeutic agent is covalently grafted onto the polymer of a body portion of the device. This can be done with or without a surface graft polymer. Surface grafting can be initiated by corona discharge, UV irradiation, and ionizing radiation. Alternatively, the ceric ion method, previously disclosed in U.S. Pat. No. 5,229,172 (Cahalan et al.), can be used to initiate surface grafting.

Accordingly, a drug-containing polymer can be extruded, molded, or coated on another material (e.g., metal), grafted onto another material, embedded within or compounded into another material, adsorbed to another material, etc., to form the body portion of the device. It should be noted that herein, when a secondary coating polymer, surface graft polymer, or the like is used, the body portion of the device is defined to include this secondary polymer as well as the primary polymer that forms the basic structure of the medical device (e.g., the sewing ring insert or the vascular graft). Likewise, the body portion of the implantable device can be a layered composite structure. For purposes of the invention, it is important only that the body portion of the device, however fashioned, contain a therapeutic agent, and the therapeutic agent is capable of eluting from, diffusing away from, or otherwise being released from the body portion of the device, so as to then elute through the porous fabric overlayer of the device.

Notwithstanding the preceding, however, a therapeutic agent is preferably bulk loaded into the body portion of the device, such as a silicone insert, at the time of manufacturing. Efficacy of the loaded drug on the host inflammatory response is dependent on the rate of drug elution from the insert and through the porous fabric. Preferably the drug release profile of an implantable medical device of the invention extends over at least about 30 days.

Therapeutic Agents

Suitable anti-inflammatory agents for use in the present invention include both steroidal and nonsteroidal compounds. Preferably, the steroidal anti-inflammatory agents include glucocorticoids, salts, and derivatives thereof. Examples of such steroids include cortisol, cortisone, fludrocortisone, prednisone, prednisolone, 6α-methylprednisolone, triamcinolone, betamethasone, dexamethasone, beclomethasone, aclomethasone, amcinonide, clebethasol, clocortolone. Dexamethasone (9α-fluoro-11β,17α,21-trihydroxy-16α-methylpregna-1,4-diene-3,20-dione), derivatives thereof, and salts thereof are particularly preferred. Dexamethasone sodium phosphate and dexamethasone acetate are suitable salts and dexamethasone-21-orthophosphate and its disodium salt are suitable derivatives. Nonsteroidal anti-inflammatory drugs include gold thiomalate, gold thiosulfate, auranofin, D-penicilamine, and Cox-2 inhibitors such as rofecoxib (Vioxx™, Dupont Merck) and celecoxib (Celebrex™, Pfizer).

The anti-inflammatory agent can be used in any amount that produces the desired response without detrimental effects, such as cytotoxic effects or the suppression of the immune response. Typically, it is used in an amount or dosage appropriate for the desired duration and intensity of the anti-inflammatory effect. Ultimately, this is dictated by the type of device to which this invention is applied. Generally, it is believed, however, that less than about 1 mg of an anti-inflammatory agent per square centimeter of surface area of a polymer-contacting surface can be used to produce the advantageous results described herein.

Other therapeutic agents include antibacterial or antimicrobial agents, anticoagulant agents, antithrombotic agents, antiplatelet agents, antimitotic agents, antiseptics, antioxidants, antimetabolite agents, antiproliferative agents, anticalcification agents, anti-thrombogenic agents, chelating agents, enzymes, catalysts, hormones, growth factors, lectins, vitamins, antibodies, antigens, nucleic acids such as DNA and RNA, proteins or peptides, polysaccharides, dyes, radioactive compounds, or any combination thereof. A preferred therapeutic agent is heparin. Preferably, the heparin is included in an amount effective to prevent or limit thrombosis. Heparin can be incorporated into the body portion of the device by coating, covalently bonding, or any of a variety of well-known techniques for incorporating heparin into a medical device. In one embodiment, heparin is covalently bonded to the body portion of a device which also contains an elutable anti-inflammatory agent.

Antimicrobial agents include aminoglycosides, such as gentamicin, kanamycin, neomycin, paromomycin, streptomycin and tobramycin, ansamycins such as rifamycin and rifampin, cephalosporins such as cehpalexin, cephaloridine, cephalothin, cefazolin, cephapirin, cephradine, and cephaloglycin, macrolides such as erythromycin, tylosin, oleandomycin and spiramycin, penicillins such as penicillin G, penicillin V, phenethicillin, methicillin, oxacillin, cloxacillin, dicloxacillin, floxacillin, nafcillin, ampicillin, amoxicillin, and carbenicillin, sulfonamides, chloramphenicols, tetracyclines such as tetracycline, oxytetracycline, chlortetracycline, methacycline, demeclocycline, rolitetracycline, doxycycline, and minocycline, polypeptides such as bacitracin, polymixins, tyrothricin and vancomycin, and others including trimethoprim-sulfamethoxazole, lincomycin, clindamycin and spectinomycin. Particularly preferred antimicrobial agents include rifampicin and gentamicin. Antiseptic agents include silver, chlorohexidine, irgasan, iodine and quaternary ammonium compounds such as benzalkonium chloride. Other examples of therapeutic agents include cytostatic drugs such as amethopterin, vincristine sulfate, an vinblastine sulfate; immunosuppressive agents such as cyclosporine A and azathioprine, anti-cell adhesion molecules (anit-CAMs), such as lactose-1-phosphate and anti-integrin antibodies, antioxidants such as ascorbic acid and α-tocopherol, and others such as pentoxyfilline and cytochalasin B. Standard dosages and administration protocols can be found, for example, in the Merck Index, 12$^{th}$ Ed. (Merck Research Laboratories, Merck & Co., Inc., Whitehouse Station, NJ, (1996)), the Physician's Desk Reference, 52$^{nd}$ Ed. (Medical Economics Company, Inc., Montrale, NJ, (1998)), or the Manual of Medical Therapeutics/Department of Medicine, Washington University School of Medicine, 28$^{th}$ Ed. (G. A. Ewald et al., Eds., Little, Brown Press, Boston (1995)).

EXAMPLES

The following examples are intended for illustration purposes only. All percentages are by weight unless otherwise specified.

Example 1

In vitro Biological Oxidation and Environmental Stress Cracking in Polyetherurethane A. Materials and Methods 1. Cell Isolation Human and rabbit blood was used as sources of the cells in these experiments. Blood was anticoagulated with 2 units/ml sodium heparin (Upjohn Co., Kalamazoo, MI). Mononuclear cells (lymphocytes, monocytes) were isolated within 15 minutes by a one-step density gradient centrifugation procedure using Isopaque-1077 (a density gradient solution) according to a modified Boyum's method (Boyum et al., *Blood Separation and Plasma Fractionation*, 217-239, Wiley-Liss, Inc. (1991)). The mononuclear cells were harvested and washed twice with cold Hanks balanced salt solution (HBSS) without $Ca^{2+}$ and $Mg^{2+}$ to minimize cell aggregation. The cells were then resuspended in standard media (RPMI-1640, 10% Fetal bovine serum, 0.2M L-glutamine, 10 Ul/ml Penicillin-G, and 0.1 mg/ml Streptomycin). The cell suspension was seeded into several plastic tissue culture flasks and incubated in the presence of 5% $CO_2$ at 37° C. for 1 hour (Ackerman et al., *J. Immunol.*, 20, 1372-1374 (1978)). After this incubation, adherent (monocytes) were gently scrapped from the surface and resuspended in standard media. Nonadherent cells (lymphocytes) contained in the supernatant were recovered into sterile tubes, and the remaining nonadherent cells washed off with cold HBSS. The culture flasks were washed three times with cold HBSS, and the remaining adherent cells (monocytes) were gently scrapped from the surface and resuspended in standard media. Both cell types were resuspended to a density of $3 \times 10^6$/ml.

2. Test Materials

Polymer discs, 6 mm in diameter, 0.12±0.008 mm thick, were cut out of polyetherurethane (PEU) sheets using biopsy punches (Prestwick Line, S.M.S. Inc., Columbia, Md.). One group of polymer discs were soaked in acetone (AS) for 1 hour to extract polymer antioxidants, and dried at room temperature for 4 hours. The other group was used with no pretreatment (non-AS). Polymer specimens were then fitted to the bottom of the wells of 96-microwell cell culture plates under sterile conditions.

3. In Vitro Polymer Treatments

A 2-step in-vitro treatment was carried out at 37° C. to mimic the in-vivo environment and facilitate the biodegradation of the PEU sheets.

Macrophage Treatment. The PEU film specimens (AS and non-AS) in the microwell plates were covered with either freshly isolated human or rabbit monocyte-derived macrophage (Mo/MØs), or human lymphocytes ($3 \times 10^5$ cells per well) and cultured in a standard media (RPMI-1640, 10% Fetal bovine serum, 0.2M L-Glutamine, 10 Ul/ml Penicillin-G and 0.1 mg/ml Streptomycin). A 49-day macrophage treatment was conducted under standard conditions (i.e., presence of 5% $CO_2$, and 95% humidity at 37° C.). Other experimental variations included adding dexamethasone sodium phosphate (DSP) at 0.024 µg/ml and 240 µg/ml concentrations to the culture media in the microwells. Two blank conditions were also studied. In one, culture media only was placed into the microwells. The other was prepared with no culture media and stored in the dark. All polymer specimens were incubated for the time of the first treatment. Samples in triplicate were removed after various time periods for hydroperoxide determination. After a 49-day incubation, specimens were prepared in triplicate for the second step of the sample treatment protocol.

$FeCl_2$ treatment. Following the 49-day treatment with macrophages, specimens were folded in half and fixed in this position by heat sealing the two opposite ends in such a fashion that an area of increased stress in the central region of the specimens. This design permitted a characterization of unstrained and moderately strained polymer states. Stressed specimens were incubated in 5 mM $FeCl_2$ at 37° C. for 10 days. Optical microscope (OM) evaluation of the samples was performed during the treatment. Triplicate samples for each condition were taken after 10-day treatment for scanning electron microscope (SEM) evaluation of the polymer surface.

4. Iodometry

Polymer specimens taken at various time periods during the macrophage treatment step were sonicated for 15 minutes in distilled water, rinsed three times, and dried at 25° C. for 4 hours. Hydroperoxide (ROOH) determination using an iodometric assay was performed as described by Fujimoto et al., *J. Polym. Chem.*, 31, 1035-1043 (1993). This method is based on the reactivity of the hydroperoxide group, which oxidizes iodide to iodine. The resulting triiodide complex ($I_3^-$) was measured spectrophotometrically at 360 nm λ with a Beckman DU-8 spectrophotometer (Beckman Instruments, Irvine, Calif.). This method measures the total (surface plus bulk) hydroperoxide concentration in the polymer.

5. Cell Morphology and Surface Analysis

The polymer films (0.12 mm thick) were sufficiently thin and transparent to enable visualization of cells on their surfaces during cell culturing using optical microscopy (OM) with an Olympus BX40 light microscope. For SEM cell morphology evaluation, specimens were taken after 21 days of macrophage cell culture. They were prepared for SEM evaluation by placing them into a cold fixative solution containing "PLASMA-LYTE" A (isotonic solution from Baxter Scientific, IL) and 1.5% glutaraldehyde. They were then stored at 4° C. for 48 hours. The samples were then removed from the glutaraldehyde fixative, rinsed in "PLASMA-LYTE" A three times for 15 minutes each. Following this, they were post-fixed with Palade's fixative (4% solution osmium tetroxide, Polysciences, Warrington, PA) for 2 hours. Following post-fixation, the samples were rinsed in "PLASMA-LYTE" A three times for 10 minutes each, and then slowly dehydrated using increasing concentrations of ethanol. They were finally critically point dried using $CO_2$. The polymer surfaces were also evaluated using SEM following the 10-day treatment with $FeCl_2$. All SEM specimens were mounted and sputter coated with gold-palladium for 2 minutes at 10 mA (≈100 Angstroms coating thickness), using a Humme IV Sputterer Coater (Anatech, Alexandria. VA). Observation at different magnifications was done with a Stereoscan 360 (Cambridge Instruments) scanning electron microscope.

B. Results

1. Morphology of Mo/MØ Monolayers

The morphologic changes in the cell monolayer during the macrophage treatment step on the different surfaces were studied using OM and SEM analysis. Using OM analysis, early during culture, cells in the standard media started increasing their size, which continued to increase over time. The Mo/MØ monolayers in the standard media showed a variety of shapes, morphologies, and degrees of cytoplasmic spreading. The morphological changes that occurred between 0 and 33 days in these cells were extensive—increased size, cytoplasmic spreading, unusual shapes assumed with 60 μm diameter along the larger axis. A decrease in the number of cells was observed over time in the standard culture media. Mo/MØ monolayers cultured with DSP showed no increase in cell size; however, a few cells were observed to develop morphology similar to those cultured with standard media.

SEM analysis of 21-day cultured cells (standard media) showed a high degree of cell attachment and spreading of Mo/MØs on PEU. Cells were usually hemispherical with a central nucleus and extensive membrane ruffles indicating cellular activation. The dimensions of the cells varied between 25 μm and 60 μm depending on the degree and eccentricity of the spreading. In contrast, Mo/MØs cultured in the presence of 0.024 μg/ml DSP showed a smaller degree of cell spreading. The latter cells also showed numerous cytoplasmic processes (membrane prolongations). The nuclei of these cells tended to be fairly hemispherical, while the cells' surfaces, which often included protrusions, adopted a variety of shapes. These cells were highly variable in size, but were usually less than 35 μm along their larger axis. Other test conditions—human Mo/MØs cultured in the presence of 240 μg/ml DSP and human lymphocytes cultured in standard media in which a viable cell monolayer was observed under OM—showed no cells on the polymer surface when evaluated with SEM.

2. Polymer Hydroperoxide Evaluation

Figure 6:
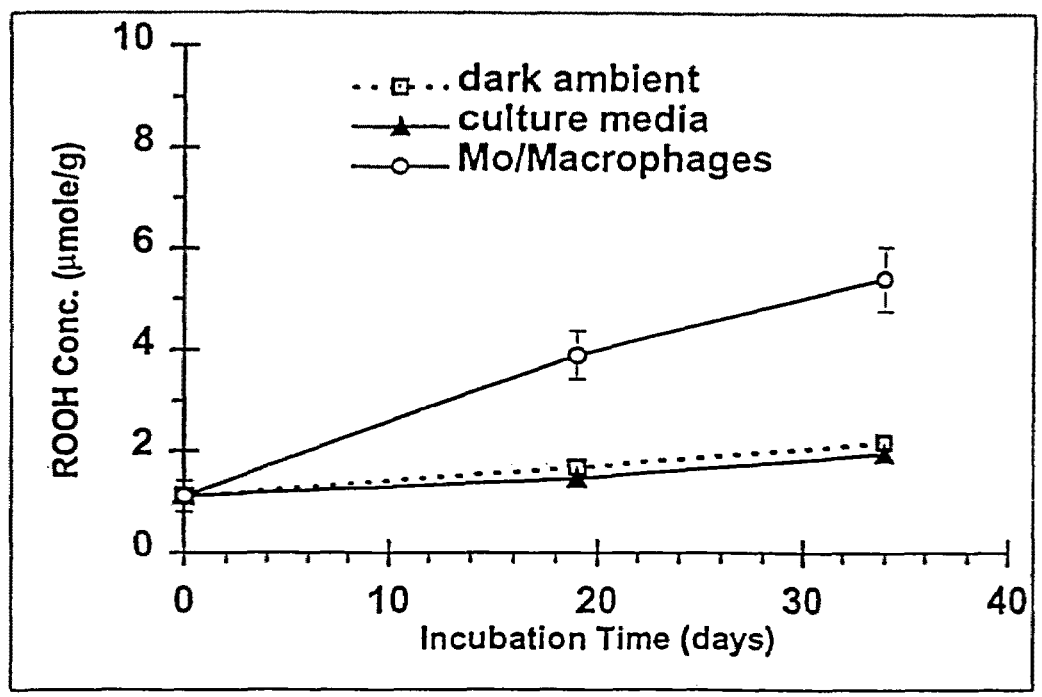
FIG. 6 is a graph showing in vitro hydroperoxide formation in: standard culture media (no cells) containing polyetherurethane specimens (presoaked in acetone "AS"); polyetherurethane (AS) specimens stored in the dark under ambient conditions; and standard culture media with rabbit Mo/MØs containing polyetherurethane (AS) specimens.
Figure 7:
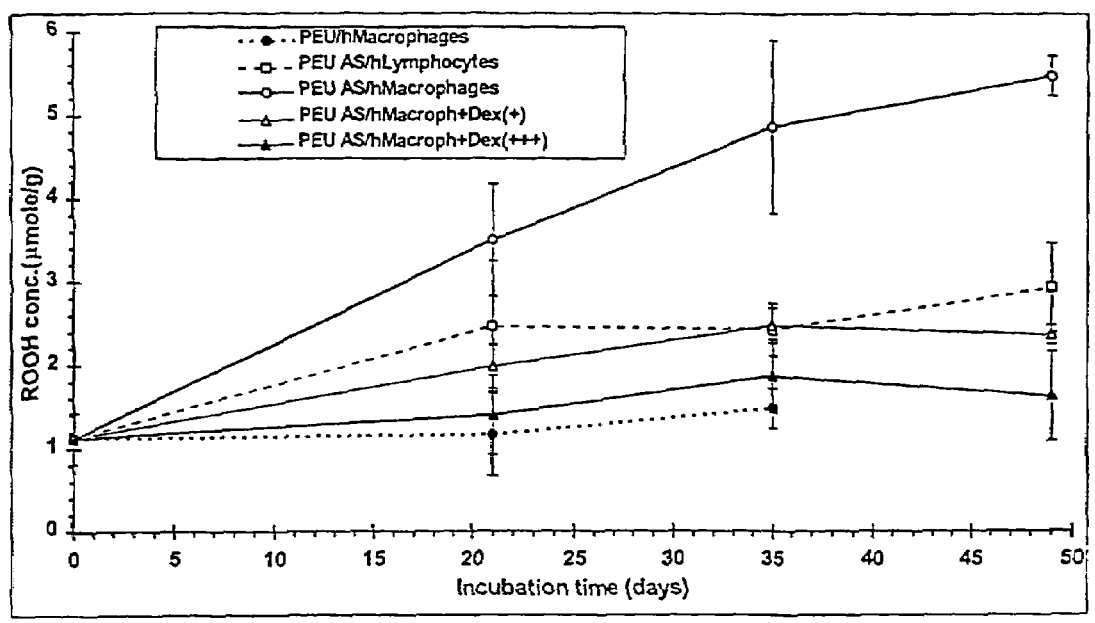
FIG. 7 is a graph showing in vitro hydroperoxide formation in: standard culture media with human Mo/MØs containing polyetherurethane specimens (with and without presoaking in acetone); standard culture media with human lymphocytes containing polyetherurethane (AS) specimens; and standard culture media with human Mo/MØs containing polyetherurethane (AS) specimens plus dexamethasone sodium phosphate at 0.024 µg/ml (+) and 240 µg/ml (+++).

FIGS. 6 (rabbit) and 7 (human) show the hydroperoxide concentration in the polymer specimens treated under the different conditions described above. These conditions included: (1) standard culture media only (no cells); (2) polymer specimen stored in the dark under ambient conditions (without culture media); (3) human and rabbit Mo/MØs in standard culture media; (4) human lymphocytes in standard culture media; and (5) human Mo/MØs in standard culture media plus DSP at 0.024 and 240 μg/ml.

The data shows an increased hydroperoxide concentration as a function of culture time and the presence of Mo/MØs. This effect was marked in AS specimens (polymer specimens soaked in acetone before treatment) cultured with Mo/MØs from either source (rabbit or human) in standard media. By contrast, AS specimens cultured with lymphocytes or Mo/MØs in the presence of DSP showed significantly lower hydroperoxide concentrations. This was comparable to levels of hydroperoxide concentration in specimens incubated in culture media only and the ones stored in the dark under ambient conditions. Likewise, non-AS polymer specimens (not soaked in acetone before treatment) cultured with Mo/MØs showed the lowest amount of hydroperoxides.

3. Surface Analysis (SEM)

SEM examination revealed substantial pitting and cracking in the AS PEU samples exposed to Mo/MØs, with the stressed (folded) area as the more affected surface region. In this region, cracks up to 20 μm wide had developed. The cracks first initiated in pits to adopt a fibrillar structure and later propagated perpendicular to the applied strain direction caused by the folding. In contrast, specimens cultured with lymphocytes or DSP showed no significant damage. AS PEU samples exposed to Mo/MØs followed by $FeCl_2$ showed more extensive damage. In contrast, non-AS PEU samples exposed to Mo/MØs followed by $FeCl_2$ did not show appreciable surface damage. AS PEU samples exposed to Mo/MØs plus DSP followed by $FeCl_2$ showed only very occasional pits.

C. Conclusion

This study indicates that macrophages are involved in polyetherurethane oxidation, probably by inducing hydroperoxide formation in the polymer structure. Under the influence of stress or strain, polymers with sufficient hydroperoxides degraded in the presence of $Fe^{2+}$ ions in a manner that closely resembles stress cracking observed in vivo. Likewise, a reduction in hydroperoxide formation and no later ESC development was demonstrated in macrophage-cultured PEU in the presence of DSP.

Example 2

In Vitro Modulation of Macrophage Phenotype on Dexamethasone-Loaded Polymer and its Effect on Polymer Stability in a Human Macrophage/Fe/Stress System

A. Materials and Methods

1. Test cell line; human monocyte-derived macrophages (Mo/MØ)

The in vitro method used is described in Example 1. Human venous blood was used as the source of cells, which were isolated as described in Example 1.

2. Test Materials

Dexamethasone-Loaded "PELLETHANE" 80A (DEX/Pe80AS). To prepare these materials, before extrusion, "PELLETHANE" 80A (Pe 80A, commercially available from Dow Chemical, Midland, MI) was extracted for 24 hours in a Soxhlett extractor using acetone. The purpose of this process was the removal of antioxidant from the polymer. After extraction, the material was dried under vacuum at 50° C. for 4 days. Dexamethasone USP Micronized BP/EP (Lot 78AFT, Upjohn Co.) was vacuum dried overnight at 40° C. In order to prepare materials with different dexamethasone (DEX) concentrations, the ratio of drug to polymer was varied to achieve 0.1% and 1% drug loading levels (w/w). Extrusion of 0.02-inch films was obtained at 0.1% DEX/Pe80A and 1% DEX/Pe80A) formulations.

"PELLETHANE" 80A Control (Pe80A). Using the same "PELLETHANE" 80A polymer (acetone extracted), 0.02-inch films were extruded without DEX. Extrusion conditions with and without dexamethasone were similar and were as recommended by the manufacturer.

Polymer discs, 6 mm in diameter, were cut out of the Pe80A test and control film sheets using biopsy punches. Polymer specimens (n=16 per condition) were then fitted to the bottom of the wells of 96-microwell cell culture plates under sterile conditions.

3. In vitro Polymer Treatments

A 2-step in-vitro treatment was carried out at 37° C., substantially as described in Example 1.

Macrophage Treatment. The PEU film specimens (test and controls) in the microwell plates were covered with a freshly isolated human monocyte-derived macrophage (hMo/MØs) monolayer at a density of $3 \times 10^5$ cells per well and cultured in a standard media (RPMI-1640, 10% Fetal bovine serum, 0.2M L-Glutamine, 10 Ul/ml Penicillin-G and 0.1 mg/ml Streptomycin). A 40-day macrophage treatment was conducted under standard conditions (i.e., 5% $CO_2$, 95% humidity, 37° C.). Freshly isolated hMo/MØs were added into the wells once a week. Immediately before the last cell refreshing, all wells were energically rinsed with culture media to detach and remove all cell components and remains, after which a fresh macrophage monolayer was applied. After this 40-day macrophage treatment, polymer samples were removed in triplicate for hydroperoxide determination and in quintuplicate for the-second step treatment.

$FeCl_2$ Treatment. Following the 40-day macrophage treatment, specimens prepared and treated as described in Example 1.

4. Iodometry

Polymer specimens taken after the 40-day macrophage treatment step were sonicated for 15 minutes in distilled water, rinsed three times, and dried at 25° C. for 4 hours. Hydroperoxide (ROOH) determination using an iodometric assay was performed as described in Example 1.

5. Cell Morphology and Surface Analysis

OM observation of cultured cells was performed during the macrophage treatment step. Likewise, the stressed polymer surfaces were evaluated using SEM following the 10-day treatment with $FeCl_2$. The specimens for SEM evaluation were rinsed in distilled water and dried at room temperature. All SEM specimens were mounted and sputter coated with gold-palladium for 2 minutes at 10 mA ($\approx$100 Angstoms coating thickness), using a Humme IV Sputterer Coater (Anatech, Alexandria, VA). Observation at different magnifications was done with a "STEREOSCAN" 360 (Cambridge Instruments) scanning electron microscope.

6. Kinetics of DEX Elution from DEX/PEU Test Materials

DEX release profile from 0.1% DEX/Pe80A and 1% DEX/Pe80A was determined in vitro at 37° C. in PBS. Each of the materials was run in triplicate. The procedure involved the immersion of four 15 mm diameter disks (0.3659±0.02 g) in 15 ml of phosphate buffer (Product No. P-4417, Sigma Chemical Co., St. Louis, Mo.). The average thicknesses of the disks were 0.47±0.06 mm. In a 32-day period at various timepoints, 800 µL of buffer was removed for analysis and replaced with fresh buffer to keep the elution volume constant. The aliquots were cold stored (4° C.) until analysis by HPLC.

7. HPCL Analysis

DEX was analyzed using reversed-phase chromatography and UV-visible detection. An octadecylsilane column (Product No. 07125, Tosohaas Bioseparations Specialists, Montgomeryville, Pa.) and mobile phase consisting of methanol and phosphate buffer (100 mM, pH 5.6) were chosen for this purpose. Furthermore, the flow rate (1.0 ml/minute) and use of detection wavelength, peak areas and autointegration remained constant for all experiments. From this data, a cumulative elution profile and a daily DEX elution was calculated.

8. Cytokine Analysis

In order to assess the in vitro expression of IL-1α and IL-8, human primary monocytes were incubated with various concentrations of DEX (2.5, 0.25, and 0.025 µg/ml) and methotrexate (50, 5, and 0.5 µg/ml). A higher rate of IL-1 and IL-8 inhibition was observed with these agents, with DEX having the highest levels of inhibition. The inhibition appeared to be dose- and incubation time-dependent. These results further support the anti-inflammatory ability and the effects of these agents on human macrophages.

B. Results

1. Morphology of Mo/MØ Monolayers

The morphologic changes in the cell monolayer during the macrophage treatment step on the different surfaces were studied. A 100×OM observation through a Pe80A control film showed uniform cell distribution. The morphological changes that occurred between 1 and 40 days in these cells were extensive and showed to be different for each material condition. Human Mo/MØ monolayers on the test surfaces (DEX/Pe80AS) and on control surfaces (Pe80A) at 3 days of culture evidenced little or no differences.

At later analysis, 20 days, noticeable differences were observed among the monolayers in the different surfaces. While a much higher proportion of macrophages with increased size and high degrees of cytoplasmic spreading were observed on Pe80A control material, Mo/MØs cultured on DEX/Pe80AS were observed to be roundly shaped with shorter diameters and with less density. Evaluation at 40 days of polymer treatment showed the same cell phenotype seen at 20 days, although a more marked effect, or cells with a maximum of 60 mm diameter along their larger axis on controls and up to 20 µm on test materials.

2. Polymer Hydroperoxide Evaluation

Figure 8:
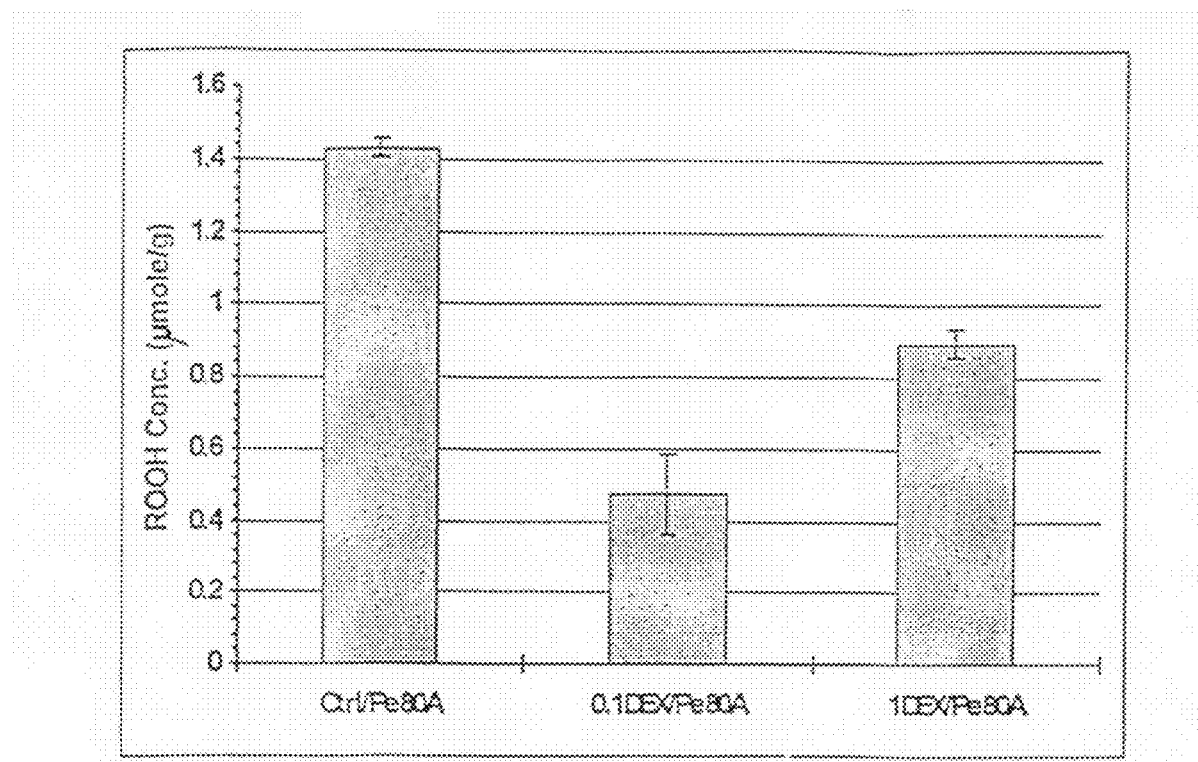
FIG. 8 is a bar chart of hydroperoxide concentration in polymer specimens with and without dexamethasone after a 40-day macrophage treatment step.

FIG. 8 shows the hydroperoxide concentration in the polymer specimens after the 40-day macrophage treatment step. The formation of ROOH in Pe80A followed a DEX-dependent effect. Significantly lower ROOH concentration in DEX/Pe80A specimens was observed. Thus, after 40 days of hMo/MØ treatment, 0.5±0.1 and 0.9±0.04 µmole ROOH/g of polymer were contained in DEX/Pe80AS (0.1% and 1% w/w, respectively). By contrast, 1.4±0.02 µmole ROOH/g of polymer was contained in the control material.

3. Surface Analysis (OM and SEM)

During the $FeCl_2$ treatment, a daily OM observation of stressed polymer specimens was conducted at 40× total magnification in an Olympus SZH10 Research Stereo Microscope (Olympus Optical Co. LTD). Noticeable surface changes were evident starting at 4 days incubation in $FeCl_2$ at 37° C. At 6 days, well-developed pits and cracks were visible in the areas of major stress in all samples of Pe80A control material. Under the same conditions of treatment, both DEX/Pe80A specimens, 0.1% and 1%, showed a shiny surface with no apparent damage. In order to expand the damage in the test samples and to induce damage in test materials, the $FeCl_2$ treatment was extended up to 10 days, after which the samples were analyzed under SEM.

SEM examination revealed substantial pitting and cracking in the Pe80A control samples, with the stressed (folded) area as the more affected surface region. In this region, cracks up to 70 µm wide had developed. The cracks first initiated in pits to adopt a fibrillar structure and later propagated perpendicular to the applied strain direction caused by the folding. By contrast, none of the DEX/Pe80A specimens showed damage; rather, a smooth surface was observed in both DEX-containing specimens.

In an attempt to obtain semiquantitative data from this evaluation, an experimental X/Y rating system was adopted. In an X/Y system, which evaluates the depth of the cracks (X) and the extension of the surface affected by environmental stress cracking (ESC) damage (Y), the product is used to compare the different test conditions. The results can range from 0 to 25, with the lowest indicating the least damage. Table 2 shows the rating of the biostability evaluation of specimens following a 40-day treatment with human Mo/MØs and 10 days with $FeCl_2$. The final rating in this experimental scoring method is expressed as the average of the product of the X and Y values.

TABLE 2

In vitro Biostability Evaluation of DEX/Pe80A films

| | ESC Rating post 40-day MO/10-day $FeCl_2$ treatment | | | | | |
|---|---|---|---|---|---|---|
| | Sample | | | | | |
| Material | 1 | 2 | 3 | 4 | 5 | Final Rating |
| Pe80A | 4/3 | 4/4 | 4/4 | 4/4 | 4/4 | 15.3 |
| 0.1% DEX/Pe80A | 0/5 | 0/5 | 0/5 | 1/1 | 0/5 | 0.2 |
| 1% DEX/Pe80A | 0/5 | 0/5 | 1/1 | 1/1 | 0/5 | 0.4 | n=5. Final rating expressed as Mean. Observation at 70-100×.

Experimental rating=X/Y, X quantifies depth of cracks and Y quantifies extent of stressed surface coverage.

X=0 (no changes); 1 (change but no cracks, frosted areas); 2 (pits); 3 (cracks up to halfway through the film wall); 4 (confluent cracks); 5 (cracks 100% through the tubing wall, failure).

Y=0 (no changes); 1 (over $\leq$20% of surface); 2 (over >20 and $\leq$40% of surface); 3 (over >40 and $\leq$60% of surface); 4 (over >60 and $\leq$80% of surface); 5 (over >80% of surface).

4. Profile of DEX Elution from DEX/Pe80AS

Figure 9:
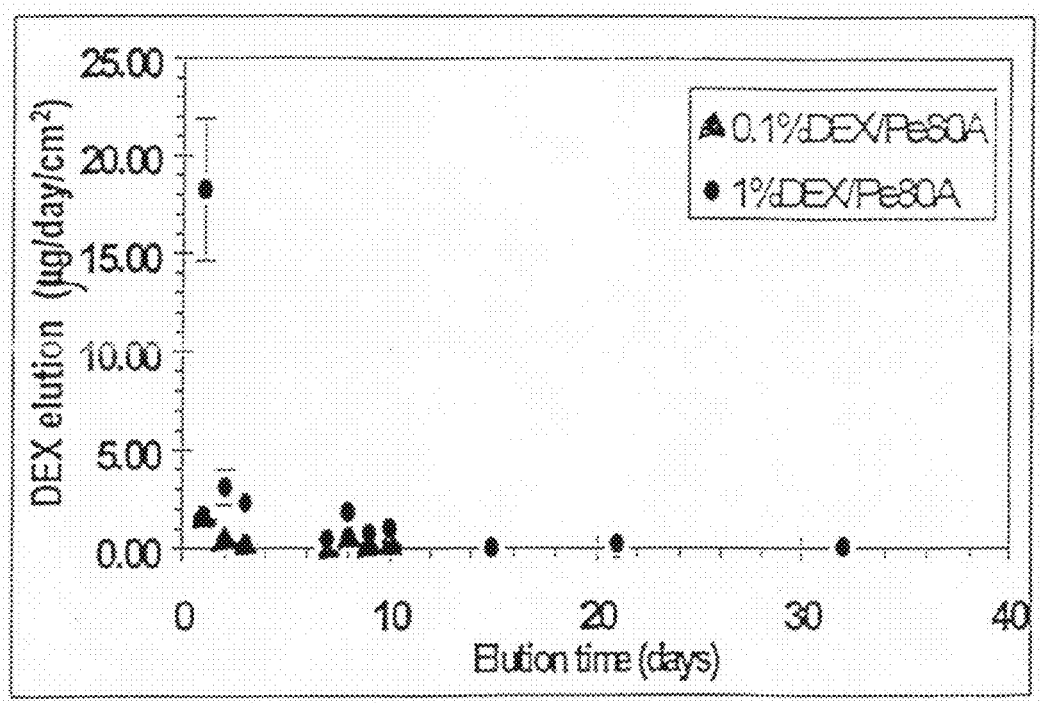
FIG. 9 shows a graph of the amount of dexamethasone elution per material surface area ($cm^2$) over a period of 32 days.

FIG. 9 shows the amount of DEX elution per material surface area ($cm^2$) over a period of 32 days. Independent of the DEX loading in the material, an initial burst of DEX release was observed at day 1. As suspected, the amount of DEX release was directly dependent on the total DEX concentration in the polymer. At the first day, 1.6±0.2 and 19.5±0.4 µg of DEX was eluted per $cm^2$ of material (0.1% and 1% DEX/Pe80AS, respectively). This release declined sharply thereafter. From day 5 to day 32 there was a slowly decreasing level of elution. After this gradual decline, a release of 0.02±0.01 and 0.06±0.03 µg/day/$cm^2$ was registered at day 32.

C. Conclusion

This in vitro biological system has shown to be an effective tool for studying polymer degradation. The use of components that are present and available in the body during host responses (i.e., Mo/MØs, Fe, stress) make it a rather realistic method to replicate ESC degradation. These observations suggest that $Fe^{+2}$ ions accelerate hydroperoxide decomposition, resulting in a degraded polymer, and that the down modulation of macrophage's ability to generate reactive oxygen species through a controlled DEX release prevents the initial steps that lead to polymer degradation. The efficacy of this approach was demonstrated in this study by the reduction of hydroperoxide formation and no subsequent ESC damage in polyetherurethanes (Pe80A) loaded with DEX and treated in the Mo/MØ/Fe/stress system.

Example 3

In vivo Biostability of Dexamethasone/Polymer Coatings in an Accelerated Test Model A. Materials and Methods 1. Biostability Sample Configuration Each biostability sample consisted of a piece of coated test tubing or control tubing strained to 400% elongation. Polysulfone mandrels were used to support the strained tubing. A 2-0 Ticron suture was used to sustain the strain of the tubing samples over the mandrels. The implant material strands consisted of five samples made specifically for test or control conditions. Each rabbit was implanted in the subcutaneous tissue of their backs with four, 5-sample strands. Each strand was identified by an attached glass bead whose color was coded to reflect the coating/control condition. The implant material strands measured approximately 0.3 cm in diameter and 7.0 cm in length. A total of 120 samples from 6 conditions were implanted in 6 rabbits, 20 per animal and 5 from each condition.

2. Test Coatings

Several formulations of DEX/Pe80A with varied DEX concentration were prepared. On the basis of DEX concentrations (w/w) the solutions were 0.1% DEX/Pe80A, 1% DEX/Pe80A, 5% DEX/Pe80A and Pe80A (w/o DEX). The solutions were prepared at 5% concentration of solids in THF and were used for dip coating of "PELLETHANE" 2363 80A tubing (Pe80A, Dow Chemical Co., Midland, MI), c/c (cold/cold extrusion process), 0.070 inch ID×0.080 inch OD. For negative controls Pe 2363 80A tubing, h/h (hot/hot process), 0.070 inch ID×0.080 inch OD, was used.

Sections of the cold/cold Pe80A tubings were coated with the different DEX/Pe80A preparations by 1 or more dips as follows:

Pe80A c/c tubing coated (1 dip) with 0.1% DEX/Pe80A—resulting in about 2.4 µg/cm$^2$ DEX initially and about 0.6 µg/cm$^2$ DEX after 400% elongation (referred to herein as 1/0.1DEX/Pe80A);

Pe80A c/c tubing coated (1 dip) with 1% DEX/Pe80A—resulting in about 22 µg/cm$^2$ DEX initially and about 5.4 µg/cm$^2$ DEX after 400% elongation (referred to herein as 1/1 DEX/Pe80A);

Pe80A c/c tubing coated (1 dip) with 5% DEX/Pe80A—resulting in about 120 µg/cm$^2$ DEX initially and about 30 µg/cm$^2$ DEX after 400% elongation (referred to herein as 1/5DEX/Pe80A); and Pe80A c/c tubing coated (4 dips) with 5% DEX/Pe80A—resulting in about 373 µg/cm$^2$ DEX initially and about 93 µg/cm$^2$ DEX after 400% elongation (referred to herein as 4/5DEX/Pe80A).

All the samples were sterilized with one cycle of ethylene oxide as is well known in the art.

3. Control Coatings

For positive controls, Pe80A-coated (1 dip) Pe 2363 80A tubing, c/c, 0.070 inch ID×0.080 inch OD was used. For negative controls, non-coated Pe 2363 80A tubing, h/h, 0.070 inch×0.080 inch OD, was used. Biostability samples in this condition were stress relieved (S.R.) at 150° C. for 15 minutes. All samples were prepared at 400% strain. The controls were sterilized with ethylene oxide.

4. Test Animals

Six (6) healthy adult male or female New Zealand white rabbits were used. All test and control biostability samples were implanted under general anesthesia. A total of 20 biostability samples were implanted in each animal. Due to the potential cross effect of dexamethasone, two animals were implanted with controls and four animals with DEX-containing samples. The individual samples were assembled into strands, with five samples per strand. Each strand had a colored glass bead to identify each experimental condition. They were implanted in the subcutaneous tissue in the backs of rabbits. Two strands were implanted on the left side of the spine parallel to the dorsal midline. Two strands were implanted on the right side of the spine parallel to the dorsal midline. Euthanasia and explanation of the samples were conducted at two timepoints, 6 and 10 weeks (10 samples per condition and per timepoint).

5. Accelerated Biostability Test Model

An accelerated in vivo biostabiltiy model was used. Sections of test and control tubings were prepared at 400% elongation. The negative control (Pe80A h/h) was stress relieved at 150° C. for 15 minutes. After one cycle of ethylene oxide sterilization, the sample strands were implanted.

6. Sample Analysis

Upon termination of the rabbits, the samples were explanted. No abnormal tissue response at the implant sites was noted macroscopically. The samples were debrided of tissue and rinsed in distilled water. After being dried, the samples were examined by optical microscopy at up to 70× without further sample preparation. For analysis, the samples were rated for environmental stress cracking in a manner similar to that described in Example 2 (Table 2). Each individual rating was slightly different, however, the ranges of values for X and Y were similar (X=0 (no changes) to 5 (cracks 100% through the tubing wall, failure) and Y=0 (no changes) to 5 (over >80% of surface).

B. Results

At the end of the 6 and 10 post-implanatation week, 3 animals per timepoint were euthanized and the samples explanted. The explanted samples were debrided of tissue and dried for optical microscopy (OM) evaluation. Representative samples were also evaluated by scanning electron microscopy (SEM) (samples were dried, mounted, and sputter coated with gold palladium as described in Example 1). Under OM, the samples were inspected for defects and flaws.

The overall results showed the following:

1. Positive control (worst case), Pe80A (NoDEX). At 6 weeks, 4 samples showed ESC failure (5/1 score), with shallow cracks and near failure observed in 3 samples. At 10 weeks, ESC failure occurred on all but 2 samples.

2. 1/0.1 DEX/Pe80A Test coating (0.6 µg DEX/cm$^2$). At 6 weeks, 6 samples showed ESC failure, and four showed no changes. At 10 weeks, 6 samples failed and 3 showed no ESC changes.

3. 1/1 DEX/Pe80A Test coating (5.4±0.7 µg DEX/cm$^2$). At 6 weeks, 4 samples showed failure, 1 near failure, and 5 samples with no ESC changes. At 10 weeks, all samples except one showed ESC failure.

4. 1/5DEX/Pe80A Test coating (30±0.6 µg DEX/cm$^2$). At 6 weeks, no failed samples were encountered. At 10 weeks, 6 samples showed ESC failure.

5. 4/5DEX/Pe80A Test coating (93.1 µg DEX/cm$^2$). At 6 weeks, none of 10 samples showed ESC failure. At 10 weeks, 4 samples showed ESC failure. The remaining 6 samples had no ESC present.

6. Negative Control (best case), Pe80A h/h S.R. (stress relieved). At 6 weeks, no ESC was found on 8 samples, while 2 samples showed minimal changes and shallow cracks. At 10 weeks, 4 out of 10 samples had shallow ESC present. The remaining 6 samples has no ESC present.

In some of the 1-dip coated specimens, oval areas of defective coating were observed. This defect seemed to correlate with ESC damage (cracks and shallow cracks) in the area.

Figure 10:
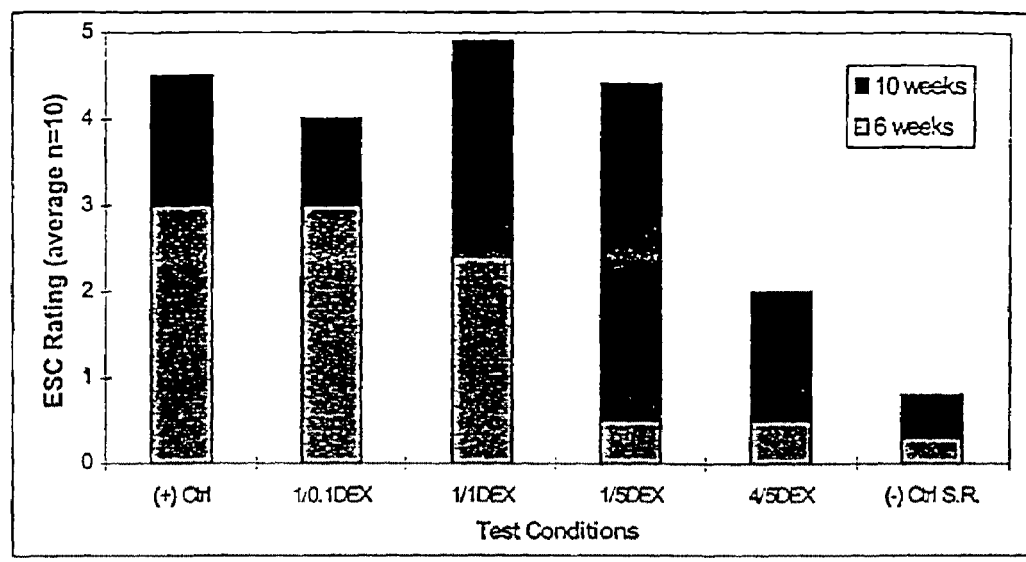
FIG. 10 is a bar chart showing graphically the overall environmental stress cracking in explants at 6 weeks and 10 weeks. Data were summarized using the highest (most severe) score of surface damage observed in the explanted biostability samples. Optical microscopic observation at 70× total magnification.

The protective mechanism appears to be effective as long as an adequate amount of DEX is present in the coating. This is evidenced by the clear DEX dose-dependency of the results. FIG. 10, which depicts a summary of the highest score in terms of ESC rating per specimen and per timepoint, graphically shows that while coating with 30 µg/cm$^2$ DEX (1/5DEX/Pe80A) was effective in preventing surface damage up to 6 weeks, an extensive damage, similar to the positive control condition was observed at 10 weeks. In contrast, coatings containing 93.1 µg/cm² DEX (4/5DEX/Pe80A) performed better than the positive control at both timepoints.

C. Conclusion

This study shows that dexamethasone has a protective effect on biodegradation of polymers and prevents the development of environmental stress cracking in oxidation-susceptible polyurethane.

Example 4

Anti-Inflammatory Devices: In Vivo Studies

A. Materials and Methods

1. Test Animals

The animals used for implantation were 3-month-old, 250-300 g body weight, female Sprague Dawley rats purchased from Charles River Laboratories, Wilmington, Mass.

2. Cage Test System

The metal wire mesh from which the cages were made was type 304 stainless steel with a mesh size of 24, a wire diameter of 0.254 mm, and interstices measuring 0.8 mm×0.8 mm (Cleveland Wire Cloth and Manufacturing Co., Cleveland, Ohio). The dimensions of the cages were approximately 3.5 cm long and 1.0 cm in diameter. Each cage contained a piece of the control or test material of interest. Empty cages were used as test controls. These cages were packaged and sterilized with ethylene oxide as is well known in the art.

3. Test Materials

Dexamethasone-Loaded Polyurethane. A segmented aliphatic polyurethane as described in U.S. Pat. No. 4,873,308 (Coury et al.) with no additives was loaded with micronized, free base dexamethasone USP (DEX, Upjohn Co.) using a cosolvation process. The appropriate amount of DEX was dissolved in tetrahydrofuran (with no butylated hydroxytoluene), Aldrich Chemical Co., Milwaukee, Wis.), followed by the polymer. The solutions contained 14% solids and 1% and 20% DEX. The solution was cast in 9.5 cm×9.5 cm "TEFLON" trays. The 20% DEX-containing film was dried in a freezer at −17° C. for 4 days and then in a vacuum oven at 50° C. and −30 inches Hg for 2 days. The 1% DEX-containing film and control film (no DEX) were dried under ambient conditions for 1 day, at 50° C. for 4 days, and then at 50° C. and −30 inches Hg for 3 days. The dried 20% film had a thickness of 0.7 mm, and the 1% film and control film had thicknesses in the range of 0.44 mm to 0.62 mm. Specimens weighing 24.97±0.04 mg (control), 24.98±0.05 mg (1D), and 25.01±0.06 mg (20D) were prepared, placed in cages, and sterilized with ethylene oxide.

4. Implantation Procedure

One cage was implanted subcutaneously on each of the right and left sides of anesthesized test animals. For implantation purposes, the 33 rats were divided into 2 groups. In the first group, 15 animals were implanted. In the second group 18 animals were implanted. A 1.0-cm to 1.5-cm incision was made in the skin about 2 cm above the tail and along the midline. A pocket was made in the subcutaneous space just below the right or left shoulder blade using blunt dissection. A cage specimen was then inserted through the incision and positioned at the level of the panniculuc carnosus, with the seam placed against the underlying muscle. Another cage specimen was implanted on the other side of the rat in the same fashion. The skin incision was closed with clips (Fisher Scientific, Pittsburgh, Pa.). The closed wound was then sprayed gently with Betadine solution.

5. Exudate Analysis

Exudate was aspirated with syringes from the cages at days 4, 7, 14, and 21 post-implantation. To avoid interference with the body's inflammatory response, no more than 0.3 ml of exudate was collected from each cage at each time period. Total and differential cell counts were performed by personnel with no information about the exudate's identification using standard techniques. After the 21-day exudate sampling, the rats were euthanized by carbon dioxide asphyxiation.

6. Total Cell Count

To screen for the presence of infection, an aliquot from each exudate sample was cultured on 5% sheep's blood agar plates. Immediately after the exudate was withdrawn at days 4, 7, 14, and 21 post-implantation, the total cell count for each exudate was determined by hemocytometer counting.

7. Differential Cell Count

An aliquot of the exudate that contained approximately 15000 white blood cells (leukocytes) was transferred to a test tube with 300 ml RPMI-1640. Aliquots (200 µL) of the cell suspension were spun down onto a clean glass microslide using a cytocentrifuge (Shandon Inc., Pittsburgh, Pa.). These microslides were stained with "DIFF-QUICK" stain (Baxter Scientific, McGraw, IL) according to the manufacturer's recommendations and used for a quantitative differential cell count. Polymophonuclear (PMNs), monocyte-derived macrophages (Mo/MØs), and lymphoctyes were the cell types counted for this analysis.

8. Cage Analysis

Following the 21-day exudate wighdrawal, the implanted cages were removed from the euthanized animals and immediately evaluated macroscopically. The top edge of the cage was cut with a pair of scissors along the inner surface seam. Intact and opened cages were examined and described. After analysis, the cages were immersed into 1-% formalin jars.

To assess the amount of fibrous tissue in the explanted cages, the cages were dried at 60° C. for 72 hours and their dry weight was recorded. Following tissue digestion by cage immersion in 6N KOH for 2 hours at 80° C., the weight of each stainless steel cage was again recorded. Dry tissue weight (dry tissue/(total cage weight—cage's stainless steel weight) per cage was calculated.

9. Material Surface Analysis

Polymer specimens were retrieved with tweezers where possible, rinsed in "PLASMA-LYTE" A (Baxter Scientific, McGraw Park, Ill.), and placed onto a microslide. The specimens were then cut into two pieces with a razor blade. One piece was placed into a cold fixative containing "PLASMA-LYTE" A and 1.5% glutaraldehyde and stored at 4° C. The other piece was placed into an alcohol fixative and subsequently stained with "DIFF-QUICK" stain.

The polymer films (0.6 mm thick) were sufficiently thin and transparent to enable visualization of stained adherent leukocytes using optical microscopy (OM) with an Olympus BX40 light microscope. The stained polymer specimens were initially characterized on both sides, which were very similar, with numerous leukocytes adhering to each surface. Every cell attached to the substrate surface was counted differentially at 45×. Each foreign body giant cell (FBGC) was counted as one cell; although the number of nuclei contained within each FBGC was also recorded.

For SEM evaluation, specimens were removed from the glutaraldehydr fixative, rinsed in "PLASMA-LYTE" A three times for 15 minutes each and prepared as described in Example 1.

10. Statistical Analysis

The data is presented as the mean±SD. For total cell counts the unpaired Student's t test at 95% level of confidence (p<0.05) was used to compare group means. Test materials 1D (1% DEX) and 20D (20% DEX) were compared to the PU control film made using THF (A) and an empty cage (EC).

B. Results

1. Exudate Analysis

Figure 11:
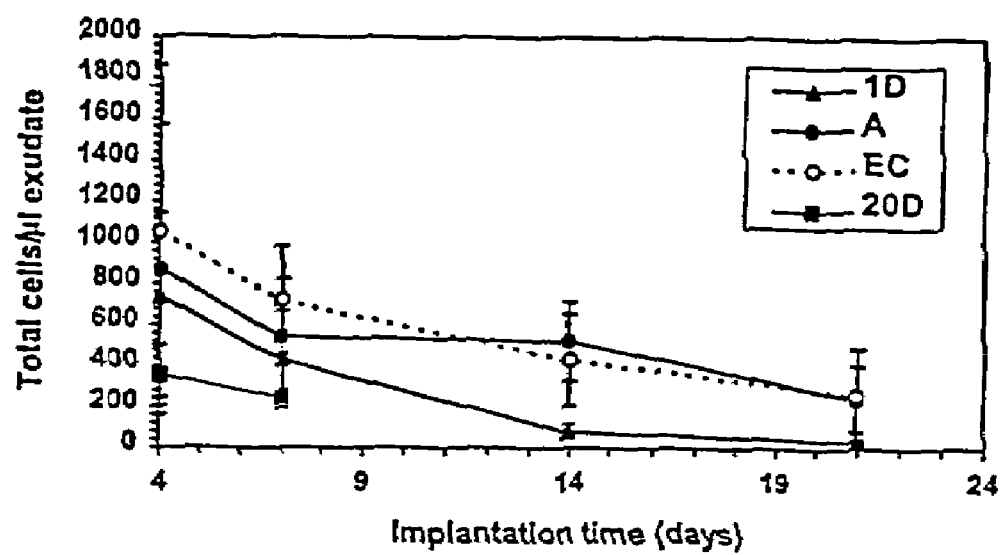
FIG. 11 is a graphical representation of the comparative total cell count in cage exudate in response to different PU materials: 1D=1% dexamethasone in polyurethane; 20D=20% dexamethasone in polyurethane; A=control; and EC=empty cage.

The leukocyte densities in the exudate samples drawn from the differential materials at 4, 7, 14, and 21 days post-implantation are displayed graphically in FIG. 11. A gradual decrease in cell density after 4 days was evident in all test conditions. DEX-containing materials (1D and 20D) clearly elicited lower cell numbers during the entire implantation time. This effect was statistically significant at 14 and 21 days for 1D and at 7 days for 20D.

At 4 days, 1D elicited 90% and 20D elicited only 40% of the cell number that was elicited in the control material (A). At 21 days, 1D exudates contained only 13.9% of the number of cells observed in exudates from the control polyurethane. Unfortunately, analysis for 20D material stopped at 7 days because of infection. Comparison of the control materials showed that the choice of solvent (THF and NMP) used in preparation of the PU film produced an effect on the results.

All cell types in the exudate, which included PMNs, macrophages, and lymphocytes, decreased over time post-implantation. At day 4, the leukocytes were dominated by polymorphonuclears (PMNs) and macrophages (Mos). At later time points, however, there was a rapid decline in the percentage of PMNs, reflecting the establishment of a chronic inflammatory response. While the concentration of the three leukocyte cell types in the exudate decreased with time, the considerable decrease in PMNs provided for the percentage increases observed for the two mononuclear cell types. Only macrophages and FBGCs were present on material surfaces at 21 days, although macrophages, lymphocytes, and PMNs were characteristically observed in exudates.

The total exudate cell count for test materials containing 1% DEX (1D) and 20% DEX (20D) elicited lower cell counts control materials A and EC, evidencing that they have significantly less potential to elicit inflammation. This effect was sustained throughout the study for 1D. The low PMN numbers observed at 14 days (approximately 5 cells/μL exudate) and 21 days (approximately 0.5 cell/μL exudate) in the 1D exudates, suggests that there was little or no influx of newly recruited PMNs to the inflammatory site. In other words, a mildly chronic inflammatory status prevailed after the acute phase had concluded. By contrast, PMNs were still present at 14 and 21 days in exudates from controls A and EC, which indicates that dexamethasone may accelerate the process toward a full wound-healing response.

2. Material Surface Analysis

Dramatic macroscopic differences were observed between DEX/PU-containing cages and other cages. Fibrous capsule formation was significantly lower in 1D cages (40.6±10.6 mg dry tissue per cage) than in control A cages (218.1±72 mg dry tissue per cage) or empty cages (207.9±70.7 mg dry tissue per cage). This shows the effectiveness of dexamethasone in reducing collagen production at the tissues surrounding an implant.

Surface analysis of materials after 21 days of implantation showed adherence of cells of the macrophage lineage. Under light microscopy at 45×, the majority of adherent cells were readily identified as FBGCs, although some of the observed cells showed classic macrophage morphology.

Different densities of adherent leukocytes were present on the surfaces. Most of the surfaces evidenced a more or less random cell distribution; however, there were areas of high cell population density, areas of scattered cells and occasional cell aggregates, and areas of very few cells. Adherent leukocytes evidenced varied morphologies and degrees of cytoplasmic spreading. Some of the cells had assumed unusual shapes, and some exhibited a deterioration of the cellular membrane, resulting in considerable effacement of the cell architecture. By day 21, some cell debris was present on all surfaces, except on 1D material. Since no surface analysis was done at earlier timepoints (e.g., 4, 7, 14 days), the progression in the process of cell distribution/adhesion was not explored.

Stained surfaces of 1D material evidenced a greater macrophage to FBGC ratio on their surfaces. On these surfaces, several macrophages and only scattered FBGCs were observed. In contrast, a considerable number of FBGCs and only occasional macrophages were present on the control material A (polyurethane film made with THF and no dexamethasone).

C. Conclusion

This study shows that dexamethasone-loaded polyurethane is effective at reducing inflammation in response to biomaterial implantation.

Example 5

In vivo Evaluation of Dexamethasone-Coated Transvenous Pacing Leads

A. Materials, Methods, and Results of DEX-Treated Pacing Leads

1. Preparation of Lead Prototypes

A set of experiments was designed to test the feasibility of coating pacing leads with DEX-loaded PU formulations. A segmented aliphatic polyurethane as described in U.S. Pat. No. 4,873,308 (Coury et al.) was loaded with DEX through cosolvation in THF as described in Example 4. The ratio of drug to polymer was varied to achieve either 1% or 5% drug-loading levels in solution. The appropriate amount of drug was first dissolved in THF. The polymer was then added and allowed to dissolve in the solution. At completion, the solutions were 11% solids (w/w). Under a filtered laminar flow hood, transvenous pacing leads Model Nos. 4023 and 4523 (Medtronic Inc., Minneapolis, Minn.) were weighed and then dipped into the DEX/PU/THF solutions. In order to vary DEX-loading in the devices, the solutions contained 0%, 1%, and 5% of DEX (w/w), at 11% wt/wt total solids. A control included only a coating of PU (11% solids).

A dipping device was configured to control the speed of immersion of the leads into the solution. Prior to the coating, the electrode tips and tines were protected with a piece of polypropylene tubing and parafilm. To facilitate the immersion of the leads into the DEX/polymer solution, a silicone coated 6.5 g. round split shot sinker (Water Gremlin Co., White Bear Lake, Minn.) was attached distally to each lead. Leads were then lowered into the coating solution to a depth of 15 cm (lead body) at a speed of 1.9 cm per second and then immediately lifted from the solution. Between dips the coated leads were left for at least about 4 hours in a forced-air oven (80° C.) and then vacuum dried (−30 inches Hg) for at least about 24 hours.

The total weight of the coatings on the devices increased with each additional dip, showing a good weight-to-dip linearity. In order to obtain a varied range of total DEX loading on these devices, the coating was considered completed following 2 dips for control PU-coated leads, 3 dips for 1% DEX/PU coated leads, and 4 dips for 5% DEX/PU coated leads. After dipping, the devices were released from their electrode/tines protection and trimmed under microscope. Final DEX content was determined by weighing each lead.

Dip coating leads in the DEX/PU solutions resulted in the deposition of a homogeneous polymer layer on the body surface. On the basis of DEX content per lead, three conditions were prepared. The final DEX loading is shown in Table 3. The coated devices were packaged and sterilized in ethylene oxide before their use for elution studies or for canine implantation.

TABLE 3

| | DEX Loading on Coated Leads (15 cm) | | | |
|---|---|---|---|---|
| Drug | 1% DEX/PU ("Low") | | 5% DEX/PU ("High") | |
| loading | Atrial | Ventricular | Atrial | Ventricular |
| Total DEX (mg) | 0.5 ± 0.1 | 0.4 ± 0.1 | 3.4 ± 0.2 | 2.8 ± 0.1 |
| DEX/cm$^2$ S.A. (mg) | 0.09 ± 0.02 | 0.08 ± 0.02* | 0.6 ± 0.04 | 0.5 ± 0.01* |

Note:
Data expressed in mg, mean ± SD, n = 3, *n = 7

2. Kinetics of In Vitro DEX Elution from DEX-Coated Pacing Leads

The in vitro profile of DEX release from the two DEX-containing lead conditions, 1% DEX/PU and 5% DEX/PU ("Low" and "High" DEX loading respectively) was determined through elution experiments carried out at 37° C. in PBS.

Figure 12:
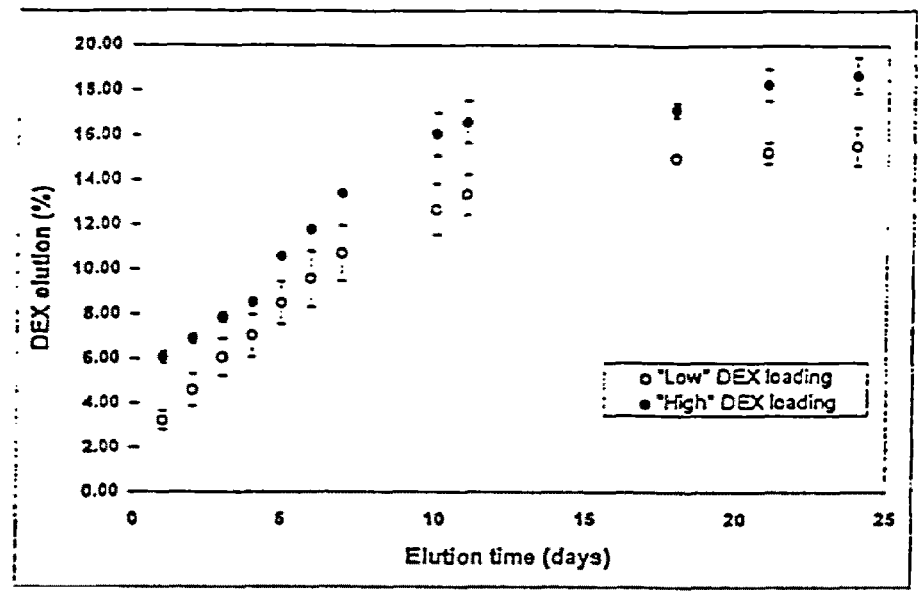
FIG. 12 is graphical representation of in vitro elution of dexamethasone from dexamethasone-coated leads. "Low" (1% DEX/PU) and "High" (5% DEX/PU) loadings were used. Elution percentages of the total theoretical dexamethasone loading was determined in PBS at 37° C.
Figure 13:
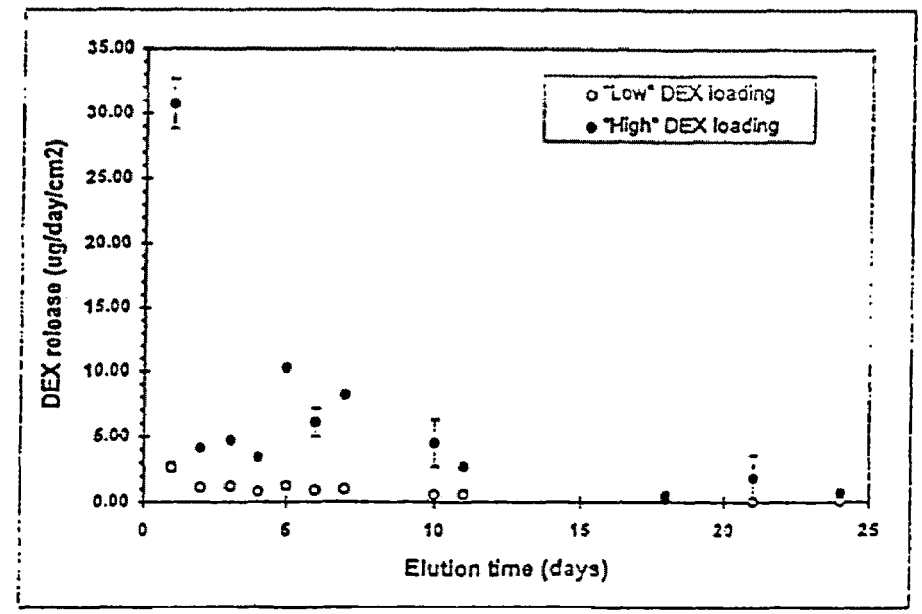
FIG. 13 is graphical representation of in vitro elution of dexamethasone from dexamethasone-coated leads per surface area vs. time. "Low" (1% DEX/PU) and "High" (5% DEX/PU) loadings were used. Elution was conducted in PBS at 37° C.

The coated portion (15 cm) of two leads from each condition were used for these analyses. Following the separation of the electrode/tines portion from the lead body (to remove the dexamethasone in the electrode), the coated lead bodies were immersed in PBS at 37° C. and the eluates were analyzed using HPLC as described in Example 1 at different time points within a 24-day period. FIG. 12 shows the cumulative DEX elution over time, expressed as the percentage of the total DEX loading per lead. Both lead conditions evidenced similar profiles of DEX elution. Following an accelerated elution lasting up to 10 days, it was observed that the elution slowed down. At 24 days, 15.5% and 18.7% of the total theoretical DEX loading was eluted from the "Low" (1% DEX) and "High" (5% DEX) DEX coated leads, respectively. FIG. 13, shows the amount of DEX elution per material surface area (cm$^2$) per day over a period of 24 days. In an initial burst of drug release, 2.7±0.4 µg and 30.8±1.9 µg of DEX was released per cm$^2$ of leads coated with the "Low" and the "High" DEX conditions, respectively. The release of DEX declined sharply thereafter. From day 4 to day 24 there was a gradual decline in DEX release. At the 24th day of this experiment, 0.07±0.09 µg and 0.7±0.1 µg of DEX was released per cm$^2$ for the "Low" and the "High" DEX conditions, respectively. Although in vitro elution rates may be significantly different from the elution rates in vivo, these studies were useful in monitoring and validating the DEX loadings and the elution profiles of DEX coated-devices.

This release profile and elution rate (data not shown) were similar to that obtained with materials used in the in vivo cage study in Example 4. By varying the DEX concentration in the coating solutions, the percentage of solids in the coating solutions, or the number of dips, a useful biological range of DEX loading was achieved. This demonstrates the feasibility of obtaining coatings that exhibit desired loadings and release profiles of DEX for specific device applications. Of course dip-coating may not be the only method for applying this technology to leads and other devices. It is possible that extrusion and/or co-extrusion of DEX/PU materials could be used.

B. Materials, Methods, and Results of In Vivo Evaluation of DEX-Coated Pacing Leads 1. Test Animals The animals used for implantation were canines of random sex and with ≧25 kg body weight.

2. Lead Implantation

Three conditions of coated pacing leads were implanted into canines. As shown in Table 4, two DEX/PU coated lead conditions ("Low" and "High" DEX loading) and one PU-coated lead condition (control) were implanted in 6 canines. For this study, 3 (2 ventricular and 1 atrial) leads from test or control treatment conditions were implanted per dog. A 3-lead-per-dog model was adopted to increase the amount of hardware within the intracardiac chambers. The number of animals and specimens per material/condition are displayed in Table 4.

TABLE 4

| Experimental Distribution of Animals and Coated Lead/Conditions | | | |
|---|---|---|---|
| DEX Loading | Coating Condition | No. Canines | No. Leads |
| "LOW" | 1% DEX/PU | 2 | 6 |
| "HIGH" | 5% DEX/PU | 2 | 6 |
| NO DEX | PU | 2 | 6 |
| Totals | 3 | 6 | 18 |

The ventricular leads were implanted through a 3rd intercostal right thoracotomy via costo-cervico-vertebral trunk (CCTV). The atrial leads were implanted through a right jugular venotomy. With the aid of fluoroscopy, one ventricular lead was placed in the RV apex and the other ventricular lead was placed in the RV posterior wall at least 1 cm from the apical lead. Thresholds of less than 1.0 V at 0.5 ms verified adequate ventricular and atrial lead placement using the Model 5311 Patient System Analyzer (Medtronic Inc., Minneapolis, Minn.). After securing leads in the vessels, the lead connector ends were tunneled to the right chest wall and capped with IS-1 pin caps. Lead placements were further documented with lateral and dorso-ventral X-ray analyses. In general, the surgical and post-surgical activities evolved without complications. Due the nature of this study, no steroid medications were administered to any canine.

3. Evaluation of Systemic Parameters

The regulatory influence of circulating steroids during the in vivo stage of implantation was evaluated. Severe depression of circulating levels of monocytes has been reported using (0.6 mg/g body weight, s.c.) hydrocortisone. Steroids can also depress the circulating level of T-lymphocytes in mice, rats, and humans. Likewise, steroids, particularly at immunosuppressive doses, reduce the resistance to bacterial infection. Infections, when present, can be detected by changes in the differential distribution of blood cells or by positive bacterial culturing.

In order to evaluate systemic changes that might be attributable to DEX release (i.e., excessive corticosteroid, infection, etc.) from the treated devices, blood and hemogram analyses were performed at weeks 1, 2, 4, 8, and 12 post implant. At least one of these analyses was performed in the pre-operatory. Results showed that lymphocyte numbers were either within normal range or slightly elevated. In summary, a consistent or progressive finding of lymphopenia and/or eosinopenia was not noted in any dog on the study.

4. Intracardiac Macroscopic Pathology Evaluation

After 13 weeks (3 months) of lead implantation, the animals were heparinized, X-rayed, and euthanized following a standard procedure. Necropsy was performed by a pathologist who was kept blind to the different conditions in the study. Special emphasis was focused on the intracardiac compartment to evaluate lead-tissue relationships, encapsulation of the devices, their extension, thickness etc.

Following euthanasia, the heart was dissected, opened, and carefully removed. Right heart cavities were opened through a longitudinal incision to expose the implanted leads. Low and high magnification photographs were taken prior to and after opening the heart and after heart removal. After complete analysis and description of the findings, the hearts were placed in 10% buffered formalin.

With minimal differences among the dogs, the proximal ends of the three leads were surrounded by fibrous tissue in the subcutis over the right thorax. In general, two leads (ventricular) entered the thorax directly through the right thoracic wall and then to the venous system through the right CCTV at a venotomy site. One lead (atrial) traveled anteriorly through the subcutis over the right scapula to the right ventral neck, where it entered the jugular vein through a venotomy site. Subcutaneous sheaths were thin and tightly apposed to the leads.

Dog Receiving Leads Without DEX. Two foci of soft yellow multifocal endocardial thickening (12×4 and 0.5 mm diameter respectively) were found dorsal to the intervenous tubercle. Atrial lead. A short translucent tissue sheath (<1 cm) surrounded the lead immediately distal to a secure jugular venotomy site. Its implantation site was verified to be within the right atrium appendage (RAA) in which a uniform, smooth, and shiny tissue sheath (8 mm long) was observed. The rest of the body lead was free of any adherent tissue from the level of the CCTV to its implant site in the right atrium appendage (RAA). Ventricular leads. Immediately distal to the CCTV venotomy site, a tissue sheath (4 mm long) covering the two leads was observed. This tissue sheath was complicated distally by the presence of an eccentric (5 mm long) antemortem thrombus. Within the anterior vena cava (AVC), right atrium (RA), and right ventricle (RV), both leads were predominantly free of adherent tissue. However, within the AVC, both leads were in a common tissue sheath, which was in turn attached to the luminal wall of the roof of the AVC. This short tissue had smooth translucent and uniform characteristics, and covered 7 mm and 9 mm of the two leads, respectively. The lead that was implanted more on the RV wall was adhered to the free wall of the RV by a lateral attachment. This tissue sheath with a trabecular muscle and smooth, shiny translucent tissue characteristics covered the lead for 12 mm.

Dog Receiving Leads Without DEX. Atrial. Implant site was secure and located on the free wall of the RAA. Ventricular. Immediately distal to the CCTV, both leads are in a common tissue sheath which bifurcates slightly at its distal end. This tissue sheath was extended distally from the CCTV venotomy site and covered 1.2 cm of the apical lead and 1.1 cm of the wall lead. The apical lead was adhered to the tricuspid valve apparatus over a distance of approximately 1.5 cm. The most distal end of the apical lead was not visible. Implant site for the apical lead was secure. The caudal portion of the parietal leaflet of the tricuspid valve has its margins thickened by soft yellow tissue.

Dog Receiving Leads Coated With 1% DEX/PU. Atrial lead. At the junction of the AVC and the crest of the RAA, there was a prominent soft endocardial thickening. The lead was securely implanted on the free wall of the RAA. Within the dorsal AVC, there was a multifocal yellow firm nodular endocardial thickening. Each nodule (2-3 mm diameter) were distributed over an area approximately 1.5 cm×1.0 cm. Ventricular leads. CCTV venotomy site was secure. Both leads, immediately distal to the CCTV venotomy site, were in a common tissue sheath with a mild thrombus on it. Apical and wall leads passed from the CCTV and was free of any tissue or material adhesion until it reaches the tricuspid valve, and present an adhesion to the parietal leaflet of 5 mm long. At this adhesion site, the margin of the valve was thickened by a firm nodular smooth shiny tissue. Distal to the tricuspid valve, the leads were free of adherent tissue or material until reached the RVA and the interventricular septum, in which showed a secure fixation. RVW lead this the lead is free of any adherence of tissue or other material until it reaches its implant site in the RV apex. The other lead (RV wall) has immediately to the CCTV venotomy site, two pale nodules of adherent tissue or material, each <1 mm diameter and a very transparent tissue sheath over a length of 3 mm. Approximately 7 cm distal to the CCTV venotomy site, two segments of tissue sheaths (5 mm and 2 mm long respectively) were observed, neither sheath was adhered to adjacent cardiac tissues. This lead passed through the tricuspid valve at its caudal commissure, no adhesions were observed. Focal soft yellow 6×3 mm endocardial thickening was noted on the RV free wall.

Dog Receiving Leads Coated With 1% DEX/PU. Atrial. Immediately distal to the jugular venotomy site, the lead was within a 1.5 cm long smooth and shiny tissue sheath of variable thickness. This tissue sheath was complicated distally by an organized antemortem thrombus that was 0.5 cm long. This lead was securely implanted in the RAA. Multiple soft, smooth, and shiny endocardial thickenings on the roof of the AVC, on the anterior surface of the intervenous tubercle and at the junction of the RAA with the RA and the AVC were observed. The RA endocardium adjacent to the origin of the RAA was thickened by a pale opaque tissue. Ventricular. Immediately distal to the CCVT venotomy site, both leads were in a common fibrous sheath 1.0 cm long that was complicated distally with a 1.0 cm long organized thrombus. One lead was noted to pass into the os of the coronary sinus and into the middle cardiac vein. The middle cardiac vein was opened, and the lead was found to be ensheathed over the distal 6 cm of the lead. The other lead passed from the right atrium into the RV, where it was securely implanted near the RVA. This lead passed through the tricuspid valve near the caudal commissure; it remained free of any adhesions to the valve apparatus. The distal end of this lead was buried within the trabecular muscle. The leaflets of the tricuspid valve had a soft, smooth, and shiny thickening in areas apposed to the RV lead.

Dog Receiving Leads Coated With 5% DEX/PU. Within the anterior mediastinum, located at the thoracic inlet and adhered to the right first rib, an encapsulated gauze sponge was found. Atrial lead. Its implantation at the free wall of the RAA near the origin of the RAA was verified. The lead was free of any adherent tissue or material. The tip of the electrode was visible from the epicardial surface through the epicardium, but no perforation was evident. Ventricular leads. Immediately distal to the CCTV venotomy site, the apical lead was enclosed in a tissue sheath 7 mm long. Distal to this, the lead was free of any adherence of tissue or other material until it reached its implant site in the RV apex. The other lead (RV wall), immediate distal to the CCTV venotomy site, had two pale nodules of adherent tissue or material, each <1 mm diameter and a very transparent 3 mm tissue sheath. Approximately 7 cm distal to the CCTV venotomy site, two segments of tissue sheaths, (5 mm and 2 mm long, respectively), were observed, neither sheath was adhered to adjacent cardiac tissues. This lead passed through the tricuspid valve at its caudal commissure. No adhesions were observed.

Dog Receiving Leads Coated With 5% DEX/PU. Atrial lead. The lead that entered the venous system through the jugular vein had its distal end within the AVC (dislodged). A tissue sheath (1 cm long) was present around the lead body immediately distal to the jugular venotomy site. This lead was observed movable within its venotomy ligature. Within the RA, the septal wall, and around the RAA origin there were opaque thickenings of the endocardium. No other adherent tissue was observed on the rest of the body lead. Ventricular leads. Immediately distal to the CCTV venotomy site, a thin transparent 3 mm long tissue sheath, covering one lead was observed. The other lead had a more translucent tissue sheath 8 mm long, which was complicated distally by the presence of an eccentric, partly organized thrombus. This latter lead was adhered to the wall of the AVC. Distal to these tissue sheaths, both leads were free of any adherent tissue or material within the AVC or RA. Both leads passed through the tricuspid apparatus and remained free of any adhesions. A lead that passed more anteriorly in the RV was not implanted at its distal end but was freely movable. The lead that passed more caudal in the RVA was securely implanted and had a 3 mm sheath at its implantation site.

5. Histology of Intracardiac Lead-Associated Tissues

In general, occasional tissue sheaths were observed during the macroscopic pathologic evaluation. Lead-associated tissues, located at the lead portion from at least 1 cm distal from the venotomy site to at least 1 cm proximal to the electrode fixation site, were microscopically evaluated by a pathologist. One tissue sheath per condition was processed for histology, and a transversal section was stained with hematoxilin and eosin. The pathologist was kept blind to the treatment condition related to each specimen.

Although the results from the evaluation of these three specimens cannot be conclusive (n=1), they illustrate important findings that may be relevant to the different surface treatments in the study. A brief summary of the inflammatory characteristics and ranking of these slides follows. The least inflamed tissue is first:

Specimen From Dog Receiving Leads Coated With 5% DEX/PU. Thinnest tissue sheath, no inner zone of partly organized thrombus, scant inflammation comprised of macrophages and few neutrophils.

Specimen From Dog Receiving Leads Coated With 1% DEX/PU. Moderately thick tissue sheath, inner zone of partly organized thrombus, slightly more inflammation comprised of macrophages.

Specimen From Dog Receiving Leads Without DEX. Moderately thick tissue sheath, inner zone of partly organized thrombus, moderate inflammation comprised of lymphocytes, plasma cells, macrophages, eosinophils, and few neutrophils.

6. Organ Evaluation

The regulatory influence of circulating steroids during the in vivo stage of implantation was evaluated. The negative feedback control of steroids on the neuroendocrine axis and on the anterior pituitary is well accepted. Prolonged suppression of ACTH release by steroids is associated with degenerative changes in the hypothalamus and in the anterior pituitary. These processes result in histopathological changes in the adrenal glands.

For these analyses, tissue sections of the adrenal glands were harvested from each animal. Other tissues for evaluation included liver, spleen, kidney, and lungs. Gross observations of the organs were documented by the pathologist. These tissue specimens were processed for routine histology studies.

In summary, the results showed no gross abnormalities in the evaluated organs. In the adrenal cortices of all dogs, the zona fasciculata cells had the foamy to vacuolated cytoplasm typical of active, steroid-secreting cells. There was no evidence microscopically of any lymphopenia, which might result from excessive administration of steroids. Microscopic evaluation of other organs revealed tissues with only minor abnormalities, none of which were attributable to corticosteroid coating on lead bodies. A consistent or progressive lymphopenia and/or eosinopenia was not noted in any dog in the study. Gross findings did include a) the presence of a body consistent with a gauze sponge found within the thoracic cavity of one of the dogs and b) bilateral subcutaneous carpal swelling of moderate size in another of the dogs. In general, all examined organs were found within normal limits.

7. DEX Elution Studies from Explanted Leads

Figure 14:
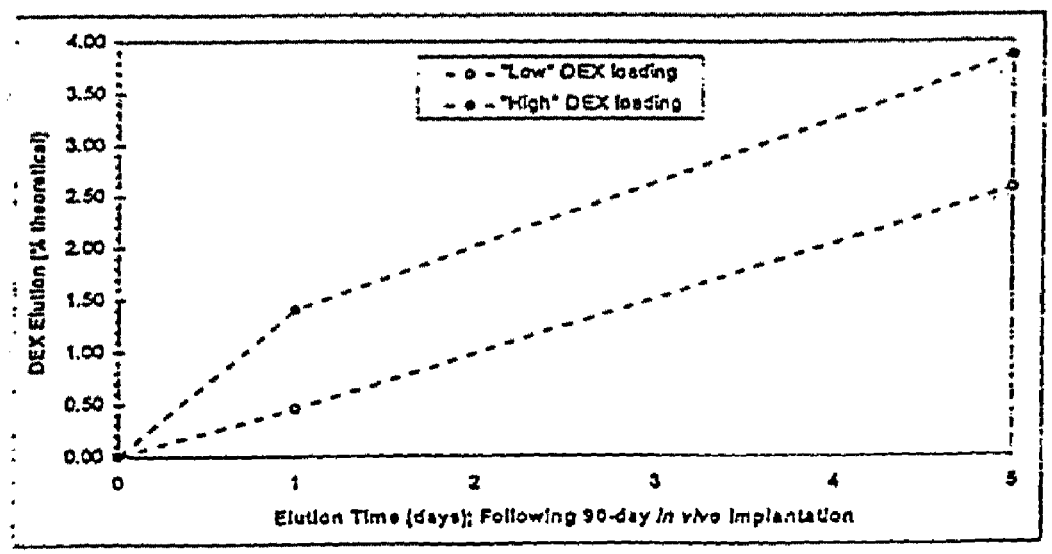
FIG. 14 is graphical representation of in vitro elution of dexamethasone from dexamethasone-coated leads following 90 days in vivo implantation. "Low" (1% DEX/PU) and "High" (5% DEX/PU) loadings were used. Elution percentages of the total theoretical dexamethasone loading was determined in PBS at 37° C.

The leads recovered immediately after pathological evaluation were subjected to in vitro elution in PBS at 37° C. The in vitro elution experiments are described above ("Kinetics of in vitro DEX Elution from DEX-Coated Pacing Leads"); analyses were conducted on eluates at 1 and 5 days of elution, and the DEX elution was calculated in terms of percentage of the initial DEX loadings in each lead (FIG. 14). The accumulated 5-day DEX release (in PBS) from explanted "low" and "high" lead conditions was 2.6% and 3.9% of the total DEX loading, respectively. This indicates that during the in vivo period of implantation, up to 90 days, DEX was still present for elution.

C. Conclusion

Coating, as a modality for applying the technology to devices, has been useful in the preparation of pacing lead prototypes and for demonstrating the feasibility of this concept. However, it is possible that extrusion and/or coextrusion of DEX/PU materials may be favorable for large-scale use and manufacturing of DEX-biomedical devices.

Overall, the in vivo study to evaluate the biological performance of DEX-pacing leads showed no complications. Results showed no DEX-related systemic toxicity during the 3-month implantation, as evidenced by hematological parameters or by histology of target organs. At the intracardiac portion of the leads (DEX-treated portion), minimal or no associated tissue encapsulation was observed in DEX-coated and control conditions. The observed tissue encapsulation were characterized as a typical reaction to polyurethane, as assessed macroscopically.

Microscopic histology of the occasional (intracardiac) lead-associated tissue sheaths (1 per condition), showed various degrees of inflammation, the intensity of which was inversely related to the presence of and the dose of DEX on the test device surfaces. These differential inflammatory findings in lead-associated tissue sheaths may suggest an active down-modulation of the cell functionality at the interface attributable to a localized DEX release. No systemic nor histological evidence of infection was found in the canines implanted with DEX-coated devices (n=4) or with control devices (n=2).

After 3 months of in vivo implantation, explanted DEX-coated leads showed a detectable DEX elution, with an accumulated elution of 2.6% and 3.9% of the total DEX at 5 days from "low" and "high" DEX-treatment conditions, respectively. This indicates the presence of DEX in the polymeric matrix during the in vivo period, suggesting an active DEX elution to the cell-biomaterial interface. Information on DEX release from explanted leads suggested that a sustained DEX release was still present after 3 months of in vivo implantation.

Example 6

In vitro Elution Profile for Dexamethasone Silicone Inserts

Materials. Standard silicon inserts for sewing rings and annuloplasty rings is about 52.5 weight percent Medical Grade Silicone and about 47.5 weight percent barium sulfate (to impart radiopacity). The percentage of barium sulfate can be as low as about 40% while still allowing radiodetection of the ring. During compounding of the drug-loaded insert, a non-water soluble form of dexamethasone (DEX) was added to the mixture, and a corresponding amount of barium sulfate was removed. For example, a 1% dexamethasone-loaded insert contained Si 52.5%, $BaSO_4$ 46.5%, DEX 1%. Inserts containing 5%, 2.5%, 1% and 0.5% DEX were prepared. A silicone insert was also prepared containing both a water soluble form of dexamethasone (DMP) and DEX. This insert contained a total of 1% dexamethasone, in a 3:1 ratio of DEX to DMP Methods. Cumulative release of DEX from the drug-loaded samples was determined over 71 days. The samples were completely immersed in phosphate buffered saline (PBS) and placed in and incubator at 37 C. At various time points aliquots of PBS were removed and replaced with fresh buffer to keep the elution volume constant. The removed aliquots were analyzed by high performance liquid chromatography (HPLC) for DEX content.

Figure 15:
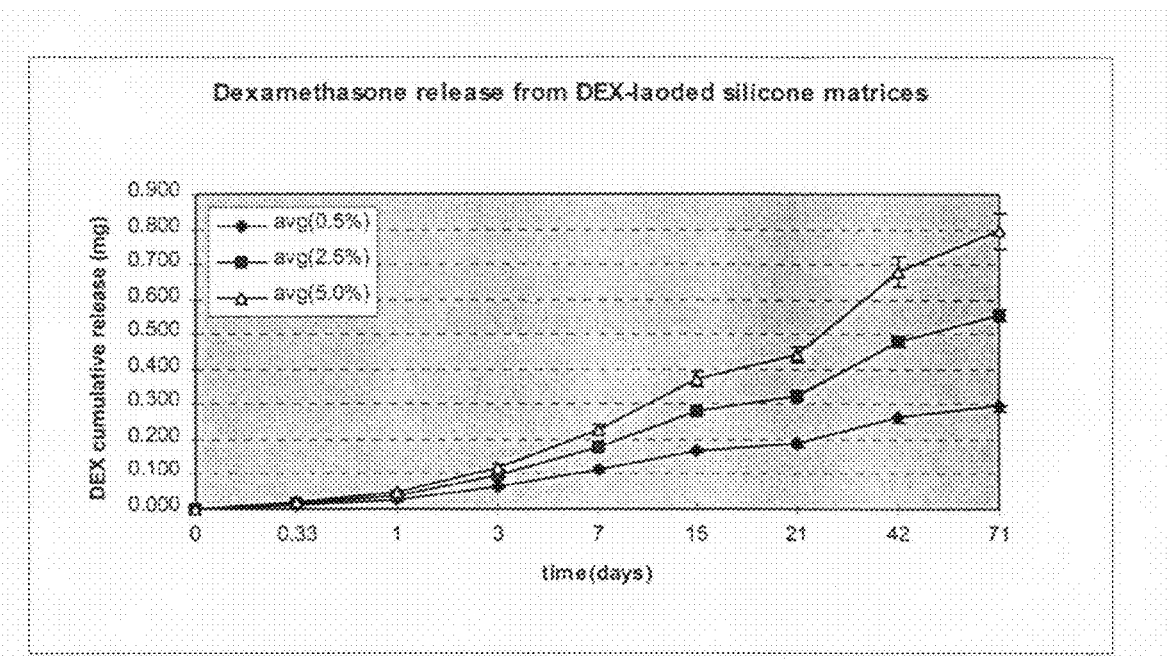
FIG. 15 shows in vitro elution profiles for DEX-loaded silicone inserts having different weight percentages of DEX.

Results. FIG. 15 shows elution profiles for DEX-loaded inserts. Notable aspects of these profiles are the dose-dependent response and the slow release, the latter being a feature that bodes well for a long term application. By day 71, the 5% loaded insert released approximately 5% of its theoretically loaded amount, the 2.5% loaded insert released approximately 7.5% of its theoretically loaded amount, and the 0.5% loaded insert released approximately 20% loaded amount.

Because non-resolution of the healing during the acute stage of inflammation (occurring 4-7 days after implantation) can lead to prolonged and severe chronic events in vivo, an effort was made to increase the amount of dexamethasone released early in the profile. It was decided to incorporate DMP, a water-soluble form of dexamethasone, into the mix. DMP elutes rapidly and provides a burst of drug as early as eight hours.

Figure 16:
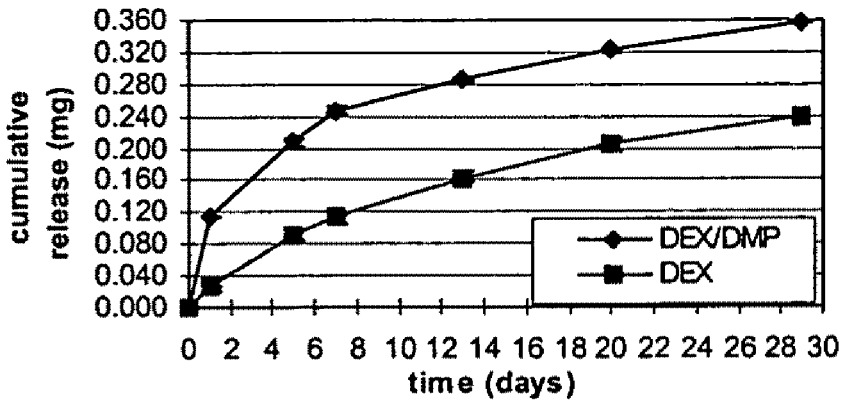
FIG. 16 shows (a) a comparison of the elution profiles of DEX-loaded inserts and DEX/DMP-loaded inserts; and (b) a breakdown of DEX and DMP elution from DEX/DMP-loaded inserts.
Figure 16:
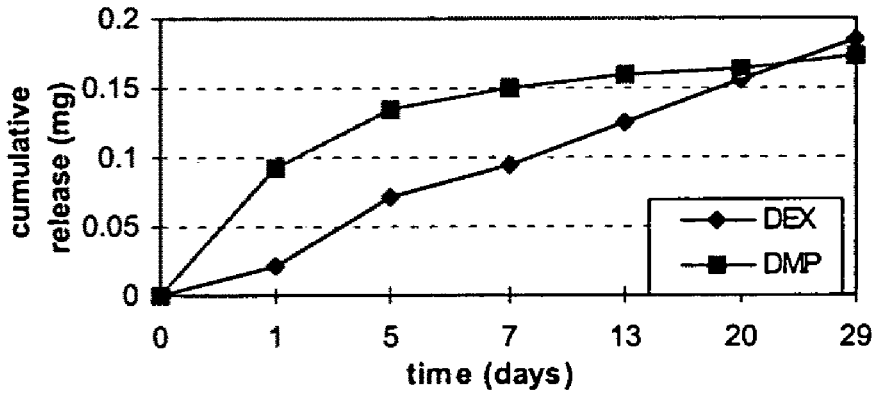

FIG. 16 compares elution profiles of 1% DEX-loaded inserts with 1% DEX/DMP-loaded (3:1 ratio) inserts. As seen in FIG. 16(a), the combination (DEX/DMP) displayed a higher profile, with an initial burst seen at day 1. This was attributable to the water soluble DMP present in the mixture. At day 29, approximately 8% of the DEX had been released and approximately 13% of the drug mixture had been released. FIG. 16(b) breaks the DEX/DMP curve in FIG. 16(a) into its individual components (i.e., DEX and DMP). This was mainly to determine how much of the two components is coming out at the different time points. At day 29, approximately 9% of the DEX had been released and approximately 25% of the DMP had been released.

Example 7

Bioactivity Studies for Dexamethasone Silicone Inserts

Dexamethasone activity is typically assessed by evaluating the effect of the drug on released inflammatory cytokines, namely interleukin 1α (IL-1α) and tumor necrosis factor α (TNF-α). Active dexamethasone suppresses cytokine production.

Materials and methods. Silicone inserts containing 5%, 2.5%, and 0.5% water-insoluble dexamethasone (DEX) were prepared as described in Example 6. In addition, silicone inserts containing 1% DEX, 1% DMP, and a 1% DEX/DMP (50:50) mixture were also prepared.

Freshly isolated human white blood cells, suspended in RPMI 1640 media and supplemented with 10% FBS, penicillin/streptomycin and L-glutamine, were seeded into sterile polypropylene tubes (2,000,000 cells/tube) containing the samples to be evaluated. The sample sizes were approximately 1 cm×1 cm and the cell solution added to each tube was 1 ml. To mimic a foreign body reaction the white blood cells were activated with the bacterial endotoxin lipopolysaccharide (LPS) at 10 µg/ml. After a 24 hour incubation at 37° C., the samples were removed and the contents of the wells were centrifuged at 3000 rpm for 5 minutes to pellet the unattached cells. The supernatants were harvested and stored at −85° C. until used. The TNF-α and IL-1α content in the extracts were analyzed using ELISAs (Quantikine™ Human TNF-α Immunoassay and Human IL-1α Immunoassay) from R&D Systems (Minneapolis, Minn.).

Figure 17:
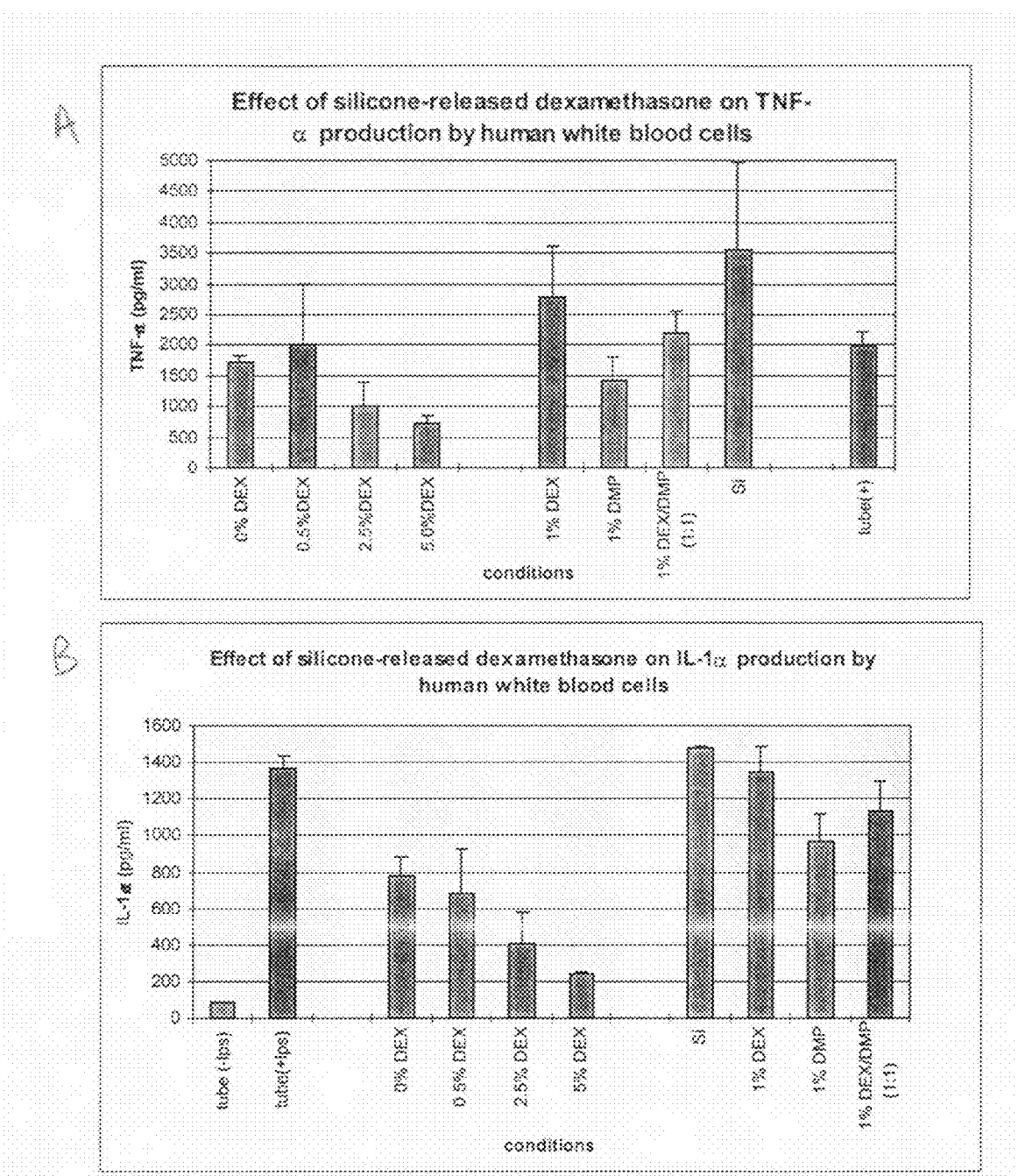
FIG. 17 shows the suppressive effects of dexamethasone eluted from DEX-loaded inserts on the production of the inflammatory cytokines (a) tumor necrosis factor α (TNF-α) and (b) interleukin 1α (IL-1α).

Results. Quantitation of cytokine markers is a traditional method for evaluating inflammation. The cell media was assayed for IL-1α and TNF-α, two potent cytokines which are released by activated macrophages and which through autocrine, paracrine, and endocrine actions are known to play multifunctional roles in the inflammatory and immune processes. As shown in FIG. 17, elution of DEX from the inserts suppressed the release of both TNF-α and IL-1α in a dose-dependent manner, with the 5% loaded sample showing the greatest inhibitory effect. FIG. 17 also shows the differences between 1% DEX, 1% DMP, and a 1% DEX/DMP (50:50) mixture. DMP, being water soluble, was observed to elute much quicker and therefore had the greatest effect at 24 hours. DEX, being non-water soluble, eluted out slowly and the effect was not very pronounced at 24 hours. The mixture, understandably, had an intermediate effect.

Example 8

In vitro Elution Profile for Polyester-Encased Dexamethasone Silicone Inserts

Sample preparation. DEX loaded samples were prepared as described in Example 6. The following configurations were tested and compared:

a) 1% DEX loaded silicone with and without polyester encasement b) 2.5% DEX loaded silicone with and without polyester encasement c) A 1% DEX/DMP (50:50) loaded silicone with and without polyester silicone Drug loaded silicone samples of roughly similar dimensions (1.5 cm×1.5 cm) were cut. Rectangular pieces of polyester fabric, measuring approximately 3 cm×1.5 cm, were fashioned into pouches by folding the fabric pieces in half and inserting the silicone samples between the folds. The free ends of the fabric were sewn together with 4-0 TI-CRON braided polyester sutures.

Drug elution was as described in Example 6, for a time period of 34 days.

Figure 18:
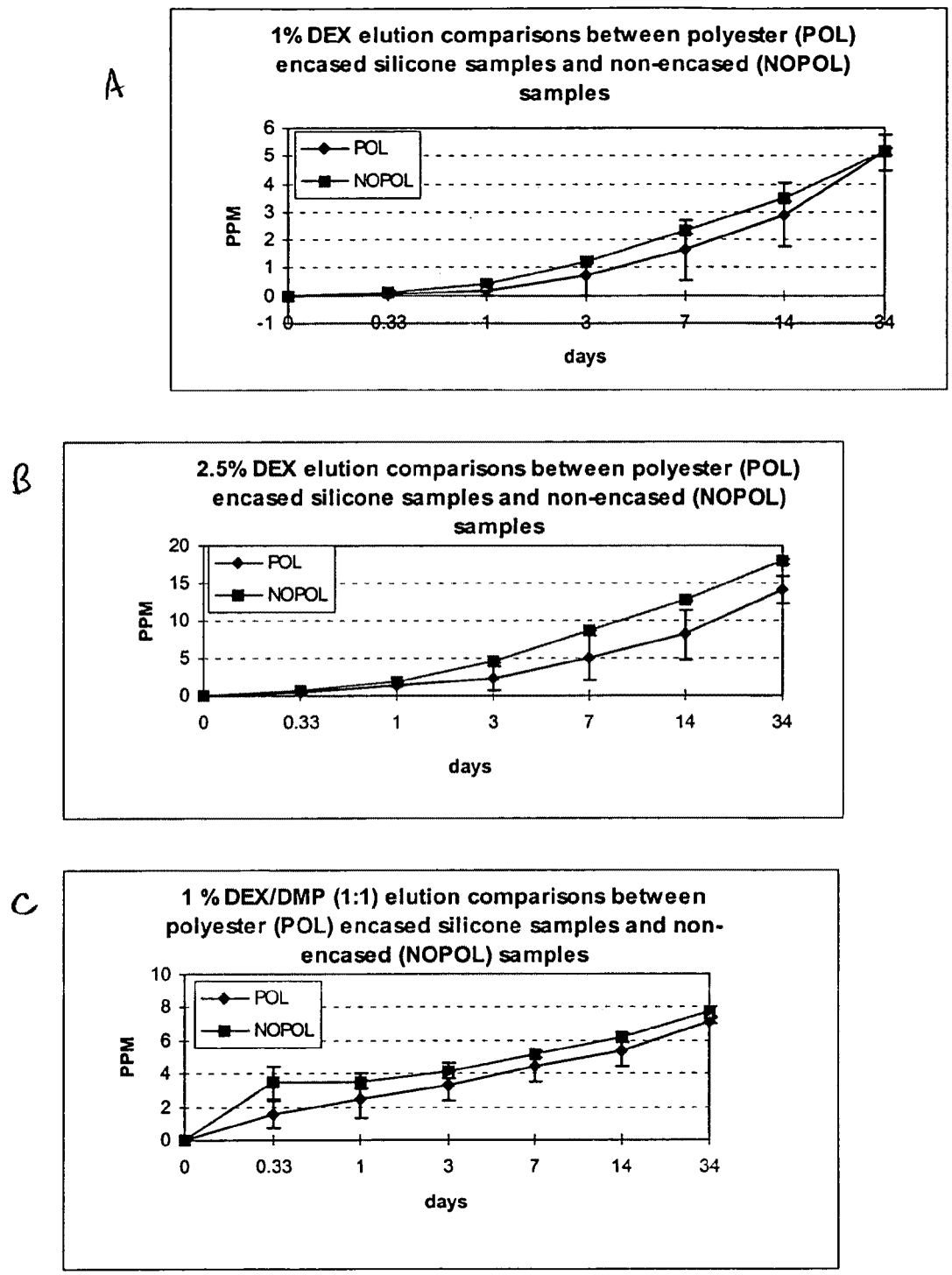
FIG. 18 shows the effect of a polyester encasement on elution of dexamethasone from a silicone sample (a) 1% DEX; (b) 2.5% DEX; (c) 1% DEX/DMP.

Results. FIG. 18 shows that the polyester pouches were permeable to dexamethasone. There appeared to be a slight, albeit insignificant, lag of the eluted drug with the encased material when compared to the bare material.

Example 9

Rat Cage Implant Study for Polyester-Encased Dexamethasone Silicone Inserts

The in vivo biocompatibility of DEX-loaded silicone was assessed using the cage implant system, a method that is widely reported in the literature (R. Marchant et al. *J. Biomed. Mat. Res.*, 17:301-325 (1983). Cylindrical stainless steel cages, containing the test samples, were implanted subcutaneously in rats. In order to simulate a sewing/annuloplasty ring, the Si/DEX test samples were inserted within Dacron™ polyester pouches. With minimal mechanical interference of surrounding tissues, the cage model provides a "standard inflammatory environment" in which the biocompatibility of the material can be studied in terms of cellular response and cell-material interactions. In this system, humoral and cellular components are monitored dynamically at different time points without sacrificing the animal.

Materials. Micronized, free base dexamethasone USP (EDP #221900) and dexamethasone sodium phosphate USP (EDP #221940) were obtained from Upjohn (Kalamazoo, MI); TI-CRON #4 polyester thread was obtained from Davis and Geck (Canada) and 304 Stainless steel metal wire mesh (mesh size=24, diam.=0.254 mm, interstices=0.8×0.8 mm) was purchased from Cleveland Wire Cloth and Manufacturing Co. (Cleveland, Ohio).

Silicone/drug formulation. Two different forms of dexamethasone were selected for this study. DEX, a non-water soluble form of dexamethasone, was used by itself, and DMP, a water soluble form of dexamethasone, was used in a 75% DEX:25% DMP mix. The drugs (DEX and DEX/DMP) were compounded into Medical Grade silicone (Si) (Table I). These Si/drug formulations also contained barium sulfate, a component that is normally added to impart radiopacity to the final product.

TABLE 1

|   | DEX Conc. (%) | Wt. DEX | Wt. Silicone | Wt. Barium Sulfate | Total Wt. |
|---|---|---|---|---|---|
| 1 | 1% | 0.2 gms DEX | 10.5 gms | 9.3 gms | 20 gms |
| 2 | 1% (75DEX:25DMP) | 0.15 gms DEX + 0.05 gms DMP | 10.5 gms | 9.3 gms | 20 gms |
| 3 | 0% | 0.00 gms | 10.5 gms | 9.5 gms | 20 gms |

Sample preparation. Samples of roughly similar dimensions (0.25 cm×2.5 cm) and weights (67-71 mg) were cut from the manufactured silicone slabs. At a 1% drug loading the theoretical drug quantities of DEX in the samples reflected a range of approximately 0.67-0.71 mg DEX. Rectangular pieces of polyester fabric, measuring approximately 1 cm×2.75 cm, were fashioned into pouches or pillows. This was accomplished by folding the fabric pieces in half and inserting the silicone samples between the folds. The three free ends of the pouches were hand sewn with TI-CRON #4 polyester thread. A total of 5 knots were used to keep the sample within the pouch. The sample belonging to treatment group E (see Table II) was encased within polyester that was heparinized using photolink technology. All handling, sizing, cutting, and weighing operations were done as cleanly as possible in a tissue culture Class II hood. The silicone samples were cleaned with forced air prior to being placed in the pouches.

Cage test system. Cylindrical cages, measuring approximately 3.5 cm in length and 1.0 cm in diameter, were fabricated from stainless steel metal wire meshes. The cages were then subjected to an extensive detergent washing and cleaning cycle. In each cleaned cage a pouch was placed containing the control (silicone with no drug), or the test material of interest (silicone with drug). Empty cages were also used as test controls. The cage/material assemblies were then triple bagged and subjected to one ETO sterilization cycle.

Test animals. The animals used for implantation were 4-month-old, 250-300 g, female Sprague Dawley rats purchased from the Charles River Laboratories, Wilmington, Mass. They were quarantined upon arrival. Each animal was numbered with a tattoo prior to surgery. This study was conducted in accordance with the recognized standards of good care as outlined in the "Guide for the Care and Use of Laboratory Animals" (NIH 1985).

Implantation procedure. Briefly, two 1.0 to 1.5-cm incisions were made in the skin on either side of the midline and about 2 cm above the tail. A pocket was made in the subcutaneous space just below the right and left shoulder blade using blunt dissection. A cage assembly was then inserted through the incision and positioned at the level of the panniculus carnosus, with the seam placed against the underlying muscle. The second assembly was implanted on the other side of the rat in the same fashion. The skin incision was closed with clips and the closed wound was then sprayed gently with Betadine solution. The number of animals and specimens per condition, as well as their designated IDs, are displayed in Table II. A total of 30 samples (2 per rat) were implanted into 15 rats.

TABLE II

| Material ID | Material/Condition | No. Rats | No. Samples |
|---|---|---|---|
| A | Empty Cage | 3 | 6 |
| B | Si/Dacron | 3 | 6 |
| C | 1% DEX/DMP(75:25)- Si/Dacron | 3 | 6 |
| D | 1% DEX-Si/Dacron | 3 | 6 |
| E | 1% DEX-Si/Dacron-Heparin | 3 | 6 |
| | Totals | 15 | 30 |

A&B = controls; B is the true control for C, D, and E.

Exudate analysis. Exudate was aspirated with syringes from the cages at days 4, 7, 14, and 21 post-implantation. To avoid interference with the body's inflammatory response, no more than 0.3 ml of exudate was collected from each cage at each time period. To screen for the presence of infection, a drop from each extracted exudate sample was cultured on 5% sheep's blood agar plates. The total leukocyte count was determined using a hemacytometer. For differential leukocyte determination, exudates containing approximately 30,000 white blood cells (leukocytes) were transferred to test tubes with 300 µl RPMI-1640. Aliquots (200 µl) of the cell suspension were spun down onto clean glass using a cytocentrifuge. These microslides were stained with Diff-Quik Stain and differentially quantitated for polymorphonuclear leukocytes (PMNs), monocyte-macrophages (Mo/MØs), and lymphocytes. After the 21-day exudate sampling, the rats were euthanized by carbon dioxide asphyxiation.

Cage analysis. Following the 21-day exudate withdrawal, the implanted cages were removed from the euthanized animals and immediately evaluated macroscopically by a pathologist. The top edge of the cage was cut with a pair of scissors along the inner surface seam. Intact and opened cages were examined and described. After analysis, the cages were immersed in 10% formalin. To assess the amount of fibrous tissue in the explanted cages, the polyester pouches were first removed from the cages. The cages were then dried at 60° C. for 48 hours and their dry weights were recorded. The tissue was subsequently removed by digestion in 6N KOH for 2 hours at 80° C., and the weight of each tissueless cage was again recorded. The difference between these two-weights provided an indication of the amount of dry fibrous tissue associated with each cage.

Histology. One sample each from groups B, C, D, and E, following formalin fixation, was washed in phosphate buffered saline, dehydrated through graded ethanol washes and processed for paraffin embedding. Four micrometer-thin transverse sections were cut and stained with either Masson's trichrome stain or hematoxylin and eosin stains.

Statistical analysis. All data are expressed as mean (± standard error of mean). For total cell counts Dunnett's Method at 95% level of confidence (p<0.05) was used to compare group means. Comparisons of the different material sub-groups were as such: test materials (C, D, E) vs. control materials (B). On day 14, one high data point was removed from groups B and C for the statistical analysis. Similarly, on day 21, one high data point was removed from all the groups.

Figure 19:
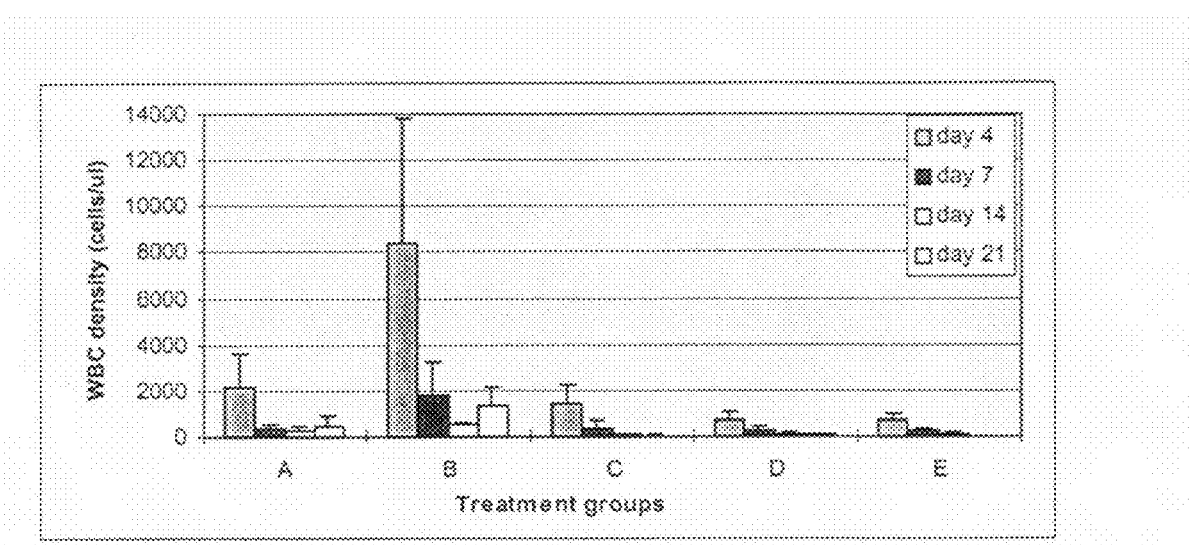
FIG. 19 shows white blood cell density as a function of time for rats treated with Si/DEX samples and control rats.

Results. The white blood cell densities that were determined in the drawn exudates at 4, 7, 14, and 21 days post implantation are displayed in Table III and FIG. 19. In general, a gradual decrease of the counts was observed after 4 days with all the test groups. The DEX-containing materials (C, D, E) generated numbers that were considerably lower than both controls (A, B) at all time points. A direct comparison of the DEX-mediated counts with that of the control group B, the true control for this study, revealed a statistically significant reduction at all time points. By pooling the values of all the DEX-containing materials (C, D, E) together and comparing them to the control B we calculated percent reductions in leukocyte densities on the order of 88.5% for day 4, 82.5% for day 7, 85% for day 14, and 97.4% for day 21.

TABLE III

White Blood Cell Density (cells/µl)

| Day | A | B | C | D | E |
|---|---|---|---|---|---|
| 4 | 2198 ± 1371 | 8417 ± 5445 | 1467 ± 805* | 754 ± 322* | 690 ± 340* |
| 7 | 391 ± 120 | 1782 ± 1447 | 379 ± 341* | 293 ± 172* | 262 ± 141* |
| 14 | 272 ± 156 | 521 ± 89 | 63 ± 52* | 93 ± 85* | 72 ± 108* |
| 21 | 423 ± 500 | 1372 ± 840 | 30 ± 16* | 54 ± 50* | 24 ± 21* |

*Statistically Significant at the 0.05 level

There appeared to be no obvious differences between group C, which contained the drug combination (DEX/DMP), and group D, which contained the single drug (DEX). Apparently, at the first time point of 4 days, there was already sufficient DEX present to effect a reduction in inflammatory cell counts. The DEX, therefore, appeared to have masked the effect of DMP, and that in order to observe a DMP effect, a much earlier time point (perhaps at day 1) would need to be considered. In the case of groups D and E, in which the variation between the two treatment groups was the heparin coating applied to the polyester fabric, the counts in group E, although not significantly different from those in group D, were consistently lower at all the time points.

A macroscopic examination of the cages following explanation further highlighted the differences between the Si/DEX and the controls. The non-DEX containing cages were marked by considerable tissue ingrowth (groups A and B). This was especially pronounced in the cages that contained the polyester pouch (group B), once again attesting to the inflammatory nature of the material. In general, the cages of group B were extensively covered with thickened translucent to opaque tissue ingrowth that was also marked with multifocal granular redness. The fabric was found to be covered with thin tissue and had multifocal blood clots on the surface. In these cages approximately 5-30% of the mesh was visible. In stark contrast, the cages that contained the drug loaded samples (groups C, D, E), in general, appeared to be remarkably free of tissue ingrowth, with approximately 90-95% of the mesh clearly visible. The polyester material was covered with a thin transparent layer of tissue. Out of a total of eighteen DEX containing samples only one became infected, and the infection was not likely drug related as it was already apparent at day 4, when the exudate was examined. In addition, the infection remained very localized for the entire twenty one day duration of the study and did not affect the second cage in the same animal.

The amount of dry fibrous tissue present in the cages was quantitated and compared. The fibrous capsule formation in the drug loaded cages (C=45±20.63 mg, D=22.5±11.66 mg, E=13.33±7.63 mg) was found to be significantly lower than control B cages (307±74.81 mg) and the empty cages (249.5±31.3 mg). From the three drug containing groups, the cages with the heparinized pouches in group E registered the lowest fibrous capsule weight. This finding appeared to be consistent with the lower leukoctye densities observed in Table III.

Figure 20:
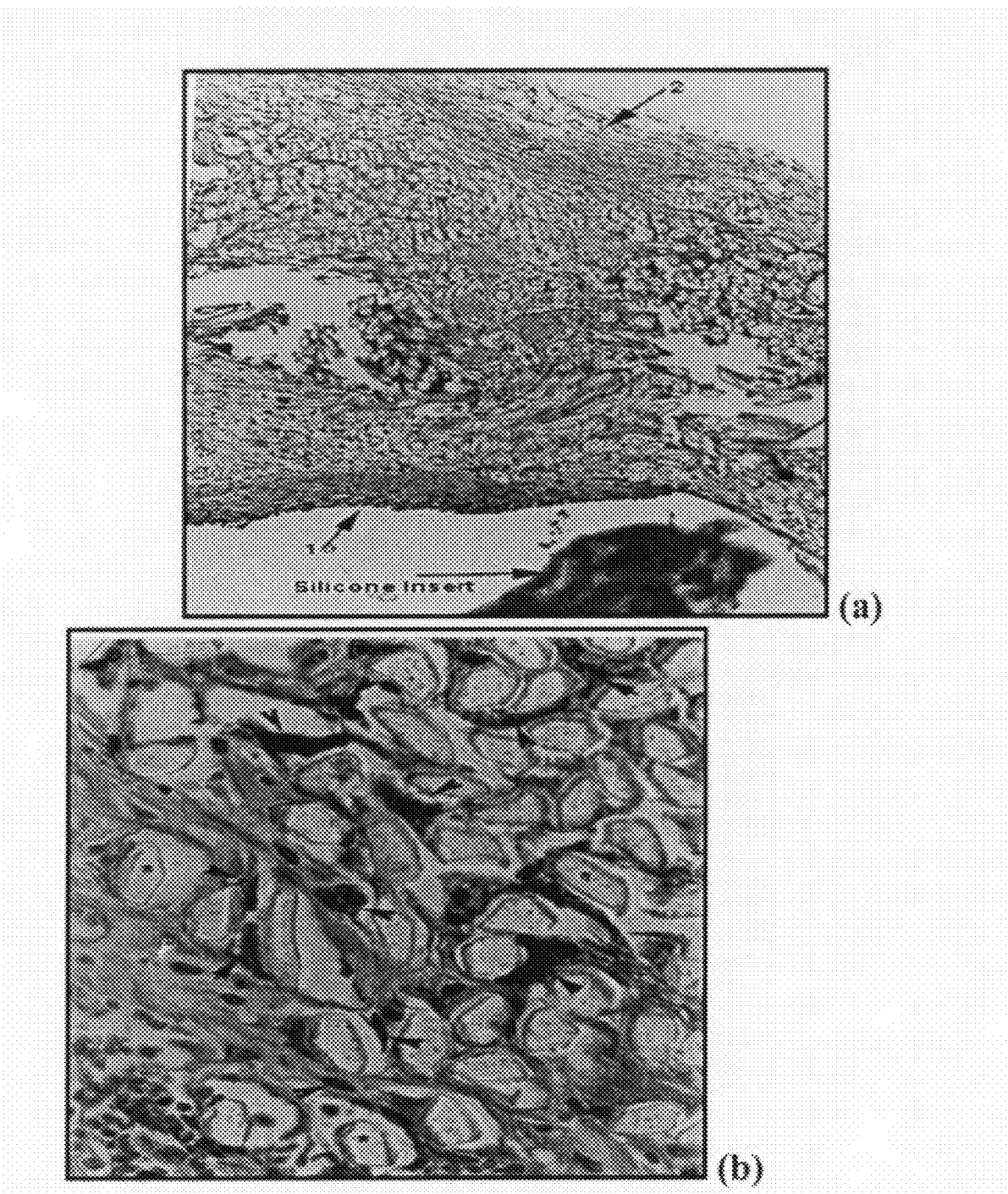
FIG. 20 shows hemotoxylin and eosin stained histological sections of explanted silicone samples after 21 days; (a) control sample (Si with no DEX) at an original magnification of 100× (1=inner surface of the Dacron™ fabric, the side that was in contact with the silicone insert; 2=outer surface of the Dacron™; *=individual Dacron™ fibers); (b) 500× image of the stained control; the arrow heads point to the presence of single and multi-nucleated macrophages around the fibers; (c) 100× image of a sample containing DEX; and (d) 200× image of a sample containing DEX.
Figure 20:
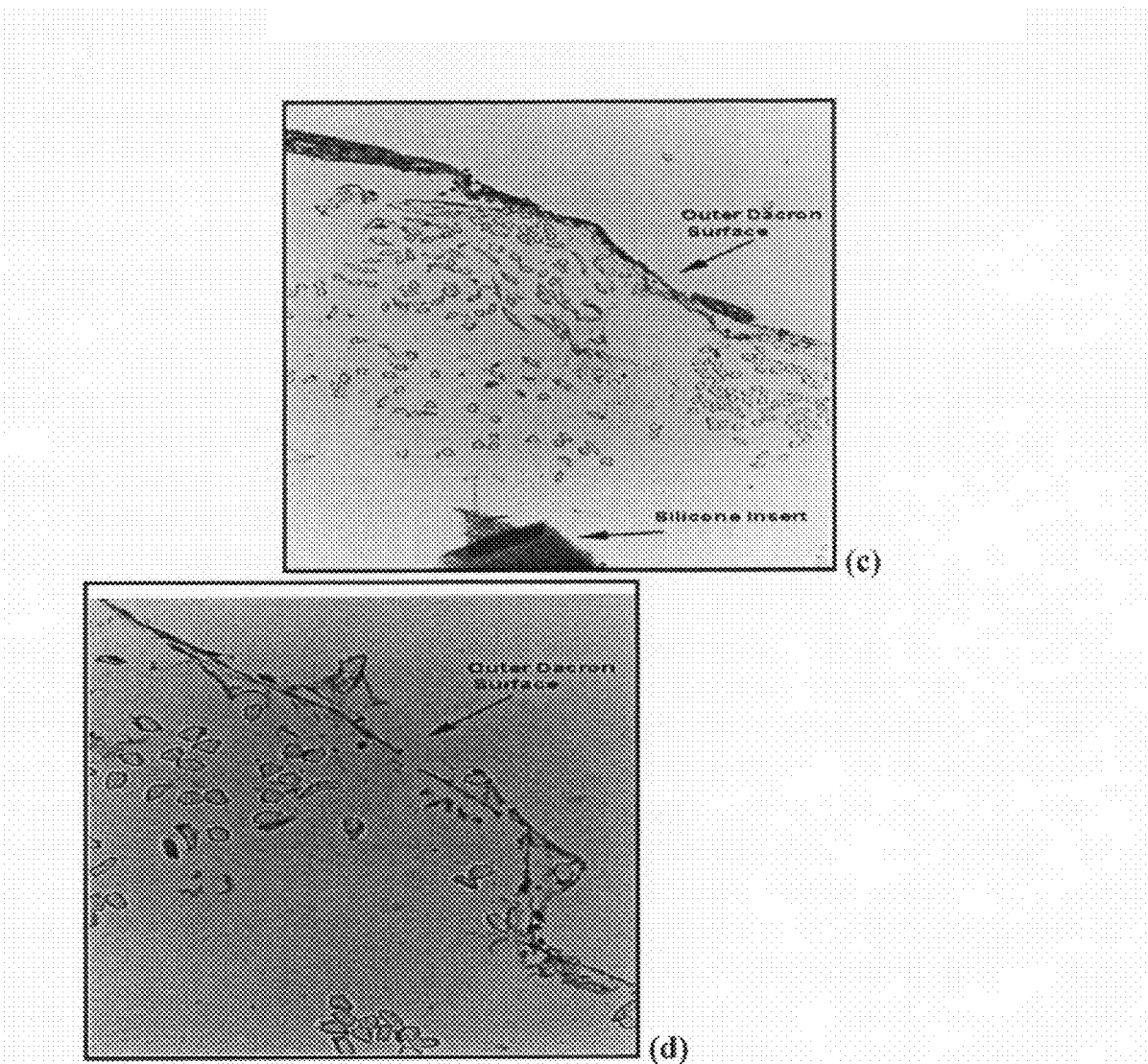

The Dacron pouches from the cages were histologically analyzed to determine the nature and extent of tissue ingrowth. As was the case with the control cages (Group B), the Dacron pouches from the control cages were also characterized by extensive cellular and tissue ingrowth (FIG. 20(a)). A lingering inflammatory response, mainly in the form of macrophages and a few PMNs, was evident. Also visible were multinucleated foreign body giant cells forming around individual fibers of the polyester fabric (FIG. 20(b)). In addition, the sample showed a high degree of vascularity in and around the sample. The tissue observed on the outer surface of the Dacron was loosely packed and randomly oriented, a response that is consistent with that observed in porous implants. The inner surface of the Dacron, on the other hand, revealed denser, more organized, highly oriented fibrous tissue, running parallel to the plane of the silicone sample. This formation is characteristic of a host reaction to non-porous implants. In contrast to the controls, the Dacron pouches surrounding the DEX-containing silicone samples indicated a remarkable absence of tissue ingrowth (FIGS. 20(c) and (d)). In almost all the cases a very thin layer of fibrous tissue, sparsely populated with rounded macrophages, was found surrounding the outer surface of the fabric.

The complete disclosures of the patents, patent applications, and publications listed herein are incorporated by reference, as if each were individually incorporated by reference. The preceding specific embodiments are illustrative of the practice of the invention. It is to be understood, therefore, that other expedients known to those skilled in the art or disclosed herein, may be employed without departing from the invention or the scope of the appended claims. For example, the present invention has further utility in reconstructive surgery, such as breast implants, calf implants, facial reconstruction and the like. It is readily apparent to one skilled in the art that the present invention, relating as it does to a medical device comprising a biocompatible drug-eluting material overlaid with a fabric that promotes tissue ingrowth, can be practiced in a wide variety of tissue engineering applications.

What is claimed is:

1. A heart valve prosthesis comprising a sewing ring comprising an annular support initially formed from a biostable polymer mixed with a steroidal agent, said annular support overlayed by a polyester fabric overlayer, wherein said annular support provides at least one therapeutic effect to the fabric overlayer.

2. The heart valve prosthesis of claim 1, wherein the biostable polymer is selected from the group consisting of polyurethanes, silicones and combinations thereof.

3. The heart valve prosthesis of claim 1, wherein the steroidal agent comprises an anti-inflammatory agent selected from the group consisting of dexamethasone, a derivative thereof, or a salt thereof.

4. The heart valve prosthesis of claim 1, which is a bioprosthetic heart valve.

5. The heart valve prosthesis of claim 1, which is a mechanical heart valve.

6. A heart valve prosthesis comprising a sewing ring comprising a body portion initially formed from a polymer mixed with a steroidal agent, said body portion overlayed by a polyester fabric overlayer, and wherein said body portion provides at least one therapeutic effect to the fabric overlayer.

7. The heart valve prosthesis of claim 6, wherein the heart valve prosthesis additionally comprises metal or metal alloy components.

8. The heart valve prosthesis of claim 6, wherein the steroidal agent comprises and anti-inflammatory agent selected from the group consisting of dexamethasone, a derivative thereof, or a salt thereof.

9. A bioprosthetic heart valve comprising a polymer insert containing struts attached to tissue leaflets to form a valve housing, wherein a fabric sheath encloses the polymer insert to form a sewing ring, said sewing ring attached circumferentially to the base of the valve housing, the improvement comprising the polymer insert is initially formed with a releasable steroidal agent wherein the releasable steroidal agent provides at least one therapeutic effect to the fabric overlayer.

10. The bioprosthetic heart valve of claim 9, wherein the polymer insert comprises silicone.

11. The bioprosthetic heart valve of claim 10, wherein the polymer insert comprises radiopaque flexible silicone rubber and the steroidal agent.

12. The bioprosthetic heart valve of claim 9, wherein the steroidal agent comprises an anti-inflammatory agent.

13. The bioprosthetic heart valve of claim 12, wherein the anti-inflammatory agent is dexamethasone, a derivative thereof, or a salt thereof.

14. The bioprosthetic heart valve of claim 9, wherein the polymer insert further comprises an antimicrobial agent.

15. The bioprosthetic heart valve of claim 9, wherein the flow occluder comprises pericardium or aortic root tissue from an animal.

16. The bioprosthetic heart valve of claim 15, wherein the flow occluder comprises pericardium or aortic root tissue from a pig.

17. An annuloplasty ring comprising a body portion overlaid by a polyester fabric overlayer, the body portion initially formed from a biostable polymer mixed with a releasable steroidal agent wherein the releasable steroidal agent provides at least one effect to the fabric overlayer.

18. The annuloplasty ring of claim 17, wherein the biostable polymer is selected from the group consisting of polyurethanes, silicones and combinations thereof.

19. The annuloplasty ring of claim 17, wherein the steroidal agent comprises an anti-inflammatory agent selected from the group consisting of dexamethasone, a derivative thereof, or a salt thereof.

20. The annuloplasty ring of claim 17, wherein the annuloplasty ring further comprises an antimicrobial agent.

21. A method for replacing a heart valve in a patient comprising implanting a prosthetic heart valve into the patient, wherein the prosthetic heart valve comprises a sewing ring comprising a body portion initially formed from a polymer mixed with a steroidal agent, said body portion additionally overlayed by a fabric overlayer.

22. The method of claim 21, wherein the constituent material of the body portion comprises a biostable polymer.

23. The method of claim 22, wherein the biostable polymer comprises a polymer selected from the group consisting of polyurethanes, silicones and combinations thereof.

24. The method of claim 22, wherein the metal or metal alloy comprises titanium.

25. The method of claim 21, wherein the constituent material of the body portion additionally comprises a metal or a metal alloy.

26. The method of claim 21, wherein the therapeutic agent comprises an anti-inflammatory agent.

27. The method of claim 26, wherein the anti-inflammatory agent is dexamethasone, a derivative thereof, or a salt thereof.

28. A method for ameliorating the inflammatory response associated with heart valve replacement in a patient comprising implanting a prosthetic heart valve into the patient, wherein the prosthetic heart valve comprises a sewing ring comprising a body portion comprising a polymer initially formed with a releasable anti-inflammatory agent, said body portion overlayed by a fabric overlayer wherein the releasable anti-inflammatory agent provides at least one therapeutic effect to at least one additional component of the heart valve.

29. The method of claim 28, wherein the fabric overlayer comprises polyester.

30. The method of claim 28, wherein the anti-inflammatory agent is dexamethasone, a derivative thereof, or a salt thereof.

31. The method of claim 28, wherein implantation of the prosthetic heart valve is accompanied by reduced pannus formation at the implant site.

32. A method for ameliorating the inflammatory response associated with heart valve repair in a patient comprising implanting an annuloplasty ring into the patient, wherein the annuloplasty ring comprises a body portion comprising a biostable polymer initially formed with a releasable anti-inflammatory agent, said body portion overlaid by a fabric overlayer wherein the releasable anti-inflammatory agent provides at least one therapeutic effect to the fabric overlayer.

33. The method of claim 32, wherein the fabric overlayer comprises polyester.

34. The method of claim 32, wherein the anti-inflammatory agent is dexamethasone, a derivative thereof, or a salt thereof.

35. The method of claim 32, wherein implantation of the annuloplasty ring is accompanied by reduced pannus formation at the implant site.

36. A method of making a medical sewing ring comprising:
   initially forming the annular insert by mixing a releasable steroidal agent with a biocompatible polymer; and
   enclosing the annular insert in a fabric sheath;
   wherein the releasable steroidal agent provides at least one therapeutic effect to the fabric sheath.

37. The method of claim 36, wherein the constituent material comprises a polymer.

38. The method of claim 37, wherein the constituent material comprises a biostable polymer.

39. The method of claim 38, wherein the biostable polymer is selected from the group consisting of polyurethanes, silicones and combinations thereof.

40. The method of claim 36, wherein the constituent material comprises a metal or a metal alloy.

41. The method of claim 40, wherein the metal or metal alloy is selected from the group consisting of titanium, tantalum, titanium alloys, cobalt chrome alloys, nickel chrome alloys, stainless steels, and combinations thereof.

42. The method of claim 36, wherein the fabric sheath comprises polyester.

43. The method of claim 36, wherein the steroidal agent comprises an anti-inflammatory agent.

44. The method of claim 43, wherein the anti-inflammatory agent is dexamethasone, a derivative thereof, or a salt thereof.

45. The method of claim 36, wherein the annular insert further comprises an antimicrobial agent.

* * * * *